(12) United States Patent
Nelson et al.

(10) Patent No.: US 8,778,846 B2
(45) Date of Patent: *Jul. 15, 2014

(54) COMPOSITION, DEVICE AND ASSOCIATED METHOD

(75) Inventors: John Richard Nelson, Clifton Park, NY (US); Bahram Moasser, Gaithersburg, MD (US); Anup Sood, Clifton Park, NY (US); Gregory Andrew Grossmann, Halfmoon, NY (US); Su Lu, Shanghai (CN); Zhida Pan, Zhejiang (CN); Liangliang Qiang, Shanghai (CN); John Yupeng Gui, Schenectady, NY (US); Wei Cai, Shanghai (CN); Zhixin Zheng, Shanghai (CN)

(73) Assignee: General Electric Company, Niskayuna, NY (US)

( * ) Notice: Subject to any disclaimer, the term of this patent is extended or adjusted under 35 U.S.C. 154(b) by 1559 days.

This patent is subject to a terminal disclaimer.

(21) Appl. No.: 11/680,652

(22) Filed: Mar. 1, 2007

(65) Prior Publication Data

US 2012/0122735 A1    May 17, 2012

Related U.S. Application Data

(60) Provisional application No. 60/868,431, filed on Dec. 4, 2006.

(51) Int. Cl.
*C40B 40/04* (2006.01)
*G01N 33/53* (2006.01)
*G01N 33/566* (2006.01)

(52) U.S. Cl.
USPC ............... 506/15; 435/7.1; 435/7.9; 436/501

(58) Field of Classification Search
CPC ............................................... G01N 33/5308
See application file for complete search history.

(56) References Cited

U.S. PATENT DOCUMENTS

| | | | |
|---|---|---|---|
| 4,511,478 A * | 4/1985 | Nowinski et al. | ............ 210/691 |
| 4,749,647 A | 6/1988 | Thomas et al. | |
| 5,035,997 A | 7/1991 | Oster et al. | |
| 5,451,503 A * | 9/1995 | Hogan et al. | ............... 435/6.1 |
| 6,017,707 A | 1/2000 | Mandrand et al. | |
| 7,339,006 B2 | 3/2008 | Giardello et al. | |
| 2002/0001845 A1 * | 1/2002 | Klaerner et al. | ................ 436/8 |
| 2003/0059822 A1 | 3/2003 | Chan et al. | |
| 2003/0113740 A1 | 6/2003 | Mirkin et al. | |
| 2004/0029135 A1 * | 2/2004 | Ramberg | ................... 435/6 |
| 2004/0204556 A1 * | 10/2004 | Matyjaszewski et al. | . 526/329.7 |
| 2005/0196790 A1 | 9/2005 | Rooke | |
| 2005/0221408 A1 | 10/2005 | Nalefski et al. | |

FOREIGN PATENT DOCUMENTS

| | | |
|---|---|---|
| EP | 1130113 A1 | 9/2001 |
| EP | 1343012 | 9/2003 |
| WO | 2005002438 | 3/2005 |
| WO | 2007044727 A2 | 4/2007 |

OTHER PUBLICATIONS

Marc Husemann et al., Surface-Initiated Polymerization for Amplification of Self-Assembled Monolayers Patterned by Microcontact Printing, Angew. Chem. int. Ed., Communications, vol. 38, No. 5, pp. 647-649, 1999.

Rahul R. Shah et al., "Using Atom Transfer Radical Polymerization to Amplify Monolayers of Initiators Patterned by Microcontact Printing Into Polymer Brushes for Pattern Transfer", Macromolecules, vol. 33, pp. 597-605, 2000.

Xinhui Lou et al., "Detection of DNA Point Mutation by Atom Transfer Radical Polymerization", Anal. Chem., vol. 77, pp. 4698-4705, 2005.

Lou et al., "DNA-Accelerated Atom Transfer Radical Polymerization on a Gold Surface", Langmuir, vol. 22, pp. 2640-2646, 2006.

Licitra et al.,"A Three-hybrid system for detecting small ligand-protein receptor interactions", Biochemistry, Proc. Natl. Acad. Sci. USA, Nov. 1996, vol. 93, pp. 12817-12821.

PCT/US2007/086328 International Search Report dated Apr. 10, 2008.

* cited by examiner

*Primary Examiner* — Michael G Hartley
*Assistant Examiner* — Sun Y Kim
(74) *Attorney, Agent, or Firm* — Melissa K. Dobson

(57) ABSTRACT

A composition includes a first probe, a first initiator component bonded to the first probe, a second probe, and a second initiator component bonded to the second probe. The first probe and the second probe are capable of binding to a single analyte, and the first initiator component and the second initiator component are capable of forming an initiator when present in proximity to each other and when the first probe and the second probe are bonded to the analyte. An associated kit, device, and method are provided.

18 Claims, 27 Drawing Sheets

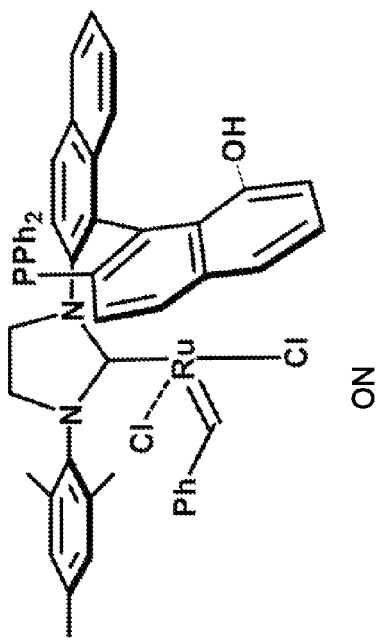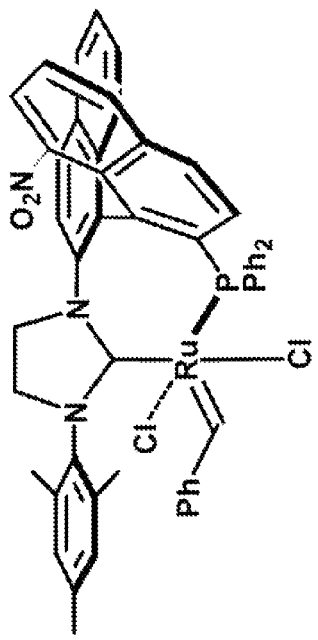
FIG. 3

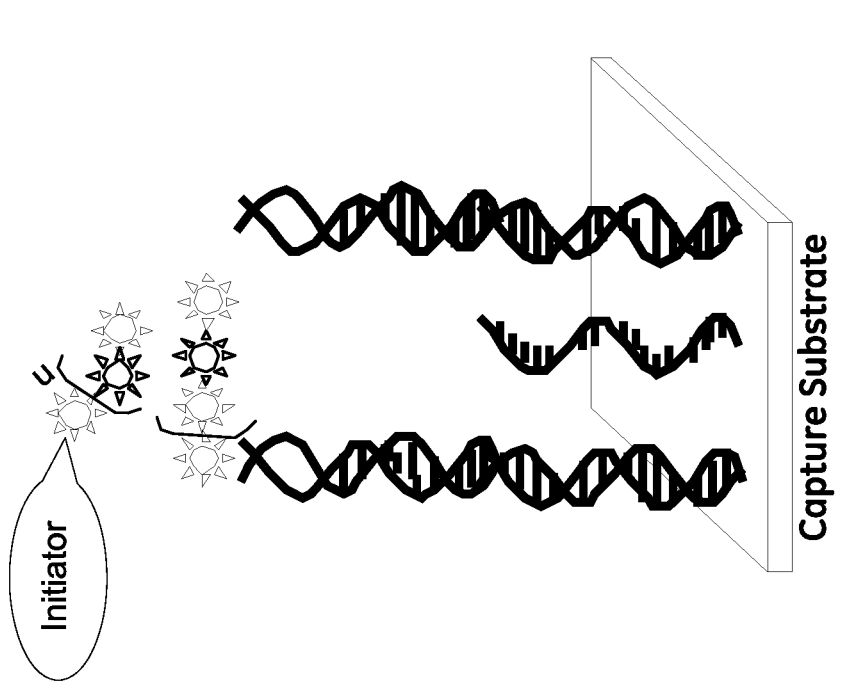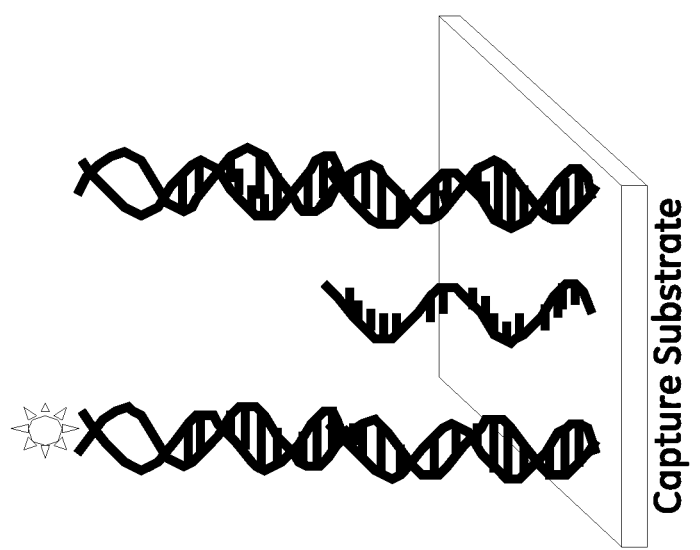
FIG. 27

COMPOSITION, DEVICE AND ASSOCIATED METHOD

CROSS REFERENCE TO RELATED APPLICATIONS

This application claims priority to and the benefit of provisional U.S. Patent Application No. 60/868,431, entitled "COMPOSITION, DEVICE AND ASSOCIATED METHOD", filed on Dec. 4, 2006, which is hereby incorporated by reference in its entirety.

BACKGROUND

1. Technical Field

The invention includes embodiments that relate to a composition for detecting an analyte. The invention includes embodiments that relate to a kit and a device for detecting an analyte. Thr invention includes embodiments that relate to a method of detecting an analyte.

2. Discussion of Related Art

Detection of chemical and biological analytes may be required in various applications, for example, in pharmaceutical research, clinical diagnostics, food and beverage-quality monitoring, water purification, soil, water, and air-pollution monitoring, or in detection of chemical or biological warfare agents.

One or more chemical or biological analyte may be detected using molecules (probes) capable of specifically recognizing the analyte. Recognition may occur via highly specific interactions between two molecules, for example, an enzyme and a substrate, antibody and antigen, and the like. An occurrence or non-occurrence of the recognition reaction may be detected using suitable detection means as indication of the presence or absence of the analyte. In some applications, the analyte may be present in a very low concentration and the recognition event between the probe and the analyte may not be easily detected. Analyte amplification techniques may be employed to increase the concentration of the analyte, which may make it difficult to accurately quantify the analyte. In some analyte detection techniques, the recognition between the probe and the analyte may be partial or may not be completely specific resulting in false positives.

It may be desirable to have compositions, devices, and methods for detection of analytes that have characteristics or features that are different from those currently available.

BRIEF DESCRIPTION

In one embodiment, a composition is provided. The composition includes a first probe, a first initiator component bonded to the first probe, a second probe, and a second initiator component bonded to the second probe. The first probe and the second probe are capable of binding to a single analyte, and the first initiator component and the second initiator component are capable of forming an initiator when present in proximity to each other and when the first probe and the second probe are bonded to the analyte.

In one embodiment, a kit is provided. The kit includes a composition capable of detecting an analyte. The composition includes a first probe bonded to a first initiator component, a second probe bonded to a second initiator component, and a polymer precursor;

In one embodiment, an article is provided. The article includes a substrate having an analyte disposed on a surface of the substrate. The substrate is capable of associating with a polymer through the analyte, a first probe bonded to a first initiator component, a second probe bonded to a second initiator component, and an initiator formed when the first initiator component and the second initiator component are proximate to each other.

In one embodiment, a method is provided. The method includes contacting the composition with an analyte to form a complex; wherein the complex has the first initiator and the second initiator proximate to each other. The method further includes forming an initiator from the first initiator component and the second initiator component and contacting the complex with at least one polymer precursor.

BRIEF DESCRIPTION OF DRAWING FIGURES

FIG. 3 is a schematic illustration of an activatable initiator in accordance with one embodiment of the invention.

Figure 22B:
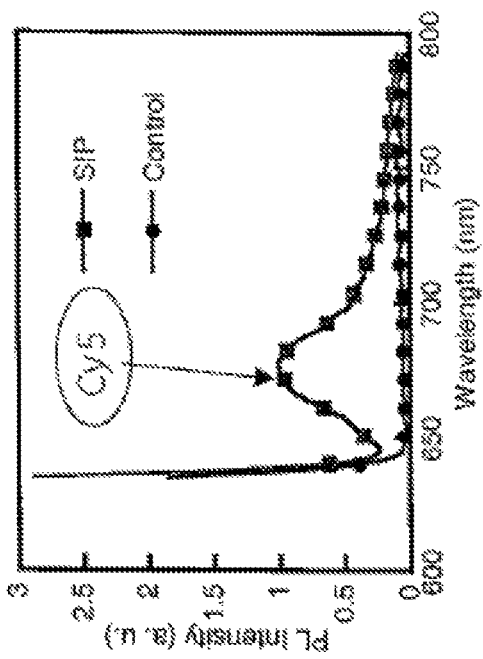
Figure 22A:
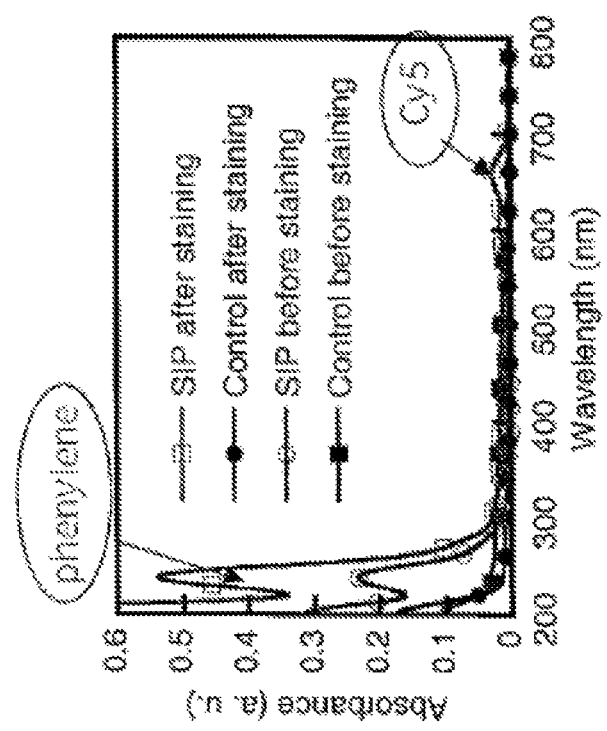

FIGS. 22($a$) and 22($b$) show the absorbance and fluorescence intensity of slides prepared in Example 16.

Figure 23B:
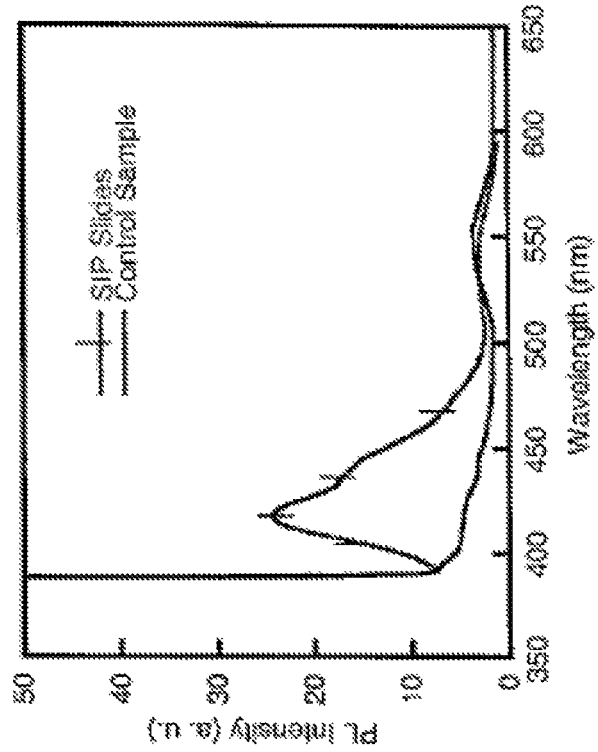
Figure 23A:
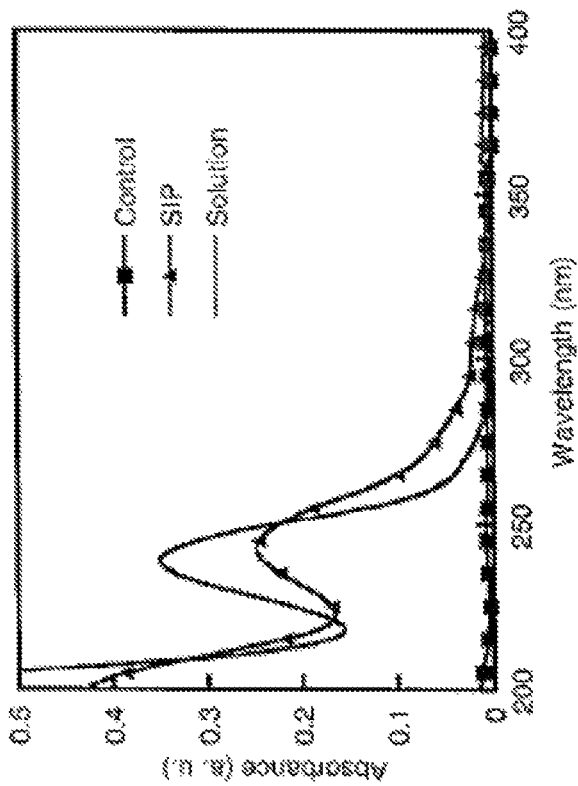

FIGS. 23($a$) and 23($b$) show the absorbance and fluorescence intensity of slides prepared in Example 17.

Figure 24:
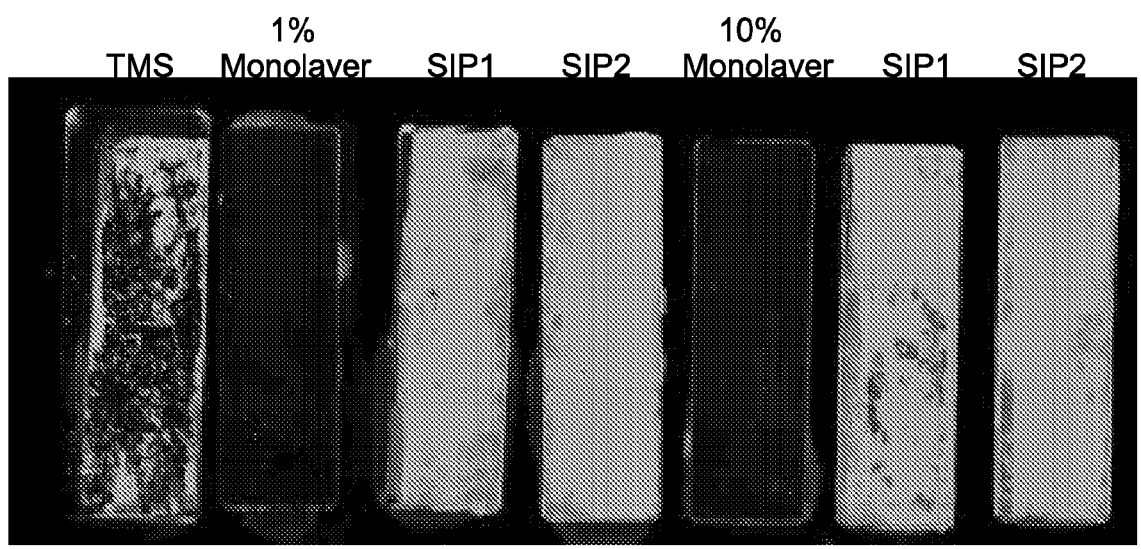

FIG. 24 shows the fluorescence images of slides prepared in Example 20.

Figure 25:
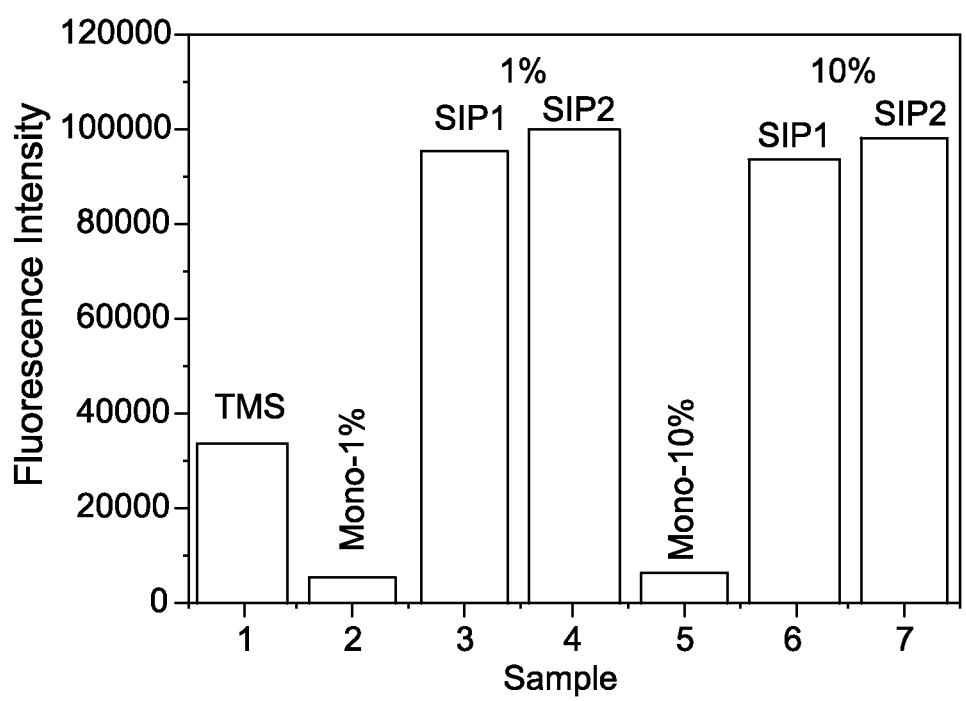

FIG. 25 shows the fluorescence intensity of slides prepared in Example 20.

Figure 26:
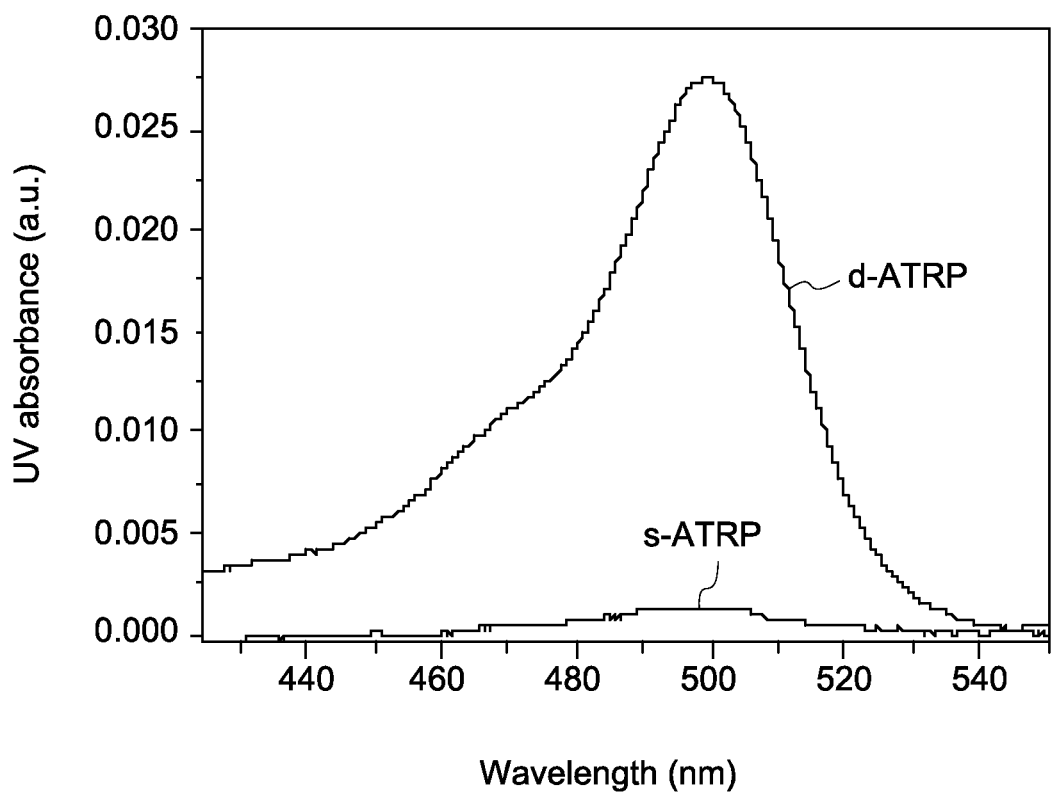

FIG. 26 shows the fluorescence intensity of slides prepared in Example 20.

FIG. 27 is a schematic illustration of a signal-generator-conjugated DNA hybrid and a DNA hybrid functionalized with a surface initiated polymer.

Figure 28:
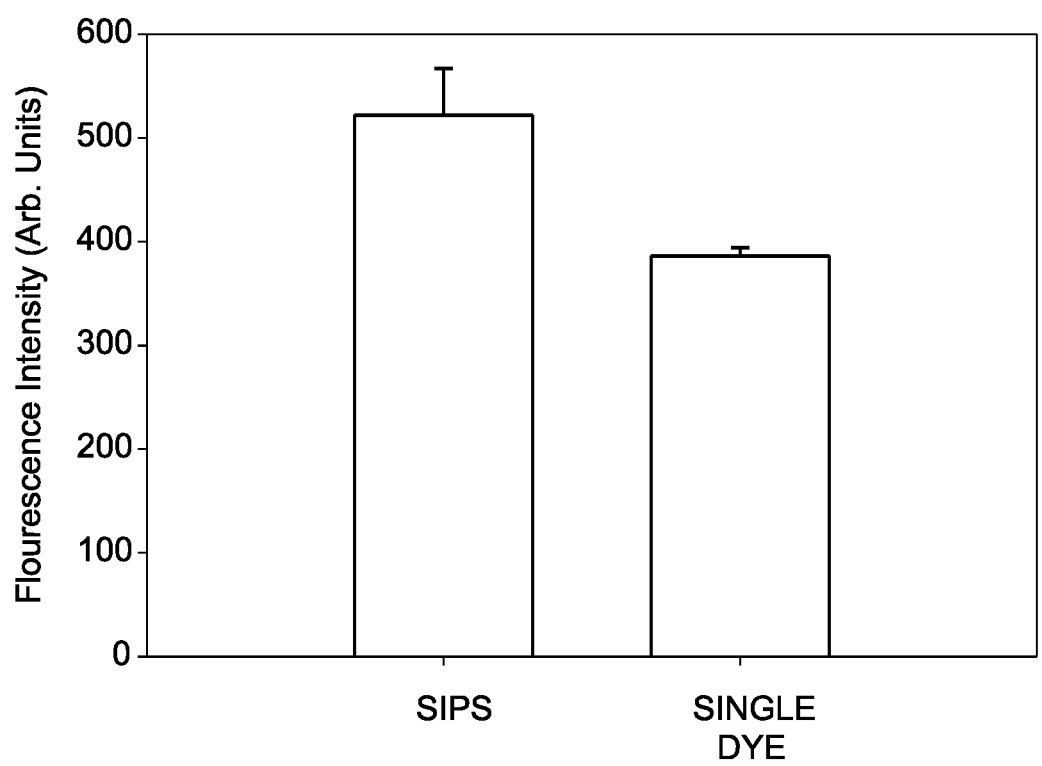

FIG. 28 shows the fluorescence intensity of composition prepared in Example 24.

DETAILED DESCRIPTION

The invention includes embodiments that relate to a composition for detecting an analyte. The invention includes embodiments that relate to a kit and a device for detecting an analyte. Thr invention includes embodiments that relate to a method of detecting an analyte.

In the following specification and the clauses which follow, reference will be made to a number of terms have the following meanings. The singular forms "a", "an" and "the" include plural referents unless the context clearly dictates otherwise. Approximating language, as used herein throughout the specification and clauses, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts, while still being considered free of the modified term.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity can not occur—this distinction is captured by the terms "may" and "may be".

As used herein, the term "peptide" refers to a linear sequence of amino acids connected to the other by peptide bonds between the alpha amino and carboxyl groups of adjacent amino acids. The amino acids may be the standard amino acids or some other non standard amino acids. Some of the standard nonpolar (hydrophobic) amino acids include alanine (Ala), leucine (Leu), isoleucine (Ile), valine (Val), proline (Pro), phenylalanine (Phe), tryptophan (Trp) and methionine (Met). The polar neutral amino acids include glycine (Gly), serine (Ser), threonine (Thr), cysteine (Cys), tyrosine (Tyr), asparagine (Asn) and glutamine (Gln). The positively charged (basic) amino acids include arginine (Arg), lysine (Lys) and histidine (His). The negatively charged (acidic) amino acids include aspartic acid (Asp) and glutamic acid (Glu). The non standard amino acids may be formed in body, for example by posttranslational modification, some examples of such amino acids being selenocysteine and pyrolysine. The peptides may be of a variety of lengths, either in their neutral (uncharged) form or in forms such as their salts. The peptides may be either free of modifications such as glycosylations, side chain oxidation or phosphorylation or comprising such modifications. Substitutes for an amino acid within the sequence may also be selected from other members of the class to which the amino acid belongs. A suitable peptide may also include peptides modified by additional substituents attached to the amino side chains, such as glycosyl units, lipids or inorganic ions such as phosphates as well as chemical modifications of the chains. Thus, the term "peptide" or its equivalent may be intended to include the appropriate amino acid sequence referenced, subject to the foregoing modifications, which do not destroy its functionality.

As used herein, the term "carbohydrate" refers to a polyhydroxy aldehyde or ketone, or a compound that can be derived from them by any of several means including (1) reduction to give sugar alcohols; (2) oxidation to give sugar acids; (3) substitution of one or more of the hydroxyl groups by various chemical groups, for example, hydrogen may be substituted to give deoxysugars, and amino group (NH2 or acetyl-NH) may be substituted to give amino sugars; (4) derivatization of the hydroxyl groups by various moieties, for example, phosphoric acid to give phosphor sugars, or sulphuric acid to give sulfo sugars, or reaction of the hydroxyl groups with alcohols to give monosaccharides, disaccharides, oligosaccharides, and polysaccharides. Carbohydrate group may include monosaccharides, disaccharides, or oligosaccharides. Suitable monosachharides may include, but are not limited to, glucose, fructose, mannose and galactose. A disachharide, as further defined herein, is a compound, which upon hydrolysis yields two molecules of a monosachharide. Suitable disachharides may include, but are not limited to, lactose, maltose, isomaltose, trehalose, maltulose, and sucrose. Suitable oligosachharides may include, but are not limited to, raffinose and acarbose. Also included are the sachharides modified by additional substituents, for example, methyl glycosides, N-acetyl-glucosamine, N-acetyl-galactosamine and their de-acetylated forms.

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')$_2$, or Fab'). In addition, aggregates, polymers, and conjugates of immunoglobulins or their fragments may be used where appropriate so long as binding affinity for a particular molecule is substantially maintained.

As used herein, the term "chromophore" refers to a part of a molecule where the energy difference between two different molecular orbitals falls within the range of the visible spectrum. A chromophore may be responsible for a color of the molecule effected by absorbance of certain wavelengths of visible light and transmittance or reflectance of other wavelengths.

As used herein, the term "fluorophore" refers to a chemical compound, which when excited by exposure to a particular wavelength of light, emits light (at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers.

The invention includes a composition in one embodiment. The composition includes a first probe having a first initiator component bonded to the first probe. The composition further includes a second probe having a second initiator component bonded to the second probe. Both the first probe and the second probe are capable of binding to a single analyte. Furthermore, the first initiator component and the second initiator component are capable of forming an initiator when present in proximity to each other and when the first probe and the second probe are bonded to an analyte. In one embodiment, the composition may be used to detect one or more analyte in a sample.

As used herein, the term probe may refer to a chemical or a biological molecule that may selectively bond to an analyte. A suitable probe may be selected depending on the sample to be analyzed and the analytes available for detection in the sample. In one embodiment, an analyte to be detected may be essentially chemical in nature and both the first probe and the second probe may include a chemical molecule. In one embodiment, an analyte to be detected may be essentially biological in nature and both the first probe and the second probe may include a biological molecule. In one embodiment, an analyte to be detected may be essentially chemical in nature and at least one of the first probe or the second probe may include a biological molecule. In one embodiment, an analyte to be detected may be essentially biological in nature and at least one of the first probe or the second probe may include a chemical molecule.

In one embodiment, one or more probes may include a chemical molecule that may be capable of binding to an analyte of interest. A suitable chemical molecule may be organic or inorganic in nature. A suitable organic chemical probe may include an organic ligand capable of binding the target of interest. Suitable organic ligands may include one or more of porphyrin, acetylacetonate, ethylenediaminetetracetate (EDTA), pyridine, bipyridine, terpyridine, ethylenediamine, oxalate, and the like. A suitable inorganic chemical probe may include an inorganic ligand, a metal complex, a metal salt, a nanocrystal, a nanoparticle, or combinations thereof. Suitable inorganic ligands may include one or more of halide, azide, ammonia, triphenylphosphine, thiocyanate, isothiocyanate, and the like.

In one embodiment, one or more probes may include a biological molecule that may be capable of binding to an analyte of interest. A biological molecule may refer to a molecule obtained from a biological subject in vivo or in vitro. Suitable biological molecules may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, antigens, haptens, vitamins, and the like.

As noted hereinabove, both the first probe and the second probe may be capable of binding to a single analyte. In one embodiment, the first probe and the second probe may recognize and bind to different parts of the analyte. For example, an analyte may include a zinc cation capable of binding to a porphyrin-based first probe and the analyte may further include an EDTA ligand capable of forming a metal complex with a second probe. Similarly, an analyte may include a nucleic acid and the first probe may include an oligonucleotide sequence capable of binding to a complementary base sequence in the nucleic acid and the second probe may include a different oligonucleotide sequence capable of binding to a different base sequence in the nucleic acid. In one embodiment, the first probe and the second probe may recognize and bind to the analyte in a manner different from each other. For example an analyte may include a protein and the first probe may be capable of binding to one or more amino acids in the protein sequence while the second probe may be capable of binding to a secondary structure of the protein.

In one embodiment, the first probe and the second probe may be same as each other and may be capable of binding to different parts of the analyte. For example, an analyte may include a ligand and both the first probe and the second probe may include a receptor capable of binding to different parts of the analyte. Alternatively, an analyte may include a receptor and both the first probe and the second probe may include a ligand. In some embodiments, an analyte may include an antigen and both the first probe and the second probe may include an antibody or antibody fragment or vice versa. In some embodiments, an analyte may include a nucleic acid and both the first probe and the second probe may include complementary nucleic acids. In some embodiments, the analyte, the first probe and the second probe may include proteins capable of binding to each other. Alternatively, in one embodiment, the first probe and the second probe may be different from each other. For example, an analyte may include a nucleic acid, and a first probe may include a complementary nucleic acid while the second probe may include a nucleic-acid binding protein (such as, zinc fingers).

Binding between the probe and the analyte may be effected by non-covalent bond formation or covalent bond formation. Covalent bond formation may refer to chemical bond formation (reaction) between the analyte and the probe resulting from sharing of one or more electrons between two or more atoms (in the analyte and the probe). Non-covalent bond formation may refer to interactions between the probe and the analyte that are not covalent in nature. Suitable examples of non-covalent interactions may include one or more ionic interactions, hydrophobic bonding, dipole-dipole interactions, hydrogen bonding, Van der Waal interactions, or high affinity interactions (such as, biotin-avidin or biotin-streptavidin complexation). In some embodiments, the analyte and the probe may have areas on their surfaces or in cavities giving rise to specific recognition between the two resulting in non-covalent binding. In some embodiments, a probe may bind to an analyte based on the reciprocal fit of a portion of their molecular shapes.

In one embodiment, both the first probe and the second probe may be capable of binding to the analyte by covalent bond formation. In one embodiment, both the first probe and the second probe may be capable of binding to the analyte by non-covalent bond formation. In one embodiment, the first probe may be capable of binding to the analyte through covalent bond formation and the second probe may be capable of binding to the analyte through non-covalent bond formation. In one embodiment, the first probe may be capable of binding to the analyte through non-covalent bond formation and the second probe may be capable of binding to the analyte through covalent bond formation.

The first probe and the second probe may bind to the analyte in a specific manner. As used herein, the term "specific binding" may refer to the specific recognition of one of two different molecules for the other compared to substantially less recognition of other molecules. In some embodiments, the probe may bind to an analyte with sufficient specificity, that is, a probe may bind to an analyte with greater affinity than it does to any other molecule. In some embodiments, the probe may bind to other molecules, but the binding may be such that the non-specific binding may be at or near background levels. In some embodiments, the affinity of the probe for the analyte of interest may be in a range that is at least 2-fold, at least 5-fold, at least 10-fold, or more than its affinity for other molecules. In some embodiments, probes with the greatest differential affinity may be employed, although they may not be those with the greatest affinity for the analyte. In some embodiments, a probe molecule may have an intrinsic equilibrium association constant (KA) for the analyte no lower than about $10^5$ $M^{-1}$ under physiological conditions.

In one embodiment, the probes may be sequence- or structure-specific; wherein the sequence or structure of an analyte recognized and bound by the probe may be sufficiently unique to that analyte.

In one embodiment, the probe(s) may be structure-specific and may recognize a primary, secondary, or tertiary structure of an analyte. A primary structure of an analyte may include specification of its atomic composition and the chemical bonds connecting those atoms (including stereochemistry), for example, the type and nature of linear arrangement of amino acids in a protein. A secondary structure of an analyte may refer to the general three-dimensional form of segments of biomolecules, for example, for a protein a secondary structure may refer to the folding of the peptide "backbone" chain into various conformations that may result in distant amino acids being brought into proximity with each other. Suitable examples of secondary structures may include, but are not limited to, alpha helices, beta pleated sheets, or random coils. A tertiary structure of an analyte may be is its overall three dimensional structure. A quaternary structure of an analyte may be the structure formed by its noncovalent interaction with one or more other analytes or macromolecules (such as protein interactions). An example of a quaternary structure may be the structure formed by the four-globin protein subunits to make hemoglobin. A probe in accordance with the embodiments of the invention may be specific for any of the afore-mentioned structures.

An example of a structure-specific probe may include a protein-specific molecule that may bind to a protein analyte. Examples of suitable protein-specific molecules may include antibodies and antibody fragments, nucleic acids (for example, aptamers that recognize protein analytes), or protein substrates (non-catalyzable). In some embodiments, an analyte may include an antigen and the probe(s) may include an antibody. A suitable antibody may include monoclonal antibodies, polyclonal antibodies, multispecific antibodies (for example, bispecific antibodies), or antibody fragments so long as they bind specifically to an antigen analyte.

In one embodiment, the probes may be specific for a region of the analyte of interest. For example, the probe may be specific for a protein modification. Protein modifications may include post-translational modifications such as phosphorylation, glycosylation, ubiquitinylation, acetylation, and the like.

In one embodiment, a probe(s) may be sequence-specific. A sequence-specific probe may include a nucleic acid and the probe may be capable of recognizing a particular linear arrangement of nucleotides or derivatives thereof in the analyte. In some embodiments, the linear arrangement may include contiguous nucleotides or derivatives thereof that may each bind to a corresponding complementary nucleotide in the probe. In an alternate embodiment, the sequence may not be contiguous as there may be one, two, or more nucleotides that may not have corresponding complementary residues on the probe. Suitable examples of nucleic acid-based probes may include, but are not limited to, DNA or RNA oligonucleotides or polynucleotides. In some embodiments, suitable nucleic acids may include nucleic acid analogs, such as dioxygenin dCTP, biotin dcTP 7-azaguanosine, azidothymidine, inosine, or uridine.

In one embodiment, both the probe and the analyte may include nucleic acids. In one embodiment, a nucleic-acid based probe may form a Watson-Crick bond with the nucleic acid analyte. In another embodiment, the nucleic acid probe may form a Hoogsteen bond with the nucleic acid analyte, thereby forming a triplex. A nucleic acid probe that binds by Hoogsteen binding may enter the major groove of a nucleic acid analyte and hybridize with the bases located there. Suitable examples of the above probes may include molecules that recognize and bind to the minor and major grooves of nucleic acids (for example, some forms of antibiotics.) In certain embodiments, the nucleic acid probes may form both Watson-Crick and Hoogsteen bonds with the nucleic acid analyte (for example, bis PNA probes are capable of both Watson-Crick and Hoogsteen binding to a nucleic acid).

The length of nucleic acid probe may also determine the specificity of binding. The energetic cost of a single mismatch between the probe and the nucleic acid analyte may be relatively higher for shorter sequences than for longer ones. In some embodiments, hybridization of smaller nucleic acid probes may be more specific than the hybridization of longer nucleic acid probes, as the longer probes may be more amenable to mismatches and may continue to bind to the nucleic acid depending on the conditions. In certain embodiments, shorter probes may exhibit lower binding stability at a given temperature and salt concentration. In some embodiments, the nucleic acid probe may have a length in range of from about 4 nucleotides to about 12 nucleotides, from about 12 nucleotides to about 25 nucleotides, from about 25 nucleotides to about 50 nucleotides, from about 50 nucleotides to about 100 nucleotides, from about 100 nucleotides to about 250 nucleotides, from about 250 nucleotides to about 500 nucleotides, or from about 500 nucleotides to about 1000 nucleotides. In some embodiments, the nucleic acid probe may have a length in a range that is greater than about 1000 nucleotides. Notwithstanding the length of the nucleic acid probe, all the nucleotide residues of the probe may not hybridize to complementary nucleotides in the nucleic acid analyte. For example, the probe may include 50 nucleotide residues in length, and only 25 of those nucleotide residues may hybridize to the nucleic acid analyte. In some embodiments, the nucleotide residues that may hybridize may be contiguous with each other. The nucleic acid probes may be single stranded or may include a secondary structure.

Regardless of the type of probe(s) and the analyte, the specificity of binding between the probe(s) and the analyte may also depend on the binding conditions (for example, hybridization conditions in case of complementary nucleic acids). Suitable binding conditions may be realized by modulation of one or more of pH, temperature, probe concentration, or salt concentration.

In one embodiment, at least one of the first probe or the second probe may be capable of binding to the analyte through combination of one or more intermediatory probes. The combinations of probes may provide greater specificity or in certain embodiments amplification of the signal. Thus, in one embodiment, a composition may include additional probes that may be used to form a sandwich with the first probe, the second probe, or both. In one embodiment, at least one of the first probe or the second probe may be capable of binding to a corresponding primary probe, which in turn may be capable of binding to the analyte. The first probe (bonded to the first initiator component) or the second probe (bonded to the second initiator component) in this case may then be referred to as secondary probes. In one embodiment, at least one of the first probe or the second probe may be capable of binding to a corresponding secondary probe, which in turn may be capable of binding to a corresponding primary probe, which may be capable of binding to the analyte. The first probe or the second probe in this case may then be referred to as tertiary probes.

Suitable examples of probe combinations may include primary antibody-secondary antibody, complementary nucleic acids, or other ligand-receptor pairs (such as biotin-streptavidin). Some specific examples of suitable probe pairs may include mouse anti-myc for recombinant expressed proteins with c-myc epitope; mouse anti-HisG for recombinant protein with His-Tag epitope, mouse anti-xpress for recombinant protein with epitope-tag, rabbit anti-goat for goat IgG primary molecules, complementary nucleic acid sequence for a nucleic acid; mouse anti-thio for thioredoxin fusion proteins, rabbit anti-GFP for fusion protein, jacalin for α-D-galactose; and melibiose for carbohydrate-binding proteins, sugars, nickel couple matrix or heparin.

In some embodiments, a combination of a primary antibody and a secondary antibody may be used as a first probe or a second probe. A primary antibody may be capable of binding to a specific region of the analyte and the secondary antibody may be capable of binding to the primary antibody. A secondary antibody may be attached to an initiator before binding to the primary antibody or may be capable of binding to an initiator at a later step. In an alternate embodiment, a primary antibody and specific binding ligand-receptor pairs (such as biotin-streptavidin) may be used. The primary antibody may be attached to one member of the pair (for example biotin) and the other member (for example, streptavidin as a first probe or a second probe) may be bonded with an initiator. In some embodiments, initial signal amplification may be obtained when several secondary antibodies may bind to epitopes on the primary antibody.

Further signal amplification may be obtained by formation of an initiator from the first initiator component and the second initiator component and initiating a polymerization reaction using the initiator. As noted hereinabove, the first initiator component and the second initiator component may be capable of forming an initiator when the initiator components may be present proximate to each other, for example, when the first probe and the second probe are bonded to the analyte. An initiator may refer to one or more molecules capable of initiating a polymerization reaction. In one embodiment, depending upon the type of polymerization reaction, an initiator may include a single molecule. In one embodiment, depending upon the type of polymerization reaction, an initiator may include a combination of molecules that may together provide for initiation of the polymerization reaction.

In one embodiment, the first initiator component and the second initiator component may be independently inactive if not present in proximity to each other. Inactive initiator component, as used herein, may refer to a chemical moiety that may be incapable of initiating a polymerization reaction. In one embodiment, the first initiator component and the second initiator component may form an initiator when present in proximity to each other. In one embodiment, the first initiator component and the second initiator component may form one of the initiator molecules (if two or more initiator molecules in combination form an initiator) when present in proximity to each other. In one embodiment, the first initiator component and the second initiator component may react or interact when present in proximity to each other to form a chemical moiety that may be capable of forming an active initiator. For example, a first initiator component and a second initiator component may form a ligand that may be capable of binding to a metal to form a metal-ligand catalyst that may be capable of initiating a polymerization reaction independently or in combination with other initiating molecules.

In one embodiment, one of the first initiator component or a second initiator component may include a blocked initiator and the other initiator component may provide to unblock or activate the blocked initiator. Blocked initiator, as used herein, may refer to an initiating molecule that may include protective functional groups, which may inhibit its initiating capabilities. In one embodiment, a first initiator component may include a protective functional group that may hinder its initiating properties. A second initiator component, when present in proximity to the first initiator component may be capable of unblocking the first initiator component by modifying or removing the protective functional group. Modification or removal of the protective functional group may result in an active initiator molecule capable of initiating a polymerization reaction independently or in combination with other initiating molecules.

Figure 1:
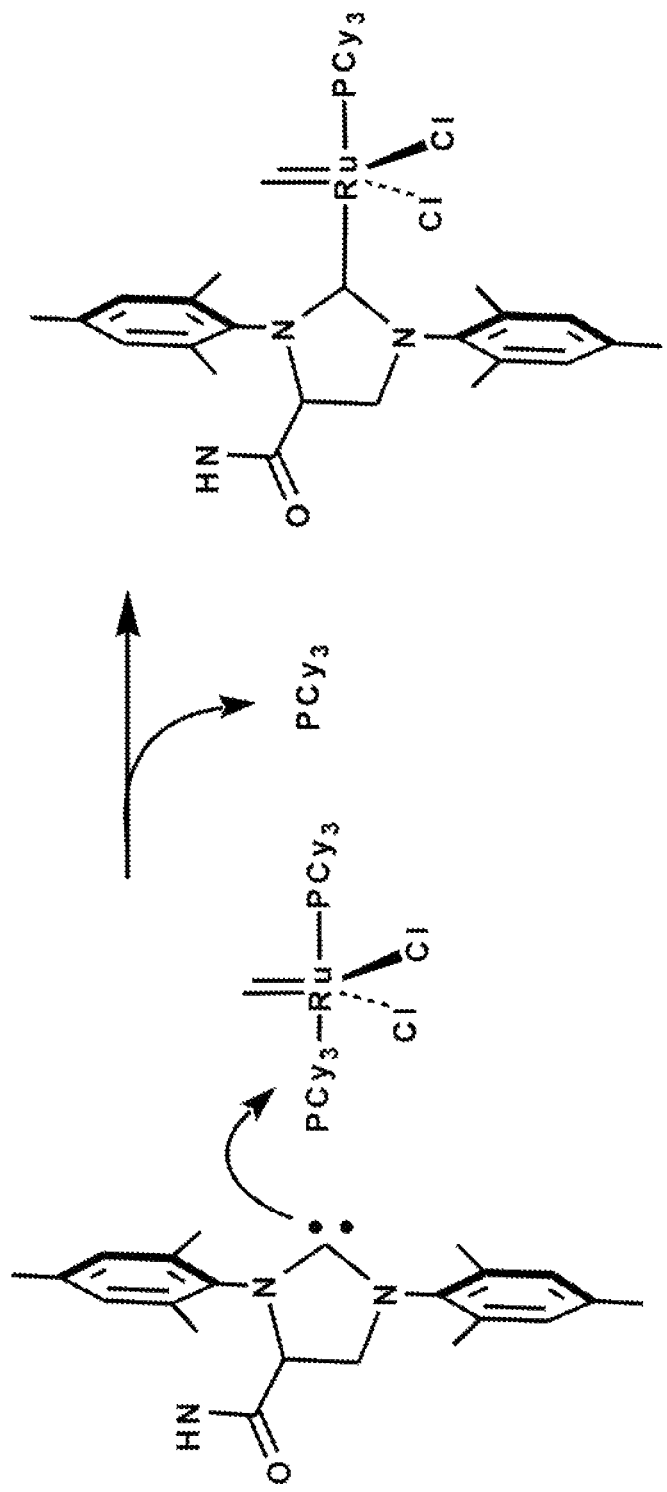
FIG. 1 is a schematic illustration of an activatable initiator in accordance with one embodiment of the invention.
Figure 2:
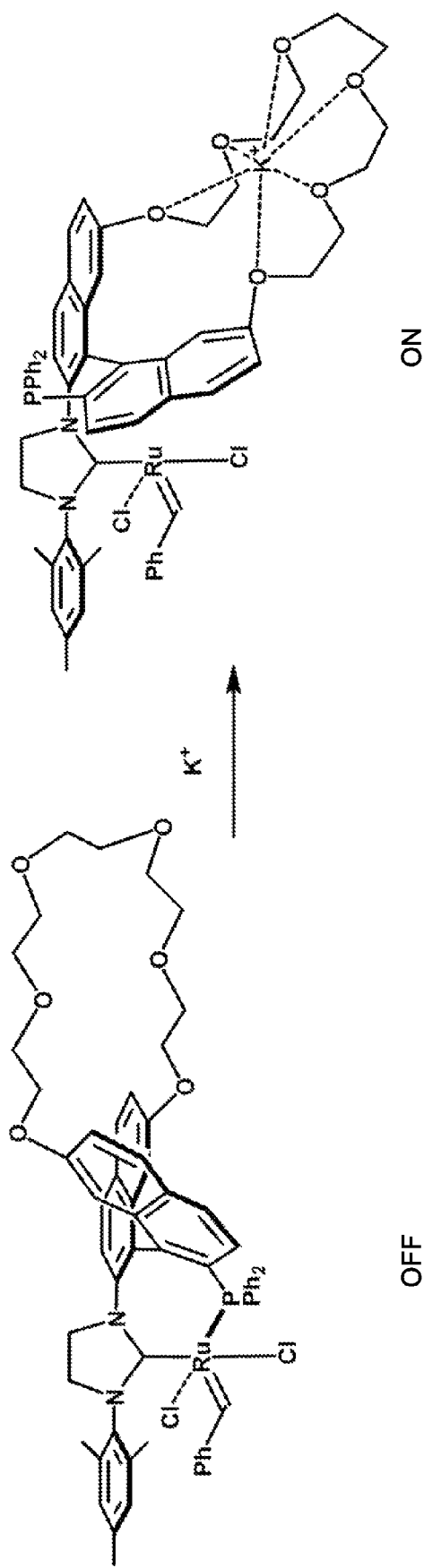
FIG. 2 is a schematic illustration of an activatable initiator in accordance with one embodiment of the invention.
Figure 4:
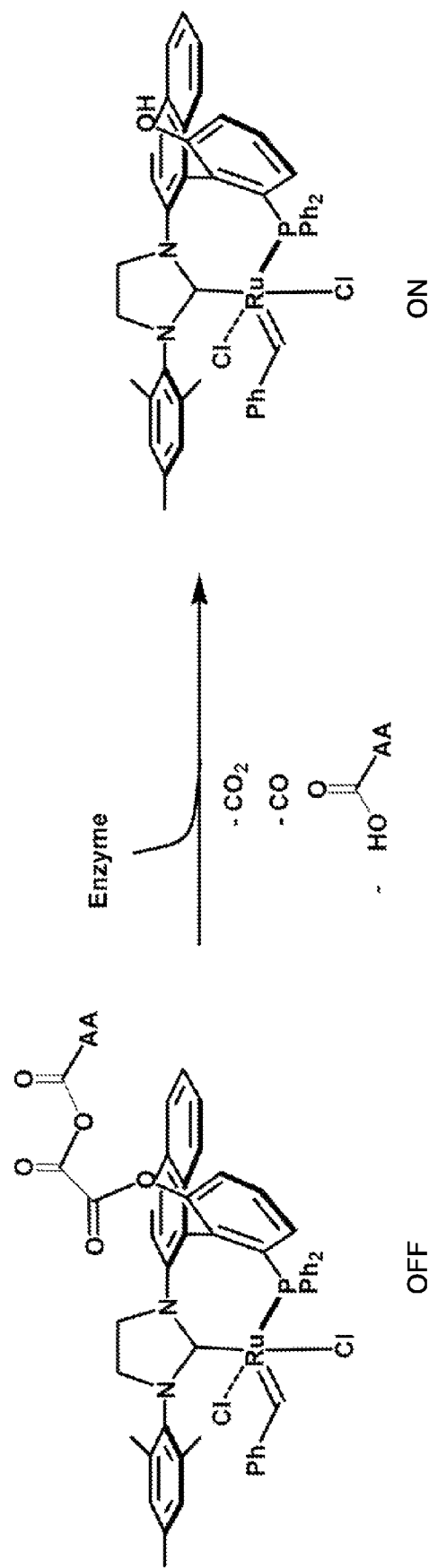
FIG. 4 is a schematic illustration of an activatable initiator in accordance with one embodiment of the invention.

FIG. 1 shows an example of two initiator components forming a metal catalyst when present in proximity to each other. FIG. 2 shows an example of an inactive initiator that may be activated by contacting with a potassium cation. In one embodiment, the first initiator component may include an inactive initiator and the second initiator component may include a potassium cation source. FIG. 3 shows an example of an inactive initiator that may be activated by contacting with a nitroreductase. In one embodiment, the first initiator component may include an inactive initiator and the second initiator component may include a nitroreductase. FIG. 4 shows an example of a blocked initiator that may be activated by contacting with an enzyme and decarboxylation reaction. In one embodiment, the first initiator component may include a blocked initiator and the second initiator component may include an enzyme.

In one embodiment, a probe and an initiator component may be bonded to each other directly (that is without any linkers). In one embodiment, a probe and an initiator component may be bonded to each other via a linker. A linker may include a form of linking structure or sequence formed due to the non-covalent or covalent bond formation. Non-covalent interactions may include, but are not limited to, hydrophobic interactions, ionic interactions, hydrogen-bond interactions, high affinity interactions (such as, biotin-avidin or biotin-streptavidin complexation), or other affinity interactions. The nature of the binding may be such that it does not substantially impair the effectiveness of either entity (for example, binding mechanism should not affect the initiator component efficiency or analyte-binding capability of the probe).

In one embodiment, an initiator component may include a functional group capable of binding to the probe. Correspondingly, at least one of the first probe or the second probe may include a complementary functional group capable of reacting with the functional group in the initiator component. Suitable examples of functional group combinations may include, but are not limited to, amine ester and amines or anilines; acyl azide and amines or anilines; acyl halides and amines, anilines, alcohols, or phenols; acyl nitrile and alcohols or phenols; aldehyde and amines or anilines; alkyl halide and amines, anilines, alcohols, phenols or thiols; alkyl sulfonate and thiols, alcohols or phenols; anhydride and alcohols, phenols, amines or anilines; aryl halide and thiols; aziridine and thiols or thioethers; carboxylic acid and amines, anilines, alcohols or alkyl halides; diazoalkane and carboxylic acids; epoxide and thiols; haloacetamide and thiols; halotriazin and amines, anilines or phenols; hydrazine and aldehydes or ketones; hydroxyamine and aldehydes or ketones; imido ester and amines or anilines; isocyanate and amines or anilines; and isothiocyanate and amines or anilines. A functional group in one of the aforementioned functional group pair may be present in an initiator component and a corresponding functional group may be present in the probe. For example, an initiator component may include a carboxylic acid and the probe may include an amine, aniline, alcohol or acyl halide, or vice versa. Conjugation between the initiator component and the probe may be effected in this case by formation of an amide or an ester linkage. In one embodiment, linkage between the initiator component and the probe may be affected using ligand-receptor pairs, for example, biotin-streptavidin. A probe may be bonded to a biotin, an initiator component may be bonded to a streptavidin, and the probe-initiator component binding may be provided by biotin-streptavidin pair formation.

A suitable functional group may be included in the initiator component by modification of existing initiator components or synthesis of new initiator components. In one embodiment, at least one of the first initiator component or the second initiator component may include a modified ATRP initiator component. In one embodiment, at least one of the first initiator component or the second initiator component may include a modified ROMP initiator component.

In one embodiment, an initiator formed from the first initiator component and the second initiator component may be capable of initiating a step-growth polymerization reaction or an addition polymerization reaction. In one embodiment, an initiator formed from the first initiator component and the second initiator component may be capable of initiating a free-radical polymerization reaction, an anionic polymerization reaction, a cationic polymerization reaction, a coordination polymerization, a ring-opening polymerization, a metathesis polymerization, a condensation polymerization, or combinations of two more of the foregoing.

An initiator may be further characterized by the mechanism of the initiation and the polymerization reaction type. In one embodiment, the initiator may be capable of initiating a controlled polymerization reaction. As used herein, controlled polymerization reaction refers to a polymerization reaction that may allow for control of the molecular weight and polydispersity index of the polymer produced. In one embodiment, a controlled polymerization reaction includes one more of the following characteristics: linear dependence of the degree of polymerization as a function of time; linear dependence of the number-average molecular weight (Mn) on the extent of polymerization; control over the molecular weight of the polymer by varying the polymer precursor to initiator ratio, a polydispersity index (PDI) in a range that is less than about 2.0; chain-breaking reactions insignificant compared to chain propagation reactions; complete conversion of polymer precursor to polymer with the ability to continue polymerization upon addition of more polymer precursor; the ability to make block copolymers by sequential polymer precursor addition; or ability to produce chain-end functionalized polymers in high yield.

In one embodiment, controlled polymerization reaction types may include one or more of: atom transfer radical polymerization (ATRP), group transfer polymerization (GTP), nitroxide mediated polymerization (NMP), reversible addition-fragmentation transfer (RAFT), or ring opening metathesis polymerization (ROMP). In one embodiment, controlled polymerization reaction types may include one or more of: degenerative transfer (DT), anionic polymerization, cationic polymerization, coordination polymerization, acyclic diene metathesis polymerization (ADMET), or other polymerization reactions involving stable free radicals (SFR).

In one embodiment, the initiator may be capable of initiating an atom transfer radical polymerization (ATRP) type. In one embodiment, the initiator may be capable of initiating a ring opening metathesis polymerization (ROMP) type. In one embodiment, the initiator may capable of initiating a group transfer polymerization (GTP) type. In one embodiment, the initiator may be capable of initiating a nitroxide-mediated polymerization type (NMP). In one embodiment, the initiator may be capable of initiating a reversible addition fragmentation chain transfer polymerization type (RAFT).

In one embodiment, an initiator may include an initiating molecule, for example, peroxide used in free radical polymerization. In one embodiment, an initiator may include an initiating molecule and a catalyst, for example, an alkyl halide and copper halide-bipyridine-based catalyst used in atom transfer radical polymerization (ATRP). In one embodiment, an initiator may include a catalyst, for example, metal alkylidine catalysts used in ring opening metathesis polymerization (ROMP). In one embodiment, the first initiator component and the second initiator component may be capable of forming a free radical initiator when present in proximity to each other. In one embodiment, the first initiator component and the second initiator component may be capable of forming an alkyl halide when present in proximity to each other that may be used in combination with a catalyst to provide an ATRP initiator. In one embodiment, the first initiator component and the second initiator component may be capable of forming a metal-ligand complex when present in proximity to each other that may provide a ROMP initiator. In one embodiment, the first initiator component and the second initiator component may be capable of forming a ligand when present in proximity to each other that may be used in combination with a metal to provide a ROMP initiator.

The type of initiator suitable for the invention may depend on the details of the polymerization reaction, including the mechanism for polymerization, the types of polymer precursors being used, the molecular weights desired, the solvent system and the reaction conditions. In some embodiments, an initiator may be an initiator for polymerization by a free radical mechanism, such as ATRP, NMP, DT, RAFT or a related mechanism involving stable free radicals. Suitable initiators for free radical polymerization may include reagents or combinations of reagents that may be capable of producing free radicals. In some embodiments, the initiator may be an initiator for polymerization by an ionic mechanism, such as cationic or anionic polymerization. In some embodiments, the initiator may be a reagent for producing metal-alkylidene catalysts for olefin metathesis such as in ROMP or ADMET.

In one embodiment, an initiator may include a free radical initiator. Initiating radicals for free radical polymerization processes may be generated by any suitable method, such as the thermally induced homolytic scission of a suitable compound(s) (thermal initiators such as peroxides, peroxyesters, or azo compounds), the spontaneous generation from monomer (for example. styrene), redox initiating systems, photochemical initiating systems, or systems responsive to high energy radiation such as electron beam, X- or gamma-radiation. Thermal initiators may be chosen to have an appropriate half-life at the temperature of polymerization. These initiators may include one or more of the following compounds: 2,2'-azobis(isobutyronitrile) ("AIBN"), 2,2'-azobis(2-cyano-2-butane), dimethyl 2,2' 20 azobisdimethylisobutyrate, 4,4'-azobis(4-cyanopentanoic acid), 1,1' azobis(cyclohexanecarbonitrile), 2-(t-butylazo)-2-cyanopropane, 2,2'-azobis[2-methyl-N (1,1)-bis(hydroxymethyl)-2-hydroxyethyl] propionamide, 2,2'-azobis[2-methyl-N hydroxyethyl)]-propionamide, 2,2'-azobis(N,N'-dimethyleneisobutyramidine)dihydrochloride, 2,2'-azobis (2-amidopropane)dihydrochloride, 2,2'-azobis(N,N' dimethyleneisobutyramide), 2,2'-azobis(2-methyl-N-[1,1-bis(hydroxymethyl)-2 hydroxyethyl]propionamide), 2,2'-azobis(2-methyl-N-[1,1-bis(hydroxymethyl)ethyl]propionamide), 2,2'-[2-methyl-N-(2-hydroxyethyl) propionamide], 2,2' azobis(isobutyramide)dihydrate, 2,2'-azobis(2,2,4-trimethylpentane), 2,2'-azobis (2 methylpropane), t-butyl peroxyacetate, t-butyl peroxybenzoate, t-butyl peroxyoctoate, t-butyl peroxyneodecanoate, t-butylperoxy isobutyrate, t-amyl peroxypivalate, t-butyl peroxypivalate, all-isopropyl peroxydicarbonate, dicyclohexyl peroxydicarbonate, dicumyl-peroxide, dibenzoyl peroxide, dilauroyl peroxide, potassium peroxydisulfate, ammonium peroxydisulfate, di-t-butyl hyponitrite, or dicumyl hyponitrite. Suitable examples of photochemical initiators may include benzoin derivatives, benzophenone, acyl phosphine oxides, and photo-redox systems. Suitable examples of redox initiators may include oxidants, such as potassium peroxydisulfate, hydrogen peroxide, t-butyl hydroperoxide, or reductants, such as iron (II), titanium (III), potassium thiosulfite, potassium bisulfite, or combinations thereof.

In one embodiment, an initiator may include an ATRP initiator. An ATRP initiator may include a combination of an alkyl halide and a transition metal complex (metal ligand complex). The transition metal complex may participate in a redox cycle with the initiator and dormant polymer chain, but may not form a direct carbon-metal bond with the polymer chain. The transition metal complex may be selected from the group consisting of Cu(I)/Cu(II), Fe(II)/Fe(III); Ru(II)/Ru (III), Cr(II)/Cr(III); Mo(0)/Mo(I); Mo(II)/Mo(III); W(II)/W (III); Rh(III)/Rh(IV); Co(I)/Co(II), Re(II)/Re(III); Ni(0)/Ni (I); Mn(III)/Mn(IV); V(II)/V(III); Zn(I)/Zn(II); Au(I)/Au(II); and Ag(I)/Ag(II). Suitable examples of ligands may include bipyridines, alkyl-substituted bipyridine derivatives, alkylpyridine imines (for example N-(propyl)-2 25 pyridylmethanimine), triamines, tetraamines (for example N,N,N',N'',N''-pentamethyldiethylenetriamine and tris(2-(dimethylamino) ethyl(amine)). In one embodiment, an initiator may be capable of initiating a direct ATRP reaction type. In one embodiment, an initiator may be capable of initiating an indirect ATRP reaction type. An indirect ATRP initiator may include a free radical initiator and metal halide ligand complex. In one embodiment, an initiator may include an alkyl bromide and CuCl complex. A CuCl complex may include a bipyridine ligand or a tris(2-(dimethylamino) ethyl(amine)) ligand.

In one embodiment, an initiator may include a ROMP initiator. A ROMP initiator may include a metal alkylidene catalyst. In one embodiment, a ROMP initiator may include one or more molecules having formula (I) to (VI), or derivatives thereof.

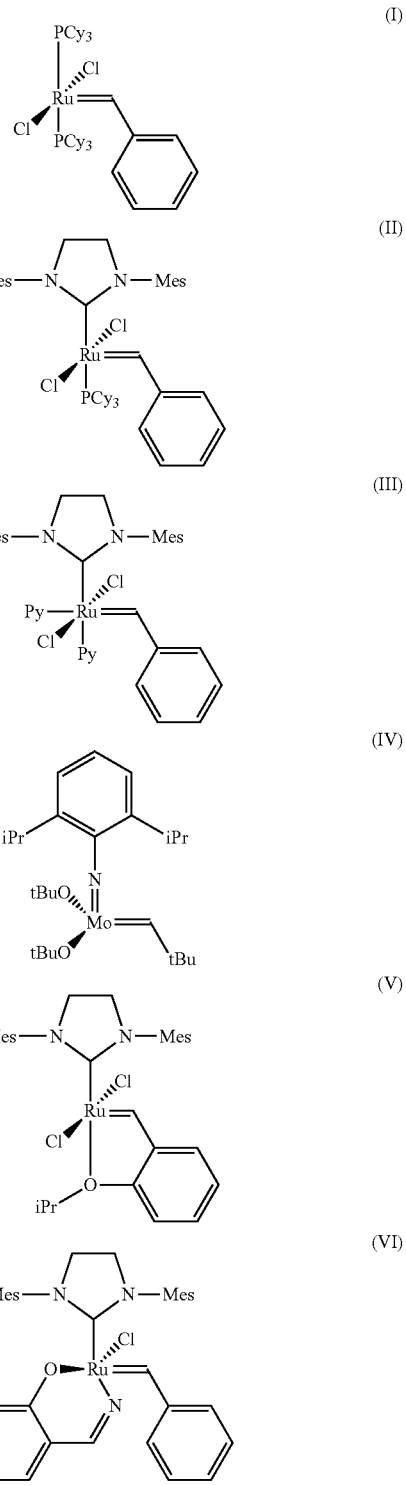

In one embodiment, an initiator may include a NMP initiator. NMP initiators may include a free radical initiator (optional) and a nitroxide source. In some embodiments, the nitroxide source may also provide for free radical initiation (for example, an alkoxy amine). A suitable nitroxide source may include one or more of alkoxyamines, TEMPO (i.e., 2,2,6,6-tetramethylpiperidinyl-1-oxy), reaction products of nitrones, or reaction products of nitric oxides.

In one embodiment, an initiator may include a RAFT initiator. A RAFT initiator may include a free radical initiator and a control agent. A suitable RAFT control agent may include one or more of dithiocarbonates, dithioesters, xanthates, or dithioacylhydrazones.

Some other examples of ATRP initiators may include structures having formulae (VII) to (X).

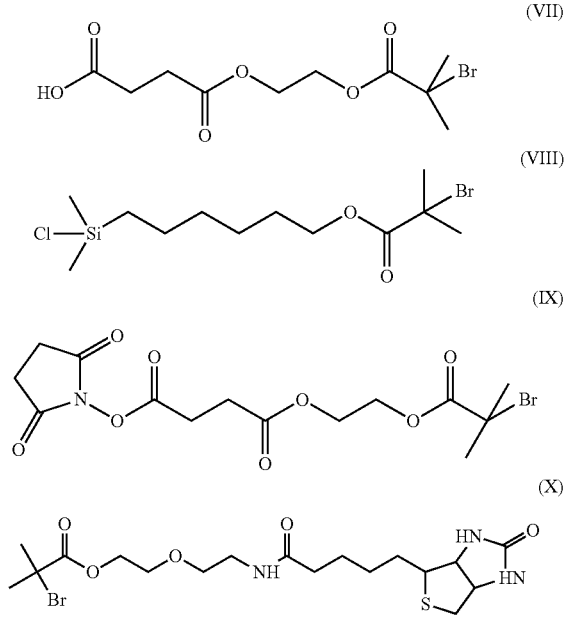

One or more of the aforementioned molecules may be used in combination with a metal ligand complex as an ATRP initiator. Some other examples of ROMP initiators may include structures having formulae (XI) and (XII), wherein PEG550 represents a polyethylene glycol chain having a molecular weight of 550 grams per mole.

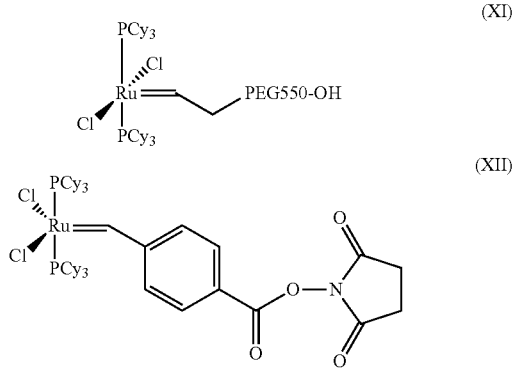

In one embodiment, an initiator component or an initiator may be chosen such that under the reaction conditions there is no substantial adverse interaction of the initiator with other polymer precursors or reagents under the conditions of the polymerization. Furthermore, an initiator component may be chosen such that the initiator component may not affect the binding between the analyte and the probes. The initiator component or the initiator may also have the requisite solubility in the reaction medium or polymer precursor mixture.

Figure 5:
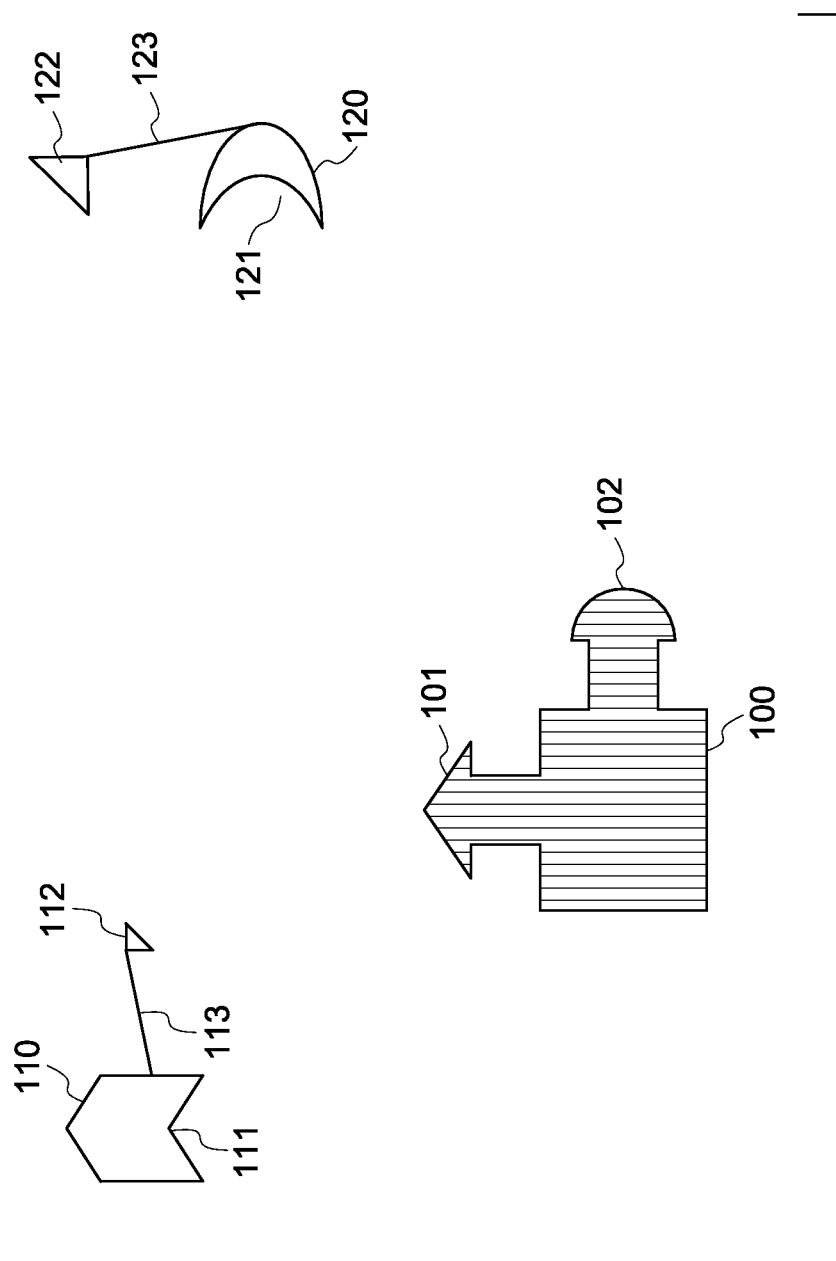
FIG. 5 is a schematic illustration of a composition in accordance with one embodiment of the invention.
Figure 6:
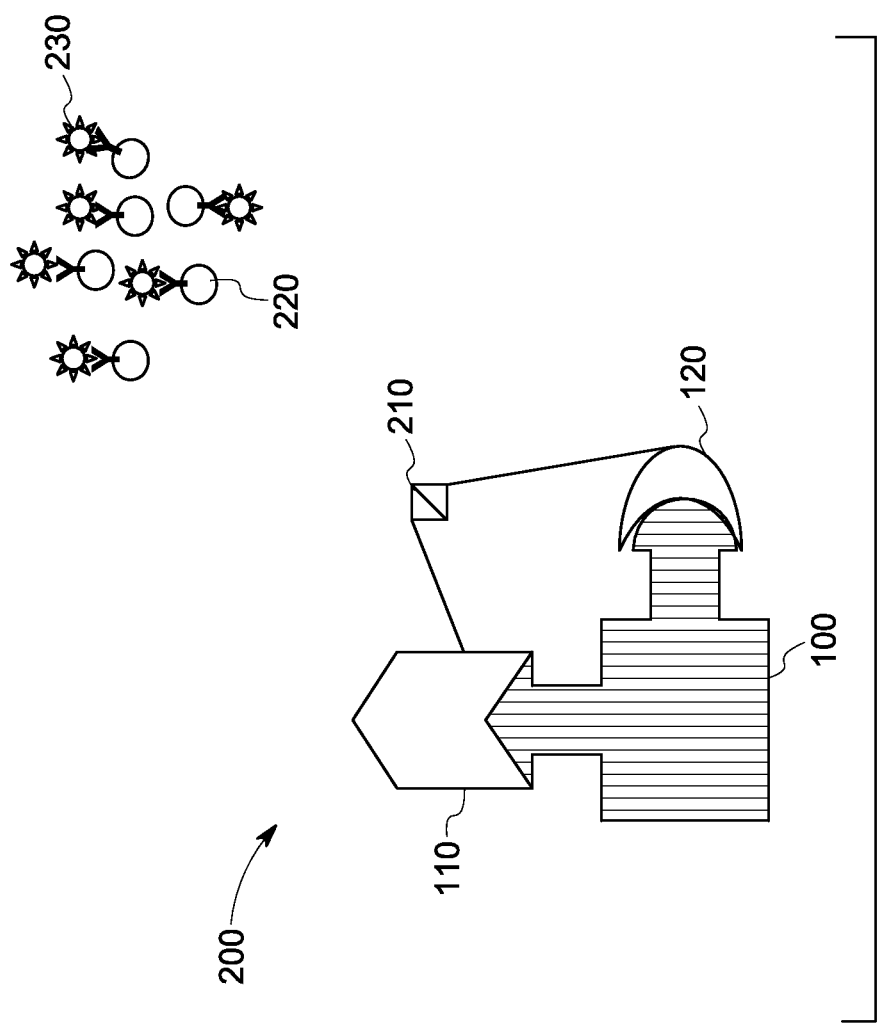
FIG. 6 is a schematic illustration of a composition in accordance with one embodiment of the invention.
Figure 7:
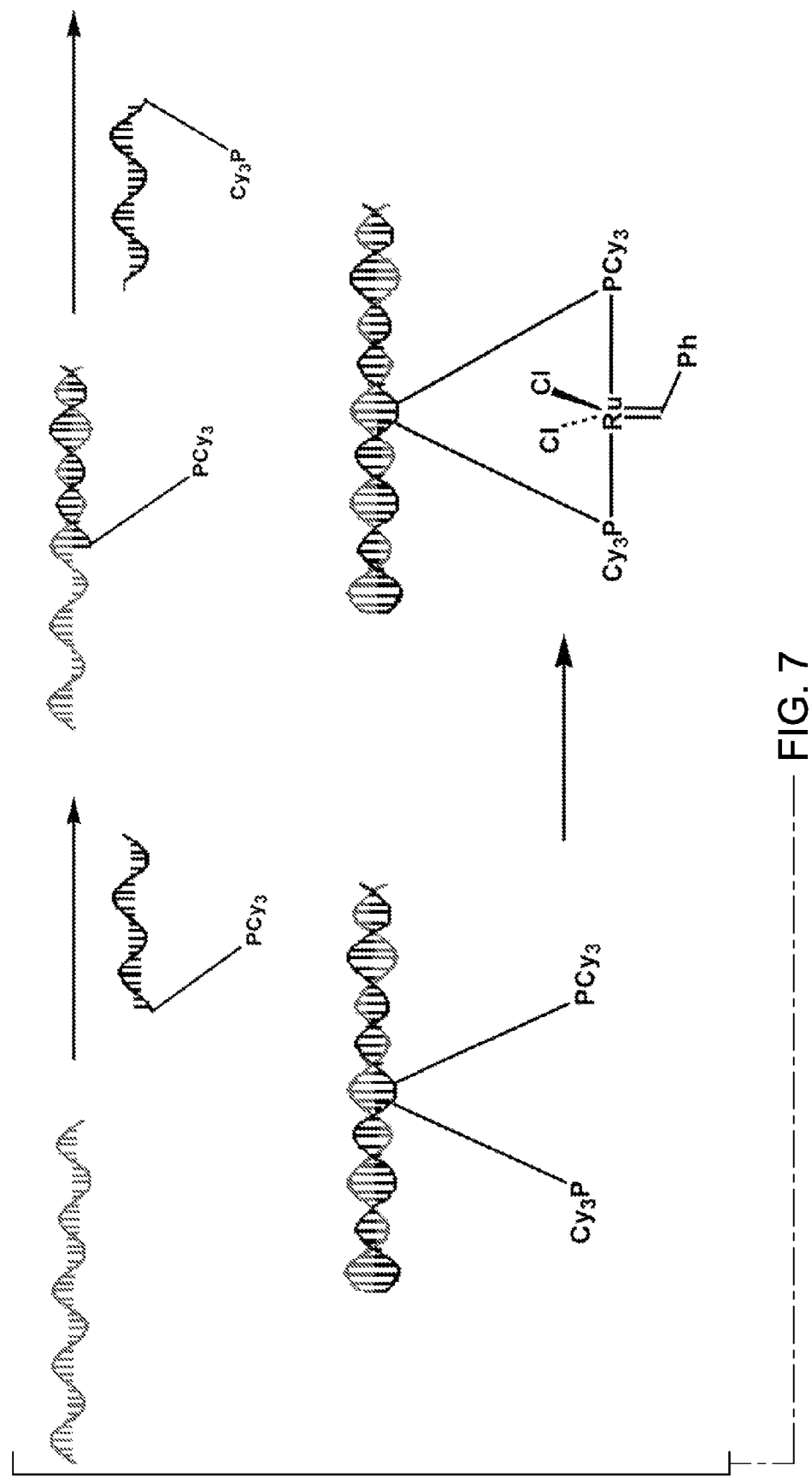
FIG. 7 is a schematic illustration of a composition in accordance with one embodiment of the invention.
Figure 8:
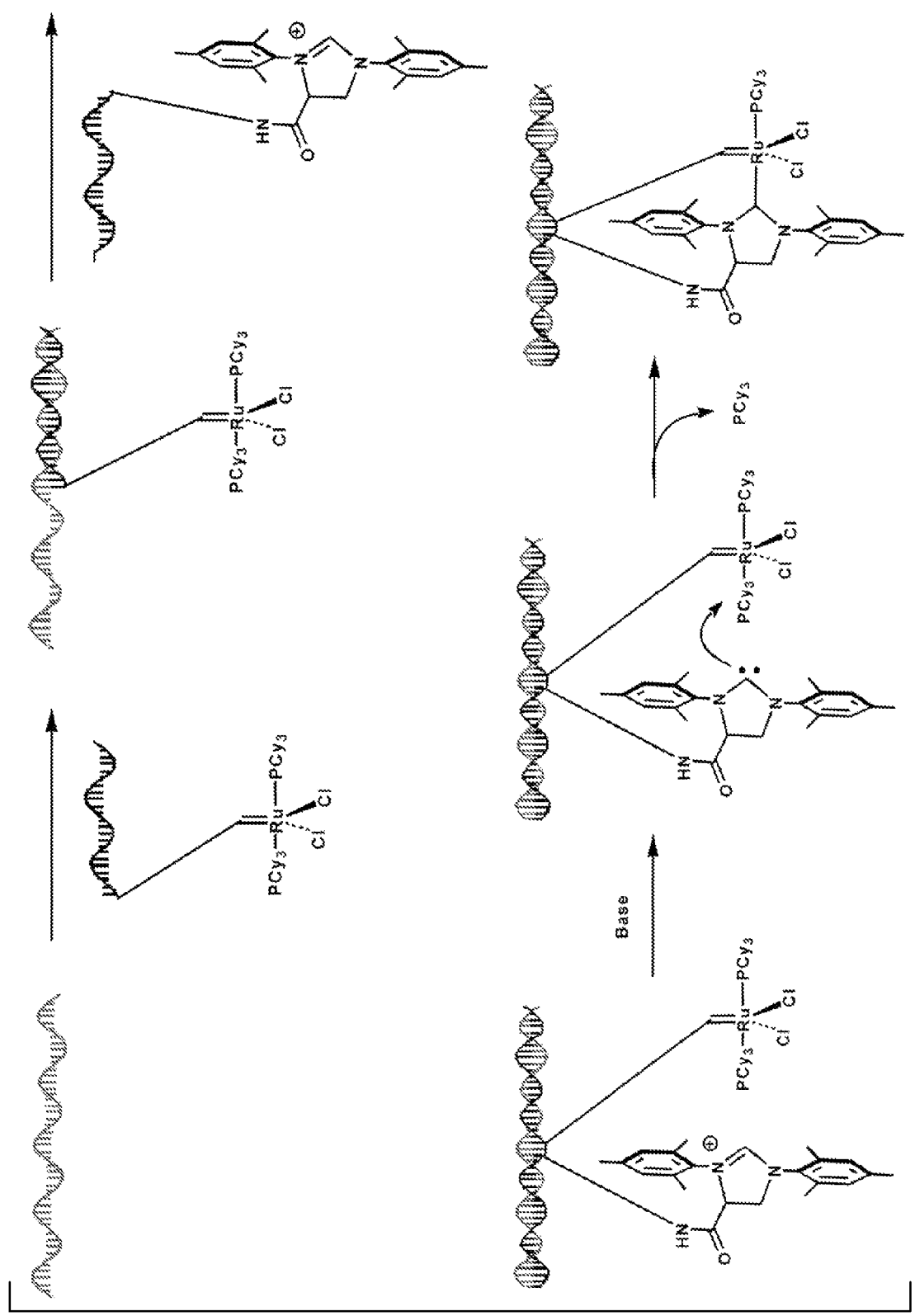
FIG. 8 is a schematic illustration of a composition in accordance with one embodiment of the invention.

In one embodiment, the composition further includes an analyte. In one embodiment, both the first probe and the second probe are bonded to the analyte. FIG. 5 illustrates a schematic example of a composition in accordance with one embodiment of the invention. The composition includes an analyte 100 having a first probe-specific binding site 101 and a second probe-specific binding site 102. The composition includes a first probe 110 having an analyte-specific binding site 111. The first probe also includes a first initiator component 112 bonded to the first probe via a linking structure 113. The composition further includes a second probe 120 having an analyte-specific binding site 121. The second probe includes a second initiator component 122 bonded to the second probe via a linking structure 123. FIG. 6 illustrates a schematic example of a complex 200 in accordance with one embodiment of the invention. The complex includes an analyte 100 bonded to a first probe 110 via specific binding sites 101 and 111 and bonded to the second probe via specific binding sites 102 and 121. The first initiator component and the second initiator together form an initiator 210. FIGS. 7 and 8 illustrate one embodiment of the invention in which a ruthenium-alkylidene based ROMP catalyst may be formed when the two nucleic acid probes are bonded to a nucleic acid analyte and when the two initiator components are present in proximity to each other In one embodiment, the analyte may be a portion of a sample to be analyzed. Suitable samples that may be analyzed using the compositions disclosed herein may include soil samples, air samples, water samples, plant samples, food samples, or biological samples. "Biological sample" as used herein, may refer to a sample obtained from a biological subject in vivo or in vitro. In some embodiments, a biological sample may be of an eukaryotic origin, for example, insects, protozoa, birds, fish, reptiles, and in another embodiment of a mammalian origin, for example, rat, mouse, cow, dog, donkey, guinea pig, or rabbit, and in another embodiment of a primate origin, for example, chimpanzees or humans. Suitable examples of biological samples may include cultures, blood, plasma, serum, saliva, cerebral spinal fluid, pleural fluid, milk, lymph, sputum, semen, urine, stool, tears, saliva, needle aspirates, external sections of the skin, respiratory, intestinal, and genitourinary tracts, tumors, organs, cell cultures or cell culture constituents, or solid tissue sections. Biological samples also may include extracts from a biological sample, for example, an antigen from a biological fluid, such as blood.

A sample may include any of the aforementioned samples regardless of their physical condition, such as, but not limited to, being frozen or stained or otherwise treated. In some embodiments, a sample may include compounds which are not naturally intermixed with the sample in nature such as preservatives, anticoagulants, buffers, fixatives, nutrients, antibiotics, solvents, or the like. In one embodiment, the sample may be immobilized on a solid support, such as, blots, assays, arrays, glass slides, nanoparticles, beads, microtiter, ELISA plates, or any other substrate.

In some embodiments, the sample may be analyzed as is, that is, without harvest and/or isolation of the analyte of interest. In an alternate embodiment, harvest and isolation of analytes may be performed prior to analysis. An analyte according to an embodiment of the invention may be present on the surface of a sample (for example, an antigen on a surface of a tissue section) or present in the bulk of the sample (for example, an antibody in a buffer solution). In some embodiments, an analyte may not be inherently present on the surface of a sample and the sample may have to be processed to make the analyte available on the surface. In one embodiment, a sample may not be required and the analyte may be analyzed directly or the analyte may be directly immobilized on a substrate during analysis.

Suitability of analyte (s) to be analyzed may be determined by the type and nature of analysis required for the sample. In one embodiment, the analysis may provide information about the presence or absence of an analyte in the sample. For example, the analysis may provide information about the presence or absence of a germ in a suspected infected air sample. In another embodiment, an analysis may provide information on a state of a sample. For example, if the sample includes a drinking water sample, the analysis may provide information about the concentration of bacteria in the sample and thus the potability of the sample. Similarly, if the sample includes a tissue sample, the methods disclosed herein may be used to detect analyte(s) that may help in comparing different types of cells or tissues, comparing different developmental stages, detecting the presence of a disease or abnormality, determining the type of disease abnormality or investigating the interactions between multiple analytes and pathways.

An analyte may be living or nonliving in nature. In one embodiment, an analyte may include a pollutant. Suitable pollutants may include one or more of air pollutants, soil pollutants, or water pollutants. Air pollutants may include one or more of carbon monoxide, sulfur dioxide, chlorofluorocarbon, or nitrogen dioxide. Suitable soil pollutants may include one or more of hydrocarbons, heavy metals, herbicides, pesticides, or chlorinated hydrocarbons. Suitable water pollutants may include one or more heavy metals, fertilizers, herbicides, insecticides, or pathogens. In one embodiment, an analyte may include one or more of phosphate, molybdate, magnesium, sulfite, or calcium, which may provide information about a water or soil sample, for example, hardness of a water sample.

In one embodiment, an analyte may include one or more spoilage indicators associated with meat by-product. Suitable meats may include beef, lamb, pork, chicken, and the like. Spoilage indicators may include one or more biogenic diamines, or histamine, that is formed by the biological activity of bacteria in contact with meat. The spoilage factor, and diamine content, may be directly linked to the bacterial content of spoiled meat. In one embodiment, an analyte may provide information regarding the decarboxylation of free amino acids in the meat by enzymes released by spoilage microorganisms. Two of these products, putrescence and cadaverine, may have a distinctive odor and the odor concentration may correlate with surface bacteria counts. The surface bacteria count may be used to evaluate meat freshness.

In one embodiment, an analyte may include a chemical warfare agent. Suitable chemical warfare agents may include one or more incapacitating agents, lachrymators, vesicants or blister agents, nerve agents, pulmonary agents, blood agents, or malodorants.

Suitable incapacitating agents may include nervous system affecters, vomiting agents, choking agents, hallucinogens, sedatives, narcotics, depressants, and the like, and combinations of two or more thereof. In one embodiment, an incapacitating agent may include 3-quinuclidinyl benzilate (QNB, BZ), which may be an anticholinergic agent that may react with a probe comprising, for example, choline. Alternative nervous system affecters may include commercially available over the counter (OTC) or prescription pharmaceutical compositions. In one embodiment, an incapacitating agent may include curare, or a curare analog or derivative.

Suitable lachrymators may include one or more of o-chlorobenzylmalonitrile, chloromethyl chloroformate, stannic chloride, sym-dichloromethyl ether, benzyl bromide, xylyl bromide, methyl chlorosulphonate, ethyl iodoacetate, bromacetone, bromomethyl-ethyl ketone, acrolein (2-propanal), capsaicin including analogs and derivatives, or the like.

A suitable vesicant may include one or more of sulfur mustard, nitrogen mustard, or an arsenical such as Lewisite. Suitable sulfur mustard may include one or more of 2-chloroethyl chloromethyl sulfide, bis(2-chloroethyl)sulfide or dichloroethyl disulfide, his (2-chloroethylthio)methane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, his (2-chloroethylthiomethyl) ether, or his (2-chloroethyl thioethyl)ether. Suitable nitrogen mustard may include one or more of his (2-chloroethyl)ethylamine, his (2-chloroethyl)methylamine, or tris(2-chloroethyl)amine. Suitable Lewisites may include one or more of 2-chlorovinyl dichloroarsine, or his (2-chlorovinyl)chloroarsine, tris(2-chlorovinyl)arsine.

Suitable nerve agents may include cholinesterase inhibitors. In one embodiment, a cholinesterase inhibitor may include one or more of o-alkyl (Me, Et, n-Pr or i-Pr)-phosphonofluoridates, such as o-isopropyl methylphosphonofluoridate (sarin) or o-pinacolyl methylphosphonofluoridate (soman); o-alkyl N,N-dialkyl (Me, Et, n-Pr or i-Pr) phosphoramidocyanidates, such as o-ethyl N,N-dimethyl phosphoramidocyanidate (tabun); or o-alkyl S-2-dialkyl (Me, Et, n-Pr or i-Pr)-aminoethyl alkyl (Me, Et, n-Pr or i-Pr) phosphonothiolates and corresponding alkylated or protonated salts, such as o-ethyl S-2-diisopropylaminoethyl methyl phosphonothiolate.

Suitable pulmonary agents may include one or both of phosgene (carbonyl chloride) and perfluororoisobutylene. Suitable chemical toxins may include one or more of palytoxin, ricin, saxitoxin, or botulinum toxin.

Suitable blood agents may include forms of cyanide such as salts, and analogs and derivatives of cyanide salts. A suitable solid salt of cyanide may include sodium, potassium, and/or calcium. A suitable volatile liquid form of cyanide may include hydrogen cyanide and/or cyanogen chloride.

In one embodiment, an analyte may include one or more biological agents. Suitable biological agents may include pathogens, toxins, or combinations thereof. Biological agents may include prions, microorganisms (viruses, bacteria and fungi) and some unicellular and multicellular eukaryotes (for example parasites) and their associated toxins. Pathogens are infectious agents that may cause disease or illness to their host (animal or plant). Pathogens may include one or more of bacteria, viruses, protozoa, fungi, parasites, or prions.

Some examples of bacterial biological agents (and the diseases or effect caused by them) may include one or more of: *escherichia coli* (peritonitis, food poisoning); *mycobacterium tuberculosis* (tuberculosis); *bacillus anthracis* (anthrax); *salmonella* (food poisoning); *staphylococcus aureus* (toxic shock syndrome); *streptococcus pneumoniae* (pneumonia); *streptococcus pyogenes* (strep throat); *helicobacter pylori* (stomach ulcers); or *francisella tularensis* (tularemia).

Some examples of viruses (and the diseases or effect caused by them) may include one or more of hepatitis A, B, C, D and E (liver disease); influenza virus (flu, Avian flu); SARS coronavirus (severe acute respiratory syndrome); herpes simplex virus (herpes); molluscum contagiosum (rash); or human immunodeficiency virus (AIDS).

Some examples of protozoa (and the diseases or effect caused by them) may include one or more of *cryptosporidium* (cryptosporidiosis); *giardia lamblia* (giardiasis); *plasmodium* (malaria); or *trypanosoma cruzi* (chagas disease). Some examples of fungi (and the diseases or effect caused by them)

may include one or more of *pneumocystis jiroveci* (opportunistic pneumonia); *tinea* (ringworm); or *candida* (candidiasis).

Some examples of parasites may include one or more of roundworm, scabies, tapeworm, or flatworm. Some examples of protein-based pathogens may include prions (Bovine spongiform encephalopathy (BSE) commonly known as mad cow disease or variant Creutzfeldt-Jakob disease (vCJD)).

Toxins include proteins capable of causing disease on contact or absorption with body tissues by interacting with biological macromolecules and may be used as bioweapons. Suitable toxins may include Ricin, SEB, Botulism toxin, Saxitoxin, and many Mycotoxins.

Some other examples of diseases caused by biological agents may include anthrax, Ebola, Bubonic Plague, Cholera, Tularemia, Brucellosis, Q fever, Machupo, Coccidioides mycosis, Glanders, Melioidosis, *Shigella*, Rocky Mountain Spotted Fever, Typhus, Psittacosis, Yellow Fever, Japanese B Encephalitis, Rift Valley Fever, or Smallpox.

Biological agents may be present in food samples, in air samples, in water samples, in soil samples, in plant samples, or in biological samples. In one embodiment, biological agents may provide information regarding the spoilage of food samples, for example, the bacteria in a spoilt meat sample. In one embodiment, the biological agents may indicate the presence or concentration of *legionella pneumophila* in an industrial water sample (cooling, water, process water, or waste water). In one embodiment, the biological agents may indicate the presence or concentration of *cryptosporidia giardia* in a municipal water sample (drinking water or waste water). In one embodiment, the biological agents may indicate the presence or concentration of *lysteria* or *salmonella* in a food sample.

In one embodiment, the biological agents may be used as biological warfare agents. Detection and analysis of the biological agents may provide information regarding the infected area. In one embodiment, analysis of the biological agents may provide information regarding the effectiveness of disinfection of the affected environment.

In one embodiment, an analyte that may be detected using the compositions disclosed herein, may include one or more biomolecules. In one embodiment, a biomolecule-based analyte may be part of a biological agent, such as, a pathogen. In one embodiment, a biomolecule may be used for diagnostic, therapeutic, or prognostic applications, for example, in RNA or DNA assays. Suitable biomolecules may include one or more of peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, vitamins, antigens, or haptens. The term analyte refers to both separate molecules and to portions of such molecules, such as an epitope of a protein that may bind specifically with one or more probes.

Probes and their corresponding biomolecule analytes may be considered as binding pairs, of which non-limiting examples may include immune-type binding-pairs, such as, antigen/antibody, antigen/antibody fragment, or hapten/anti-hapten; nonimmune-type binding-pairs, such as biotin/avidin, biotin/streptavidin, folic acid/folate binding protein, hormone/hormone receptor, lectin/specific carbohydrate, enzyme/enzyme, enzyme/substrate, enzyme/substrate analog, enzyme/pseudo-substrate (substrate analogs that cannot be catalyzed by the enzymatic activity), enzyme/co-factor, enzyme/modulator, enzyme/inhibitor, or vitamin B12/intrinsic factor. Other suitable examples of binding pairs may include complementary nucleic acid fragments (including DNA sequences, RNA sequences, PNA sequences, and peptide nucleic acid sequences); Protein A/antibody; Protein G/antibody; nucleic acid/nucleic acid binding protein; or polynucleotide/polynucleotide binding protein.

In one embodiment, the composition may further include one or more polymer precursor. A polymer precursor may include monomeric species, oligomeric species, mixtures of monomeric species, mixtures of oligomeric species, polymeric species, mixtures of polymeric species, partially-crosslinked species, mixtures of partially-crosslinked crosslinked species, or mixtures of two or more of the foregoing. An initiator may be capable of initiating a polymerization reaction of the polymer precursor.

A polymer precursor may include reactive groups capable of chemically reacting to form a polymer. A reactive group may participate in a chemical reaction when exposed to one or more of thermal energy, electromagnetic radiation, or chemical reagents (for example, an initiator).

A polymer precursor may include an organic or inorganic backbone depending on the type of initiators and the compatibility of the polymer precursor with the composition (such as, solubility in the solvents employed). A suitable inorganic backbone for a polymer precursor may include main chain linkages other than that of carbon-carbon linkages or carbon-heteroatom-carbon linkages, for example, silicon-silicon linkages in silanes, silicon-oxygen-silicon linkages in siloxanes, phosphorous-nitrogen-phosphorous linkages in phosphazenes, and the like.

A suitable organic polymer precursor may essentially include only carbon-carbon linkages (for example, olefins) or carbon-heteroatom-carbon linkages (for example, ethers, esters and the like) in the main chain. Suitable examples of organic polymer precursors may include one or more of olefin-derived polymer precursors, for example, ethylene, propylene, and their mixtures; methylpentane-derived polymer precursors, for example, butadiene, isoprene, and their mixtures; polymer precursors of unsaturated carboxylic acids and their functional derivatives, for example, acrylics such as alkyl acrylates, alkyl methacrylate, acrylamides, acrylonitrile, and acrylic acid; alkenylaromatic polymer precursors, for example styrene, alpha-methylstyrene, vinyltoluene, and rubber-modified styrenes; amides, for example, nylon-6, nylon-6,6, nylon-1,1, and nylon-1,2; esters, such as, alkylene dicarboxylates, especially ethylene terephthalate, 1,4-butylene terephthalate, trimethylene terephthalate, ethylene naphthalate, butylene naphthalate, cyclohexanedimethanol terephthalate, cyclohexanedimethanol-co-ethylene terephthalate, and 1,4-cyclohexanedimethyl-1,4-cyclohexanedicarboxylate and alkylene arenedioates; carbonates; estercarbonates; sulfones; imides; arylene sulfides; sulfide sulfones; and ethers such as arylene ethers, phenylene ethers, ethersulfones, etherimides, etherketones, etheretherketones; or blends, homopolymers, or copolymers thereof.

In one embodiment, the polymer precursor may include functional groups that may chemically react to form a polymer via free radical polymerization, ring-opening polymerization, metathesis polymerization, anionic polymerization, cationic polymerization, or combinations of two or more of the foregoing. In one embodiment, the polymer precursor may include functional groups that may chemically react to form a polymer via free radical polymerization, atom transfer radical polymerization, ring-opening metathesis polymerization, or combinations of two or more of the foregoing. In one embodiment, the polymer precursor may include one or more of styrene, acrylate, methacrylate, or norbornene functional groups. In one embodiment, the polymer precursor may be soluble in a probe solution at room temperature. In one embodiment, the polymer precursor may be soluble in water at room temperature.

In one embodiment, the polymer precursor may include one or more signal generators. As used herein, the term "signal generator" may refers to a molecule capable of providing a detectable signal. A detectable signal may refer to a signal capable of being detected using one or more detection techniques including for example, spectrometry, calorimetry, spectroscopy, or visual inspection. Suitable examples of a detectable signal may include an optical signal, an electrical signal, or a radioactive signal.

The type of signal generator suitable for the compositions disclosed herein may depend on a variety of factors, including the nature of the analysis being conducted, the type of the energy source and detector used, the type of initiator employed, the type of probe, the type of target, or the solvents employed.

A signal generator may provide a characteristic signal following interaction with an energy source or a current. An energy source may include electromagnetic radiation source and a fluorescence excitation source. Electromagnetic radiation source may be capable of providing electromagnetic energy of any wavelength including visible, infrared and ultraviolet. Electromagnetic radiation may be in the form of a direct light source or may be emitted by a light emissive compound such as a donor fluorophore. A fluorescence excitation source may be capable of making a source fluoresce or may give rise to photonic emissions (that is, electromagnetic radiation, directed electric field, temperature, physical contact, or mechanical disruption). Suitable signal generators may provide a signal capable of being detected by a variety of methods including optical measurements (for example, fluorescence), electrical conductivity, or radioactivity. Suitable signal generators may be, for example, light emitting, energy accepting, fluorescing, radioactive, or quenching.

A suitable signal generator may be sterically and chemically compatible with the constituents to which it is bound, for example, a polymer precursor. A suitable signal generator may not interfere with the polymerization capability of the polymer precursor. Additionally, after the polymerization reaction, a suitable signal generator may not interfere with the binding of the probe to the analyte, nor may it affect the binding specificity of the probe. A suitable signal generator may be organic or inorganic in nature. In some embodiments, a signal generator may be of a chemical, peptide or nucleic acid nature.

A signal generator may be directly or indirectly detectable. A directly detectable moiety may be one that may be detected directly by its ability to emit a signal, such as for example a fluorescent label that emits light of a particular wavelength following excitation by light of another lower, characteristic wavelength and/or absorb light of a particular wavelength. An indirectly detectable signal generator may be one that may be detected indirectly by its ability to bind, recruit and, in some cases, cleave another moiety, which may in turn emit a signal. An example of an indirectly detectable signal generator may be an enzyme-based signal generator, which when contacted with a suitable substrate may cleave the substrate to provide a detectable signal. Alternatively, an indirectly detectable signal generator may be capable of binding a compound that does emit a signal. For example, a signal generator, such as, biotin which itself does not emit a signal when bound to labeled avidin or streptavidin molecules may be detected. Other examples of indirectly detectable signal generators may include ligands that bind specifically to particular receptors. Detectably labeled receptors may be allowed to bind to ligand labeled polymer precursors in order to detect the probes. For example, a polymer precursor may be attached to a biotin molecule and a signal generator may be attached to an avidin molecule that may bind specifically to biotin. Some other examples of indirectly detectable signal generators may include an affinity molecule, a ligand, a receptor, a biotin molecule, an avidin molecule, a streptavidin molecule, an antigen (e.g., epitope tags such as the FLAG or HA epitope), a hapten (e.g., biotin, pyridoxal, digoxigenin fluorescein and dinitrophenol), an antibody, an antibody fragment, a microbead, or combinations of two or more thereof.

In some embodiments, a signal generator may be selected from a light emissive molecule, a radioisotope (e.g., $P^{32}$ or $H^3$, $^{14}C$, $^{125}I$ and $^{131}I$), an optical or electron density marker, a Raman-active tag an enzyme, an enzyme substrate (for example, a chromogenic substrate), an electron spin resonance molecule (such as for example nitroxyl radicals), an electrical charge transferring molecule (i.e., an electrical charge transducing molecule), a semiconductor nanocrystal, a semiconductor nanoparticle, a colloid gold nanocrystal, a microbead, a magnetic bead, a paramagnetic particle, a quantum dot, or an affinity molecule (e.g., a biotin molecule, a streptavidin molecule, a protein, a peptide, nucleic acid, a carbohydrate, an antigen, a hapten, an antibody, an antibody fragment, or a lipid).

In some embodiments, a signal generator may include a light-emissive molecule. A light emissive molecule may emit light in response to irradiation with light of a particular wavelength. Light emissive molecules may be capable of absorbing and emitting light through luminescence (non-thermal emission of electromagnetic radiation by a material upon excitation), phosphorescence (delayed luminescence as a result of the absorption of radiation), chemiluminescence (luminescence due to a chemical reaction), fluorescence, or polarized fluorescence.

In some embodiments, a signal-generator may be directly detectable. In some embodiments, a signal generator may include a chromophore. In some embodiments, a signal-generator may include a fluorescent molecule or a fluorophore. Suitable chromophores and fluorophores may include one or more molecules listed hereinabove. In some embodiments, the signal generator may be part of a FRET pair. FRET pair includes two fluorophores that are capable of undergoing FRET to produce or eliminate a detectable signal when positioned in proximity to one another. Some examples of donors may include Alexa 488, Alexa 546, BODIPY 493, Oyster 556, Fluor (FAM), Cy3, or TTR (Tamra). Some examples of acceptors may include Cy5, Alexa 594, Alexa 647, or Oyster 656.

In some embodiments, a signal generator may essentially include a fluorophore. Examples of fluorophores include, but are not limited to, 4-acetamido-4'-isothiocyanatostilbene-2,2' disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethyl-couluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)4-methylcoumarin, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron. Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lanthanide chelate derivatives, quantum dots, cyanines, and squaraines. Some other examples of fluorophores may include one or one or more of fluorescein, Rhodamine, Texas Red, VECTOR Red, ELF (Enzyme-Labeled Fluorescence), Cy2, Cy3, Cy3.5, Cy5, Cy7, FluorX, Calcein, Calcein-AM, CRYPTOFLUOR, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)-amino]caproyl] (NBD), BODIPY, boron dipyrromethene difluoride, Oregon Green, MITOTRACKER. Red, DiOC(3), DiIC.sub.18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Lissamine, Umbelliferone, Tyrosine or Tryptophan.

In some embodiments, a signal generator may be indirectly detectable, for example, an enzyme/enzyme substrate combination. In some embodiments, an enzyme may precipitate a soluble substrate to form an insoluble product (for example, in immunohistochemistry). Further, an enzyme may catalyze a chemical reaction of a chromogenic substrate that may be measured using a suitable technique. For example, the enzyme may catalyze a color change in a substrate, which can be measured spectrophotometrically. Alternatively, an enzyme may alter the fluorescence or chemiluminescence properties of the substrate. Suitable examples of enzyme-substrate combinations are described herein below.

Horseradish peroxidase (HRPO) with hydrogen peroxidase as a substrate, wherein the hydrogen peroxidase may oxidize a dye precursor (e.g., orthophenylene diamine (OPD) or 3,3',5,5'-tetramethyl benzidine hydrochloride (TMB)). Other suitable HRPO substrates may include, but are not limited to, 2,2' Azino-di-3-ethylbenz-thiazoline sulfonate (ABTS, green, water soluble), aminoethyl carbazole, 3-amino, 9-ethylcarbazole AEC (3A9EC, red). Alpha-naphthol pyronin (red), 4-chloro-1-naphthol (4C1N, blue, blue-black), 3,3'-diaminobenzidine tetrahydrochloride (DAB, brown), ortho-dianisidine (green), o-phenylene diamine (OPD, brown, water soluble), TACS Blue (blue), TACS Red (red), 3,3',5,5'Tetramethylbenzidine (TMB, green or green/blue), TRUE BLUE (blue), VECTO VIP (purple), VECTOR SG (smoky blue-gray), and Zymed Blue HRP substrate (vivid blue).

Alkaline phosphatase (AP) with para-Nitrophenyl phosphate as chromogenic substrate. Other suitable AP substrates include, but are not limited to, AP-Blue substrate (blue precipitate, Zymed); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR Black (black), VECTO Blue (blue), VECTOR Red (red), Vega Red (raspberry red color).

β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). Other suitable β-galactosidase substrates, include, but are not limited to, 5-bromo-4-chloro-3-indoyl beta-D-galactopyranoside (X-gal, blue precipitate).

Suitable glucose oxidase (GO) substrates, include, but are not limited to, nitroblue tetrazolium (NBT, purple precipitate), tetranitroblue tetrazolium (TNBT, black precipitate), 2-(4-iodophenyl)-5-(4-nitorphenyl)-3-phenyltetrazolium chloride (INT, red or orange precipitate), Tetrazolium blue (blue), Nitrotetrazolium violet (violet), and 3-(4,5-dimethylthiazol-2-yl)-2,5-diphenyltetrazolium bromide (MTT, purple). Tetrazolium substrates may require glucose as a co-substrate. The precipitates associated with each of the substrates listed hereinabove may have unique detectable spectral signatures.

In some embodiments, the polymer precursor may be intrinsically labeled with a signal generator (for example, if the polymer precursor is an oligomer, during synthesis using a detectably labeled monomer). A polymer precursor that is intrinsically labeled may not require a separate signal generator in order to be detected. Rather the intrinsic label may be sufficient for rendering the polymer precursor detectable. In alternate embodiments, the polymer precursor may be labeled by binding to it a specific signal generator (i.e., extrinsically labeled).

A polymer precursor and a signal generator may be chemically linked to each other through functional groups capable of reacting and forming a linkage under suitable conditions. Suitable examples of functional group combinations may include, but are not limited to, amine ester and amines or anilines; acyl azide and amines or anilines; acyl halides and amines, anilines, alcohols, or phenols; acyl nitrile and alcohols or phenols; aldehyde and amines or anilines; alkyl halide and amines, anilines, alcohols, phenols or thiols; alkyl sulfonate and thiols, alcohols or phenols; anhydride and alcohols, phenols, amines or anilines; aryl halide and thiols; aziridine and thiols or thioethers; carboxylic acid and amines, anilines, alcohols or alkyl halides; diazoalkane and carboxylic acids; epoxide and thiols; haloacetamide and thiols; halotriazin and amines, anilines or phenols; hydrazine and aldehydes or ketones; hydroxyamine and aldehydes or ketones; imido ester and amines or anilines; isocyanate and amines or anilines; and isothiocyanate and amines or anilines. A functional group in one of the aforementioned functional group pair may be present in a polymer precursor and a corresponding functional group may be present in the signal generator. For example, a polymer precursor may include a carboxylic acid and the signal generator may include an amine, aniline, alcohol or acyl halide, or vice versa. Conjugation between the polymer precursor and the signal generator may be effected in this case by formation of an amide or an ester linkage.

In one embodiment, the polymer precursor may include one or more signal-generator-labeled-monomers. Suitable examples of signal generator-labeled-monomers may include-fluorophore-labeled-monomers. Some examples of fluorophore-labeled-monomers may include cyanine or fluorescein-labeled-monomers. Some examples of signal generator-labeled-polymer precursors in accordance with one embodiment of the invention may include structures having formulae (XIII) to (XVI).

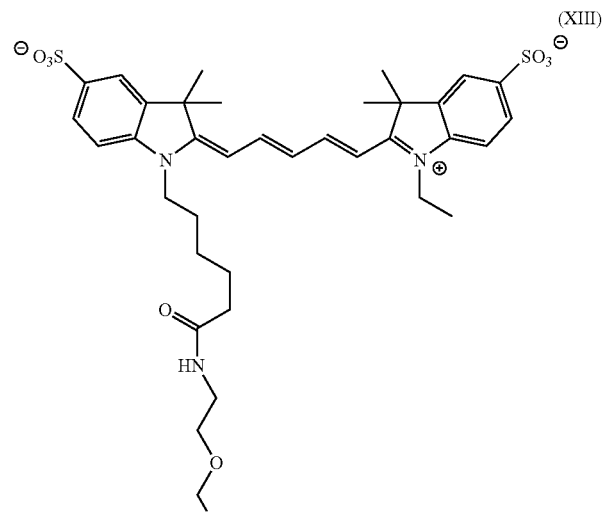
(XIII)

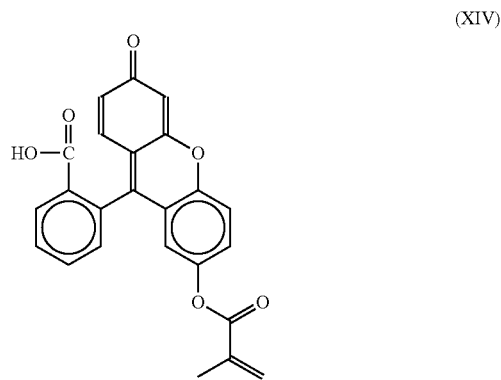
(XIV)

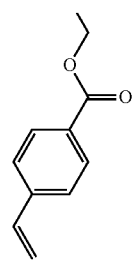

(XV)

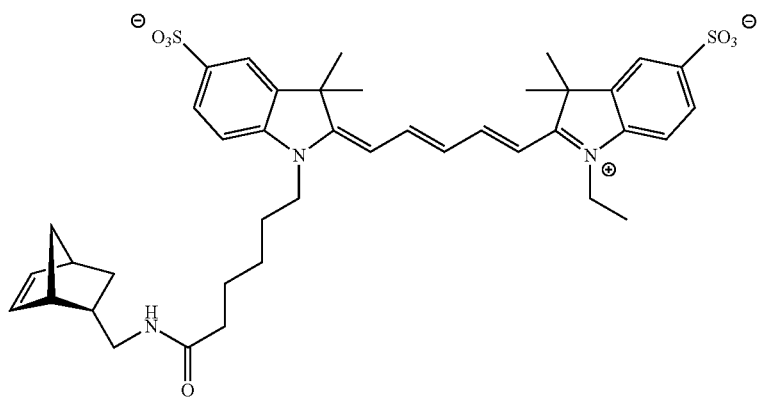

(XVI)

In one embodiment, a polymer precursor may include a mixture of monomers: signal-generator-labeled-polymer precursors and unlabeled polymer precursors. In one embodiment, unlabeled monomers may be employed along with the labeled polymer precursors to prevent quenching of signal between labeled polymer precursors. The concentration of labeled and unlabeled-polymer precursors may be varied depending on the molecular weight of polymer desired and the extent of dequenching required. Suitable unlabeled-polymer precursors may include one or more monomers polymerizable by the initiators employed in accordance with the compositions disclosed herein.

In one embodiment, an initiator may include an ATRP initiator and a polymer precursor may include a mixture of a fluorophore-labeled ATRP polymer precursors and unlabeled-ATRP polymer precursors. For example, a fluorophore-labeled ATRP polymer precursor may include one or more molecules having structures of formulae (XIII) to (XV) and unlabeled-ATRP polymer precursor may include an acrylate or styrene polymer precursors. In one embodiment, an unlabeled ATRP polymer precursor may have a structure of formula (XVII).

(XVII)

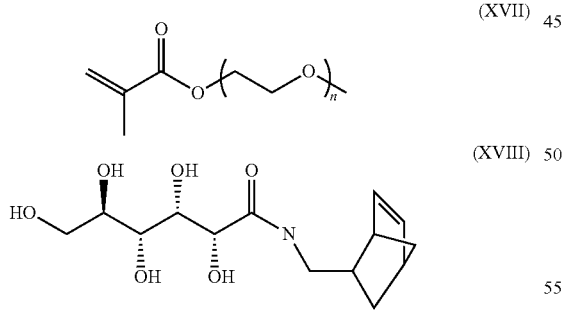

(XVIII)

In one embodiment, an initiator may include an ROMP initiator and a polymer precursor may include a mixture of a fluorophore-labeled ROMP polymer precursors and unlabeled-ROMP polymer precursors. For example, a fluorophore-labeled ROMP polymer precursor may include a molecule having a structure of formula (XVI) and unlabeled-ROMP polymer precursor may include a norbornene polymer precursor having a structure of formula (XVIII).

In one embodiment, a polymer precursor may be unlabeled, that is, may not include a signal generator. For compositions where a mixture of unlabeled polymer precursors may be employed, all the polymer precursors may be unlabeled, in accordance with one embodiment of the invention. In one embodiment, an unlabeled polymer precursor may include one or more functional groups that may be conjugated or bonded with signal generators post-polymerization reaction.

Some examples of non-labeled polymer precursors that may be used in compositions, in accordance with one embodiment of the invention, may include structures of formulae (XIX) or (XX). In one embodiment, a polymer formed from the polymer precursors with formulae (XIX) or (XX) may be conjugated to a signal generator, for example, via cyanine-labeled lysine or polylysine.

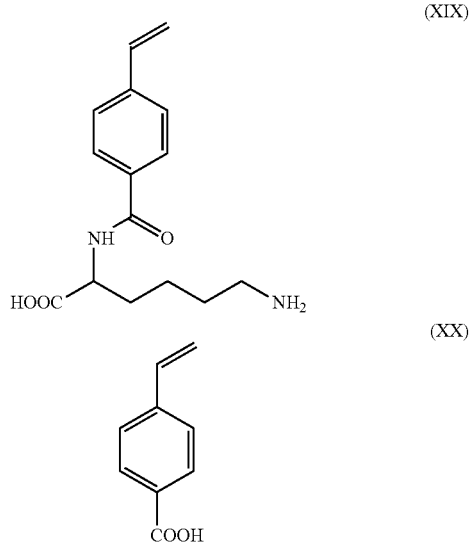

(XIX)

(XX)

In one embodiment, a polymer precursor may include a functional group that may be capable of initiating a polymerization reaction of another polymer precursor. In one embodiment, a polymer precursor may include a functional group that may be capable of bonding to an initiator that may initiate a polymerization reaction of another polymer precursor. For example, in one embodiment, an ATRP polymer precursor may include a ROMP initiator that may be capable of initiating a polymerizing reaction of a ROMP monomer. Similarly, in one embodiment, an ATRP polymer precursor may include a functional group that may form a bond with another initiator. Polymer precursors with initiators may provide for formation of branched or graft polymers. In one embodiment, a polymer precursor may include a functional group that may be capable of initiating a polymerization reaction of another polymer precursor. In one embodiment, a polymer precursor may include a functional group that may be capable of bonding to another initiator.

FIG. 6 illustrates a schematic example of a composition in accordance with one embodiment of the invention. The composition includes the complex 200 and a polymer precursor 220. The polymer precursor 220 furthers include a signal generator 230. As described hereinabove, in some embodiments, the polymer precursor may be unlabeled or may include functional groups capable of bonding to one or more signal generators post polymerization reaction. In some embodiments, the polymer precursor may include functional groups capable of bonding to one or more initiators post polymerization reaction.

In one embodiment, the complex 200 and the polymer precursor 220 may be present in the form of solution. In one embodiment, the complex 200 and the polymer precursor 220 may be present in the form of an emulsion. In one embodiment, the complex 200 may be immobilized on a solid support and the polymer precursor 220 may be present in the form of a solution in contact with the complex 200.

In one embodiment, the composition may include a reaction product of a composition. In one embodiment, a reaction product of the composition as disclosed herein may include a mixture of a polymer product bonded to the analyte through the probe and any unreacted polymer precursor. In one embodiment, the conversion of the polymer precursor may be complete, that is, the reaction product may be free of any unreacted polymer precursor. The polymer formed may be a homopolymer or a copolymer. The polymer formed may be linear, branched, or crosslinked.

In one embodiment, a polymer may be a homopolymer of labeled or unlabeled-monomers. In one embodiment, an unlabeled polymer may be labeled with a signal-generator after the formation of the polymer. In one embodiment, a polymer may be a copolymer of labeled monomers, unlabeled-monomers, or combinations thereof. The copolymer may be block, alternating, or a random copolymer. In one embodiment, a polymer may be a linear polymer. In one embodiment, a polymer may be a branched polymer. In one embodiment, a polymer may be a crosslinked polymer.

Average molecular weight of the polymer may depend upon one or more of the amount of signal desired, the type of initiators and monomers employed, ratio of monomer to initiator, or the reagent conditions (for example, presence or absence of solvent). In one embodiment, a polymer may have a number average molecular weight in a range of from about 50 grams per mole to about 100 grams per mole, from about 100 grams per mole to about 200 grams per mole, from about 200 grams per mole to about 500 grams per mole, from about 500 grams per mole to about 1000 grams per mole, from about 1000 grams per mole to about 2500 grams per mole, from about 2500 grams per mole to about 5000 grams per mole, from about 5000 grams per mole to about 10000 grams per mole, from about 10000 grams per mole to about 25000 grams per mole, from about 25000 grams per mole to about 50000 grams per mole, or from about 50000 grams per mole to about 100000 grams per mole. In one embodiment, a number average molecular weight of a polymer may be in a range of from about 100000 grams/mole to about 250000 grams/mole, from about 250000 grams/mole to about 500000 grams/mole, or from about 500000 grams/mole to about 1000000 grams/mole. In one embodiment, the number average molecular weight of a polymer may be in a range that is greater than about $10^6$ grams/mole. In one embodiment, the number average molecular weight of the polymer may be controlled by varying the initiator and polymer precursor concentration. In one embodiment, the number average molecular weight of the polymer may be related to the ratio of initiator and polymer precursor concentration, for example, in controlled polymerization In one embodiment, a polymer may have a unimodal molecular weight distribution. In one embodiment, a polymer may have a polydispersity index in a range that is less than about 2.0. In one embodiment, a polymer may have a polydispersity index in a range that is less than about 1.5. In one embodiment, a polymer may have a polydispersity index in a range of from about 1.0 to about 1.1, from about 1.1 to about 1.2, from about 1.2 to about 1.3, from about 1.3 to about 1.4, or from about 1.4 to about 1.5. In one embodiment, a polymer may have a polydispersity index in a range that is less than about 1.1. Polydispersity index refers to the ratio of a weight average molecular weight of the polymer to the number average molecular weight of the polymer and may be a measure of the molecular weight distribution.

Figure 9:
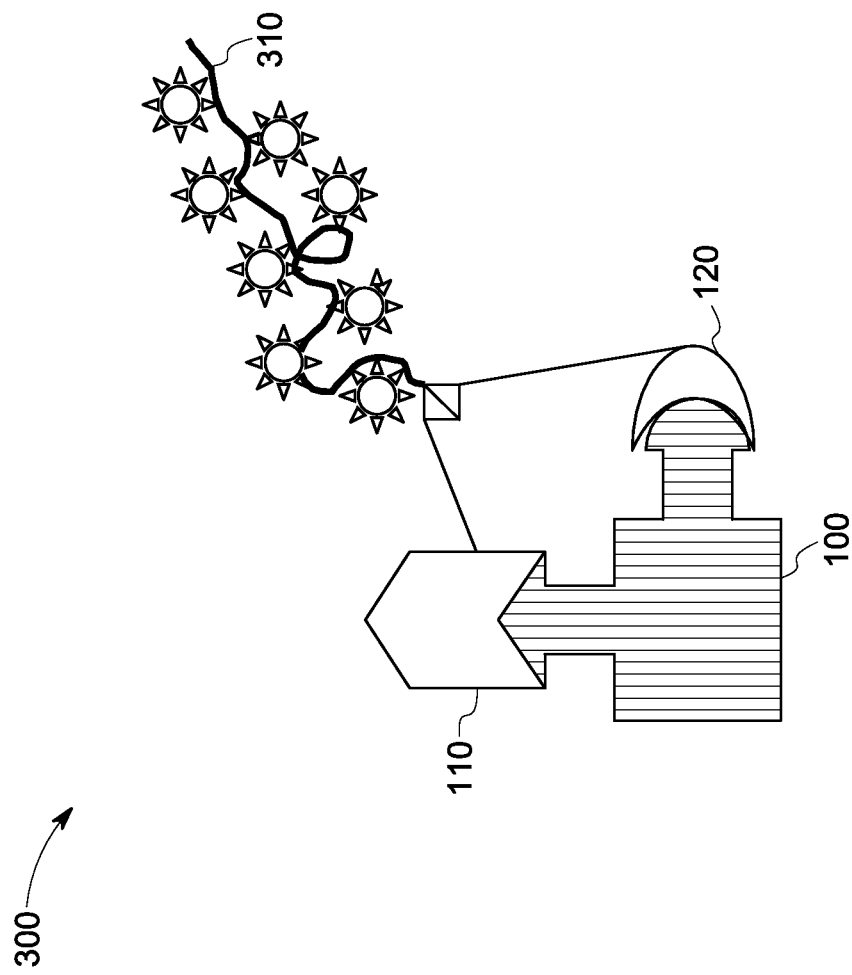
FIG. 9 is a schematic illustration of a composition in accordance with one embodiment of the invention.

In one embodiment, the composition may include an analyte, a first probe bonded to the analyte, a second probe bonded to the same analyte, a first initiator component bonded to the first probe, a second initiator component bonded to the second probe, first initiator component and second initiator component forming an initiator, and a polymer. FIG. 9 illustrates a schematic example of a composition 300 in accordance with one embodiment of the invention. The composition includes the complex 200 and a polymer 310 bonded to the complex through the first probe 110 and the second probe 120. The polymer includes a plurality of signal generators 230. As described hereinabove, the polymer 310 may be a homopolymer or a copolymer. Furthermore, although the polymer 310 is shown as linear in the figure, branched and crosslinked polymer may also be present in the composition.

In one embodiment, the composition may include a plurality (2, 3, . . . n) of probes, each bonded to a distinct initiator component, and each probe capable binding to a single analyte. The number of probes may depend on the number of distinct binding sites available in the analyte for binding and the degree of accuracy required for the analysis. In one embodiment, the composition may further include a polymer precursor, capable of undergoing a polymerization reaction initiated by the initiator formed by the plurality of initiator components. In one embodiment, the composition may include an analyte bonded to a plurality of probes, each probe bonded to a distinct initiator component, and the composition further including a polymer precursor. In one embodiment, the composition may include an analyte bonded to a plurality of probes, the probes bonded to a polymer via an initiator. A polymer may include one or more signal generator.

In one embodiment, the composition may include a plurality of probe pairs capable of detecting a plurality of analytes, that is, the composition may be capable of multiple analyte detection or multiplexing. Each analyte may be detected using a particular probe pair where each member of the probe pair may be specific to the analyte and each probe pair used in an analysis may be labeled with a distinguishable signal generator. As described hereinabove, each probe pair may be labeled with a signal generator via the initiator (formed from the initiator components bonded to the probes in a probe pair)

and the polymer bonded to the probes through the initiator. As used herein, a plurality may be an amount greater than two but less than infinity.

In one embodiment, a composition may include a plurality of probe pairs capable of binding to a single analyte. That is, each probe in the plurality of probe pairs may be capable of binding to a single analyte. Each probe pair may include a first probe bonded to a first initiator component and a second probe bonded to the second initiator component. Each probe pair may be capable of binding to an initiator formed when the initiator components are proximate to each other and when the probe pairs are bonded the analyte. In one embodiment, a composition may include a plurality of initiators each bonded to a particular probe pair and each initiator capable of initiating a polymerization reaction of a polymer precursor.

In one embodiment, all the components of the composition (analyte, probe, initiator, polymer precursor, polymer) may be soluble in water at a room temperature. In one embodiment, the composition may be soluble in water at room temperature. In one embodiment, the composition may be capable of forming an emulsion in water at room temperature. In one embodiment, all the components of the composition (analyte, probe, initiator, polymer precursor, polymer) may be soluble in an organic solvent at room temperature. Suitable organic solvent may include one or more of methanol, ethanol, dimethylsulfoxide, dimethylformamide, or N-methylpyrrolidinone.

In one embodiment, the composition may be soluble in a solvent, other than water, at room temperature. A suitable solvent may include a polar or a nonpolar solvent that may not affect the integrity of the analyte, probe, or binding specificity between the analyte and the probe. In one embodiment, a fluid composition may be provided. The fluid composition may include a first probe bonded to a first initiator component, a second probe bonded to a second initiator component, a polymer precursor, and a solvent. In one embodiment, the fluid composition may include an analyte bonded to the first probe and the second probe. In one embodiment, the fluid composition may include a reaction product of the initiator (formed from the first initiator component and the second initiator component) and the polymer precursor.

In one embodiment, a kit for detection of one or more analytes is provided. The kit may include a first probe bonded to a first initiator component; a second probe bonded to a second initiator component; and a polymer precursor. The first probe and the second probe may include specific binding sites that may be capable of binding to different binding sites present in a single analyte. In one embodiment, the kit may further include additional reagents required for the polymerization of the polymer precursor, for example, a metal ligand complex used along with the halide initiator in an ATRP reaction. In some embodiments a mixture of signal-generator-labeled-polymer precursors and unlabeled-polymer precursors may be employed, and the kit may include the labeled and unlabeled-polymer precursors as mixtures or separate compositions. In some embodiments, the polymer precursors employed may be all unlabeled, and the kit may further include one or more signal-generator capable of binding to the polymer post-polymerization. In one embodiment, the kit may further include additional reagents, such as, solvents, buffer solutions, and the like. In one embodiment, the kit may include a plurality (2, 3, . . . n) of probes, each bonded to a distinct initiator component and a plurality of polymer precursors. The plurality of probes may include specific binding sites that may be capable of binding to different binding sites present in a single analyte.

In one embodiment, an article for detection of an analyte is provided. The device includes a substrate and the substrate is capable of immobilizing one or more analytes on its surface. In one embodiment, the substrate may be capable of associating with a polymer. In one embodiment, the substrate may be capable of associating with the polymer through an analyte, a first probe bonded to a first initiator component, a second probe bonded to the second initiator component, and an initiator formed when the first initiator component and the second initiator component are proximate to each other.

A suitable substrate may include one or more of arrays, gels, glass slides, cells, tissue, tissue section, beads, blots, ELISA plates, and the like. In one embodiment, one or more analytes may be immobilized on a surface of the substrate by functionalizing the substrate using a suitable functional group, for example, an amino silane. An analyte may be immobilized on the substrate using the amine functional group. In one embodiment, an analyte may be immobilized on a surface of the substrate using specific-binding pairs such as streptavidin-biotin, for example, a biotinylated analyte may be immobilized on a streptavidin-functionalized substrate. In one embodiment, a probe (different from the first probe and the second probe and not bonded to an initiator component) capable of binding to the analyte may be immobilized on the substrate. An analyte may be bonded to the probe. A first probe and a second probe may be then bonded to the analyte forming, for example, a sandwich assay. The first probe and the second probe may be bonded to the first initiator component and the second initiator component respectively.

In one embodiment, the article is capable of detecting one or more biomolecules, for example in a molecular biology. In one embodiment, the article includes one or more of a protein microarray, an RNA microarray, a DNA microarray, an ELISA plate, a membrane used in a blot technique (for example, Western blot, Southern Blot, or Northern Blot), or a histological sample (cell, tissue, tissue section).

In one embodiment, a device is provided. The device includes the article as disclosed herein. The device is capable of detecting a type of the analyte, an amount of the analyte, or both type and amount of an analyte.

In one embodiment, the device is a handheld device capable of detecting an analyte on-site, for example, a device that may provide for detection of an analyte by a first responder. In one embodiment, the handheld device may be capable of detecting one or more chemical warfare agents or bio-warfare agents. In one embodiment, the device is capable of sensing one or more pollutants in an air sample, a soil sample, or a water sample. In one embodiment, the device is capable of sensing one or more spoilage-indicators in a food or beverage sample.

In one embodiment, the device is an autonomous detection system capable of automatically collecting, preparing, and detecting an analyte in an environment. In one embodiment, the autonomous detection system may be portable and may be capable of detecting an analyte on-site. In one embodiment, the autonomous detection system may be capable of detecting one or more chemical warfare agents or bio-warfare agents. In one embodiment, the device may be a hand-held device, may be a part of a mobile lab, or may be a part of a device capable of area analysis.

In one embodiment, a method of detection of an analyte is provided. The method includes contacting the analyte with a first probe bonded to a first initiator component and a second probe bonded to a second initiator component to form a complex. The contacting conditions (pH, concentration, temperature, and the like) between the analyte and the probes may be such that the probes may bind to the analyte through the specific binding sites present in the analyte.

As described hereinabove, the analyte may be portion of a sample to be analyzed (for example, a organophosphate in a water sample or a biological agent in an infected air sample), may be an extract of a sample to be analyzed (for example, an antigen in a blood sample), or the analyte may be the sample itself (for example, a nucleic acid in a buffer solution). In some embodiments, the analyte or the sample (if the analyte is present in a sample) may be processed and prepared before contacting the analyte or the sample with the probe(s). Analyte or sample preparation may include one or more of the following steps: separation of analyte, concentration of analyte, purification of analyte, analyte amplification, and the like. One or more of the aforementioned analyte or sample preparation techniques may be employed to make the analyte available for binding and detection.

In one embodiment, a method may further include immobilizing an analyte on a surface of a substrate using one or more of the techniques described herein elsewhere. A method may further include a blocking step in which the substrate (if employed) may be contacted with reagents that may block non-specific binding of the first probe and the second probe to the substrate.

In one embodiment, the analyte may be contacted with the first probe and the second probe simultaneously, that is, a mixture of probes may be used that may be contacted with the analyte. In one embodiment, the first probe and the second probe may bind to the analyte simultaneously. In one embodiment, the analyte may be contacted with the first probe and the second probe sequentially, that is, either the first probe or the second probe may be first contacted with the analyte followed by the other probe. In one embodiment, the first probe or the second probe may bind to the analyte first followed by binding of the other probe with the analyte to form a complex.

A method may also include one or more washing steps after contacting the analyte with the first probe, the second probe, or both the first probe and the second probe. A washing step may include contacting the analyte-probe complex with a series of washing solutions to remove any unbound or non-specifically bound probes.

A method may further include forming an initiator from the first initiator component and the second initiator component. In one embodiment, the complex may be further contacted with a polymer precursor. In one embodiment, the complex may be contacted with a polymer precursor under conditions effective to initiate a polymerization reaction of the polymer precursor to form a polymer.

A method may also include one or more washing steps after contacting the complex with the polymer precursor. A washing step may include contacting the analyte-polymer complex with a series of washing solutions to remove any unbound polymer or any unreacted polymer precursors.

In one embodiment, a polymer precursor may include one or more signal generators. Correspondingly, the polymer may include signal generators capable of providing a detectable signal. In one embodiment, a polymer precursor may not include a signal generator and the polymer precursors may include functional groups capable of binding to a signal generator. In one embodiment, the method may further include contacting a polymer with one or more signal generators.

The method may further include observing at least one signal from at least one polymer. A signal from the signal generator in the polymer may be detected using a detection system. The nature of the detection system used may depend upon the nature of the signal generators used. Thus, the detection system may include an electron spin resonance (ESR) detection system, a charge coupled device (CCD), AMS detection system (e.g., for radioisotopes), a fluorescent detection system, an electrical detection system, a photographic film detection system, a chemiluminescent detection system, an enzyme detection system, an atomic force microscopy (AFM) detection system (e.g., for the detection of microbeads), a scanning tunneling microscopy (STM) detection system (e.g., for the detection of microbeads), an optical detection system, a spectroscopic detection system (laser FM or multiphoton excitation), a near field detection system, or a total internal reflection (TIR) detection system.

One or more of the aforementioned techniques may be used to observe one or more characteristics of a signal from a signal generator (present in the polymer). In some embodiments, signal intensity, signal wavelength, signal location, signal frequency, or signal shift may be determined using one or more of the aforementioned techniques. In some embodiments, one or more aforementioned characteristics of the signal may be observed, measured, and recorded. In some embodiments, a signal generator may include a fluorophore and fluorescence wavelength or fluorescent intensity may be determined using a fluorescence detection system. In some embodiments, a signal may be observed in situ, that is, a signal may be observed directly from the signal generator associated through the polymer to the probe and the analyte in the sample. In some embodiments, a signal from the signal generator may be analyzed within the sample, obviating the need for separate array-based detection systems.

In some embodiments, observing a signal may include capturing an image of the sample. In some embodiments, a microscope connected to an imaging device may be used as a detection system, in accordance with the methods disclosed herein. In some embodiments, a signal generator (such as, fluorophore) may be excited and the signal (such as, fluorescence signal) obtained may be observed and recorded in the form of a digital signal (for example, a digitalized spectra or an image). The same procedure may be repeated for different signal generators (if present) that are bound to the analyte using the appropriate fluorescence filters.

In one embodiment, a signal may be analyzed to obtain information regarding the analyte. In one embodiment, the method may include correlating the signal to a type of an analyte. In one embodiment, the method may include correlating the signal to an amount of analyte. In one embodiment, the method may include correlating the signal to both type and amount of an analyte. In one embodiment, the presence or absence of a signal may indicate the presence or absence of coincident binding of an analyte in the sample. Coincident binding may refer to the binding of two or more probes on a single analyte. Coincident binding may be an indication of a presence of an analyte in a sample. A polymerization reaction resulting in the formation of a polymer (and a detectable signal) may only be initiated when the two probes are bonded to the analyte.

In some embodiments, an intensity value of a signal (for example, fluorescence intensity) may be measured and may be correlated to the amount of analyte in the sample. A correlation between the amount of analyte and the signal intensity may be determined using calibration standards. In one embodiment, the method may include determining the relative concentration or absolute amount of an analyte in a sample. The relative concentration or amount may be determined by measuring the amount of signal from probes coincidentally bound to an analyte.

In one embodiment, the signal amount may be compared to a calibration curve that may be prepared prior to or at the same time the sample is analyzed for absolute quantification. In one embodiment, the calibration curve may be a plot of signal intensity (y-axis) as a function of known analyte concentration (x-axis). In one embodiment, the method may include quantification of an analyte directly, that is, without the use of calibration curves between signal intensity and analyte amount. The latter may be possible, for example, in compositions employing controlled polymerization initiators. A controlled polymerization reaction may provide for synthesis of polymers with known molecular weight and narrow polydispersity index such that the amount of signal corresponding to a particular polymer molecular weight may be accurately determined. The amount of signal may be then correlated to the amount of analyte present in the sample. For example, the combined degree of polymerization (calculated from the molecular weight) of the polymer may be calculated to be about 10. The amount of coincident signal measured for the first signal and the second signal may correspond to about 100 degree of polymerization. The number of polymers that may be present may be then calculated to be about 100/10 equal to about 10. Since one polymer may be bonded to one analyte at any given time, the number of analytes present in the sample may be correspondingly calculated to be about 10 in a given test sample.

In embodiments where multiple analytes may be analyzed using multiple probes, relative amounts of different analytes in the biological sample may be determined by measuring different signal intensities. In some embodiments, one or more control samples may be used. By observing a presence or absence of a signal in the samples (sample of interest versus a control), information regarding the sample may be obtained. For example by comparing a diseased tissue sample versus a normal tissue sample, information regarding the analytes present in the diseased tissue sample may be obtained. Similarly by comparing signal intensities between the samples (i.e., sample of interest and one or more control), information regarding the expression of analytes in the sample may be obtained.

In one some embodiment, a location of the signal in the sample may be observed. In some embodiments relative locations of two or more signals may be observed. A location of the signal may be correlated to a location of the analyte, providing information regarding localization of different analytes in the sample. In some embodiments, an intensity value of the signal and a location of the coincident signal may be correlated to obtain information regarding localization of different analytes in the sample. For examples certain analytes may be expressed more in the cytoplasm relative to the nucleus in a tissue sample, or vice versa. In some embodiments, information regarding relative localization of analytes may be obtained by comparing location and intensity values of two or more signals.

In one embodiment, one or more of the observing or correlating step may be performed using computer-aided means. In some embodiment, one or more of the method steps be automated and may be performed using automated systems.

In one embodiment, a composition and a method, as disclosed herein, may be particularly applicable for detecting analytes in a rare or small sample (for example, a nanoliter volume sample) or in a sample where analyte concentration is low. In one embodiment, the test sample or the analyte sample may have a nanoliter volume, that is, it may be only necessary to load a nanoliter volume into the detection system in order to perform the method described herein.

In one embodiment, a composition and a method as disclosed herein may be particularly applicable for detecting an analyte at a nanomolar concentration. In one embodiment, a composition and a method as disclosed herein may be particularly applicable for detecting an analyte at a picomolar concentration. In one embodiment, a composition and a method as disclosed herein may be particularly applicable for detecting an analyte at a femtomolar concentration. In one embodiment, an analyte may be present at a frequency of less than about 1 in 10,000 molecules. In one embodiment, an analyte may be present at a frequency of less than about 1 in 1,00,000 molecules. In one embodiment, an analyte may be present at a frequency of less than about 1 in 1,000,000 molecules. In one embodiment, an analyte may be present at a frequency of less than about 1 in 2,000,000 molecules in the test sample. Accordingly, the composition and the method may be used to detect and analyze analytes that are extremely rare.

In one embodiment, the compositions and methods disclosed herein may have a limit of detection (LOD) of less than about 1000 analytes in about 18000 liters of air. In one embodiment, the compositions and methods disclosed herein may have a limit of detection (LOD) of about 100 analytes in about 18000 liters of air. In one embodiment, the compositions and methods disclosed herein may have a limit of detection (LOD) of about 10 analytes in about 18000 liters of air.

In one embodiment, the compositions and methods disclosed herein may provide for detection of analytes at low concentrations by amplifying the observable signal using a polymerization reaction. In one embodiment, the compositions and methods disclosed herein may provide for detection of analytes at low concentrations by amplifying the observable signal, thus obviating the need to amplify the analyte using techniques such as polymerase chain reaction (PCR). In one embodiment, the compositions and methods disclosed herein may provide for detection of analytes that may not be amenable to analyte amplification techniques like PCR, for example, protein analytes.

In one embodiment, the compositions and methods disclosed herein may provide for accurate detection of an analyte. The compositions and methods disclosed herein may provide for an accurate detection of an analyte using coincident binding and coincident detection. In one embodiment, the compositions and methods disclosed may provide for accurate detection of an analyte by reducing false positives. In one embodiment, the compositions and methods disclosed herein may provide for accurate detection of an analyte by reducing false negatives.

In one embodiment, the compositions and methods disclosed herein may provide a false positive rate for a single analyte in a range of less than about $10^{-6}$. In one embodiment, the compositions and methods disclosed herein may provide a false positive rate for a single analyte in a range of less than about $10^{-7}$. In one embodiment, the compositions and methods disclosed herein may provide a false positive rate for a single analyte in a range of less than about $10^{-8}$. In one embodiment, the compositions and methods disclosed herein may provide a false negative rate for a single analyte in a range of less than about $10^{-6}$. In one embodiment, the compositions and methods disclosed herein may provide a false negative rate for a single analyte in a range of less than about $10^{-7}$. In one embodiment, the compositions and methods disclosed herein may provide a false negative rate for a single analyte in a range of less than about $10^{-8}$.

In one embodiment, the compositions and methods disclosed herein may provide for detection of multiple analytes in a test sample, thereby conserving sample. In one embodiment, the degree of multiplexing may be 2 (i.e., 2 analytes may be detected in a single analysis). In one embodiment, the degree of multiplexing may in a range of from about 2 to about 4, from about 4 to about 6, from about 6 to about 10, from about 10 to about 20, from about 20 to about 50, from about 50 to about 100, from about 100 to about 250, or from about 250 to about 500. In one embodiment, the degree of multiplexing may be greater than about 500.

In one embodiment, the compositions and methods disclosed herein may provide a detectable signal in a test time in a range of less than about 2 hours, in a range of less than about 1 hour, in a range of less than about 30 minutes, in a range of less than about 15 minutes, or in a range of less than about 5 minutes.

EXAMPLES

The following examples are intended only to illustrate methods and embodiments in accordance with the invention, and as such should not be construed as imposing limitations upon the clauses.

Examples 1-4 describe the synthesis of a polymer-precursor conjugated to a signal generator.

Example 1

Synthesis of Cy5-Labeled-ATRP-Monomer

Synthesis of Compound 2. A solution of di-tert-butyl carbonate (2.57 g, 11.8 mmol) in chloroform (10 mL) is added to a solution of compound 1, that is 2-(2-amino-ethoxy)ethanol (1.25 g, 11.9 mmol), in chloroform (10 mL). The mixture is stirred at room temperature for about two hours. The solution is washed with water (15 mL) and the organic layer dried over anhydrous $MgSO_4$ and concentrated in vacuo to provide compound 2 (2.31 g, 95%). $^1$H NMR ($CDCl_3$): δ 1.38 (9H, s), 3.25-3.28 (2H, m), 3.47-3.52 (4H, m), 3.66-3.69 (2H, m), 4.82 (1H, bs).

Synthesis of Compound 4. DCC (1.24 g, 6.0 mmol) and DMAP (0.36 g, 3.0 mmol) are added to 4-ethenylbenzoic acid (i.e. compound 3) (0.82 g, 5.5 mmol) and alcohol 2 (1.13 g, 5.5 mmol) in $CH_2Cl_2$ (30 mL), and the mixture is stirred overnight. Dicyclohexylurea (DCU) is filtered off and $H_2O$ (15 mL) is added. The aqueous and organic layers are separated, and the aqueous layer is extracted with $CH_2Cl_2$ (3×30 mL). The combined organic extracts are dried with $MgSO_4$, concentrated in vacuo, and chromatographed (hexanes:EtOAc, 20:1 to 5:1) to provide ester 4 (0.99 g, 54%). $^1$H NMR ($CDCl_3$): δ 1.43 (9H, s), 3.33-3.34 (2H, m), 3.58-3.60 (2H, m), 3.78-3.81 (2H, m), 4.46-4.48 (2H, m), 4.92 (1H, bs), 5.39 (1H, d), 5.86 (1H, d), 6.76 (1H, dd), 7.47 (2H, d), 8.01 (2H, d).

Figure 10:
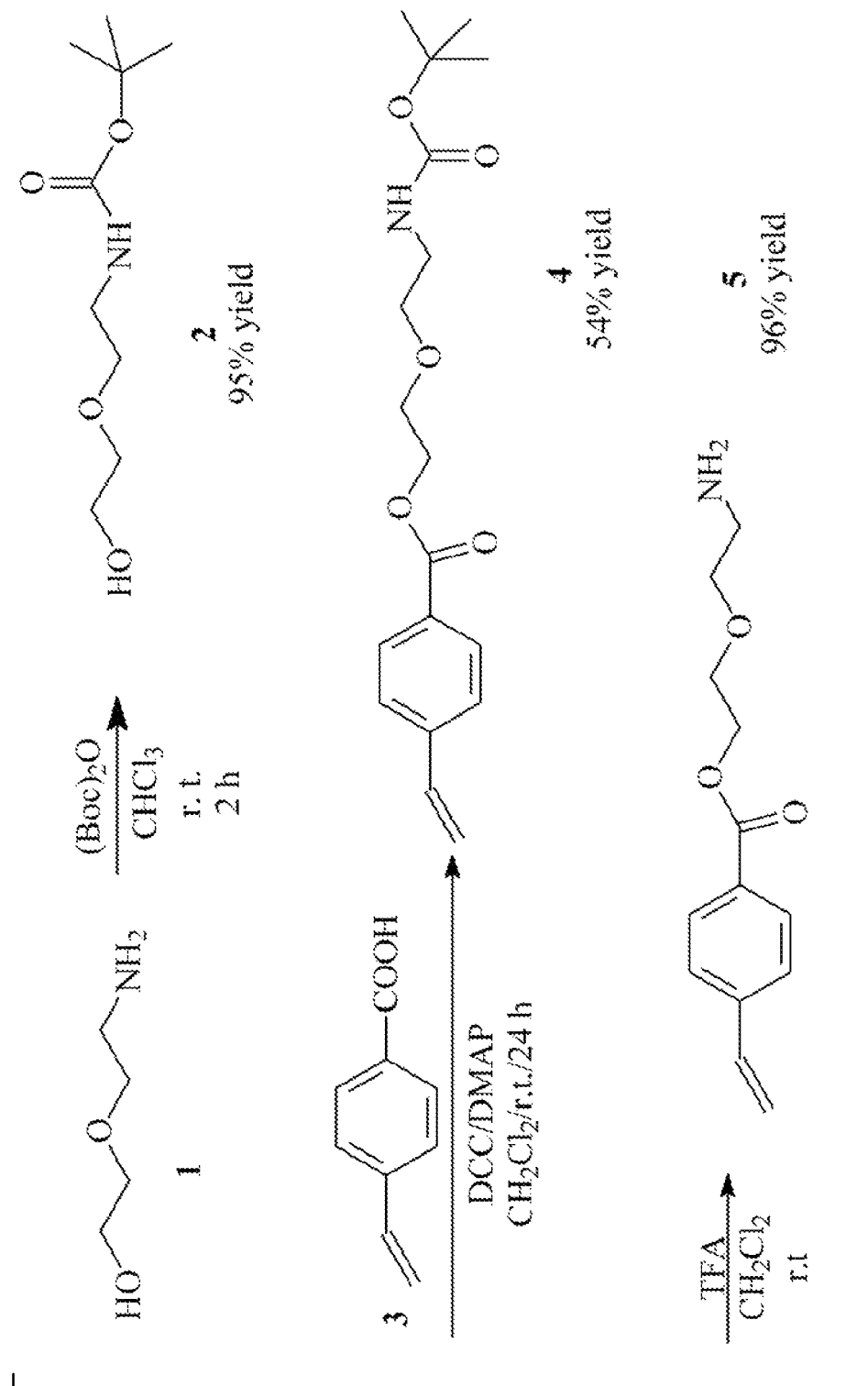
FIG. 10 is a reaction scheme for synthesis of a modified polymer precursor in accordance with one embodiment of the invention.

Synthesis of Compound 5 ("Amino Styrene 5"). Trifluoroacetic acid (2 mL) is added to a solution of compound 4 (0.15 g, 0.46 mmol) in $CH_2Cl_2$ (6 mL) and stirred at room temperature for about two hours. The resulting mixture is washed with saturated aqueous $NaHCO_3$ and extracted with $CH_2Cl_2$. The organic layer is dried with $Na_2SO_4$, concentrated in vacuo, and chromatographed ($CH_2Cl_2$:MeOH, 20:1 to 10:1, with 1% $Et_3N$) to provide compound 5 (0.10 g, 92%). $^1$H NMR ($CDCl_3$): δ 2.88-2.91 (2H, m), 3.56-3.59 (2H, m), 3.80-3.82 (2H, m), 4.47-4.49 (2H, m), 5.38 (1H, d), 5.86 (1H, d), 6.76 (1H, dd), 7.46 (2H, d), 8.01 (2H, d). The reaction scheme is shown in FIG. 10.

Figure 11:
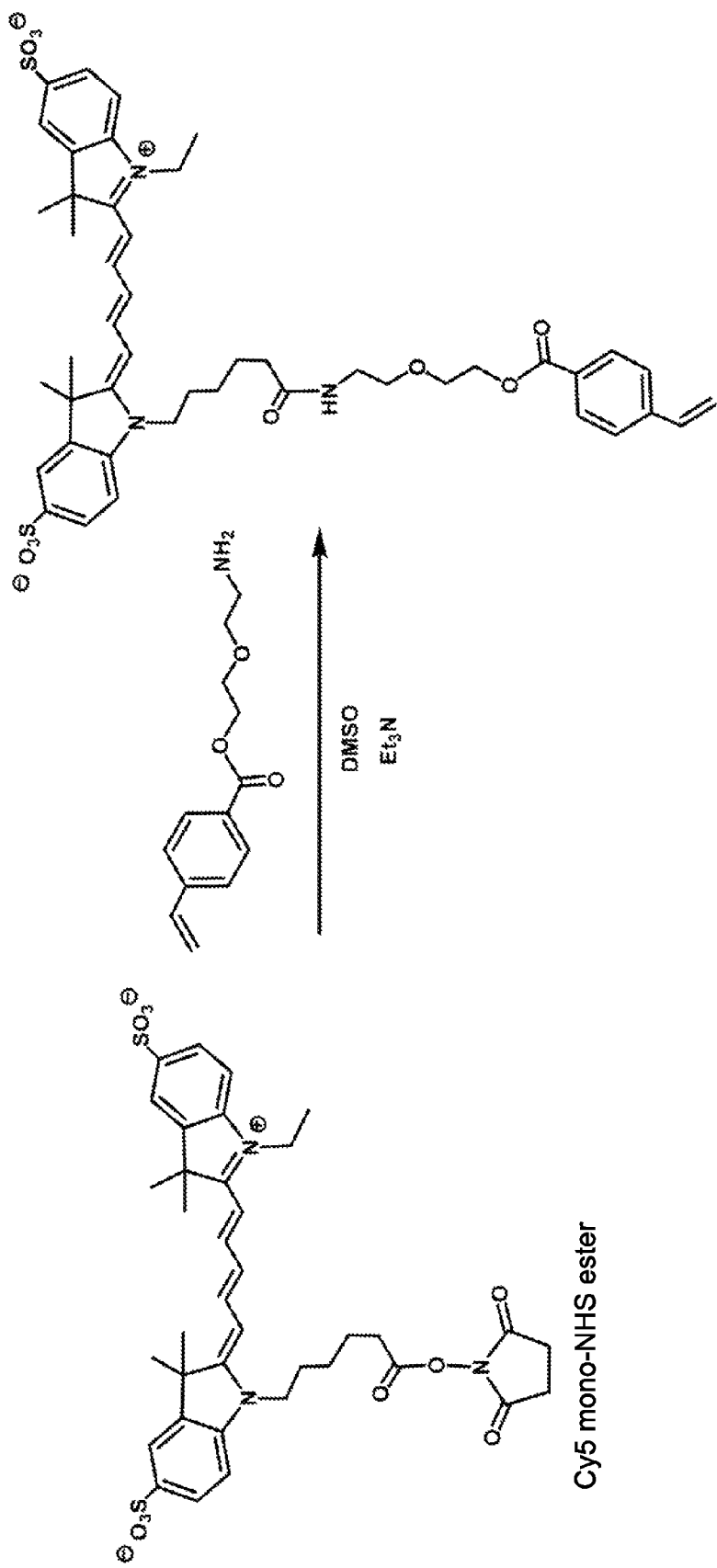
FIG. 11 is a reaction scheme for synthesis of a signal generator-modified polymer precursor in accordance with one embodiment of the invention.

Synthesis of ATRP Dye-Monomer Using Cy5 and Compound 5. Cy5 mono-NHS ester (5.0 mg, 6.3 mmol) in 2.0 mL DMSO is added into amino styrene 5 (1.5 mg, 6.3 mmol) in DMSO (2.0 mL). After 0.13 mL of triethylamine (0.95 mmol) is added into the mixture, the reaction is stirred over night in dark at room temperature. The crude product is purified by HPLC (C-18, $CH_3CN/H_2O/CF_3COOH$) to give 11 (5.0 mg, 87% yield). The reaction scheme is shown in FIG. 11.

Example 2

Synthesis of FITC-Labeled-ATRP-Monomer (FITC-MA)

Figure 12:
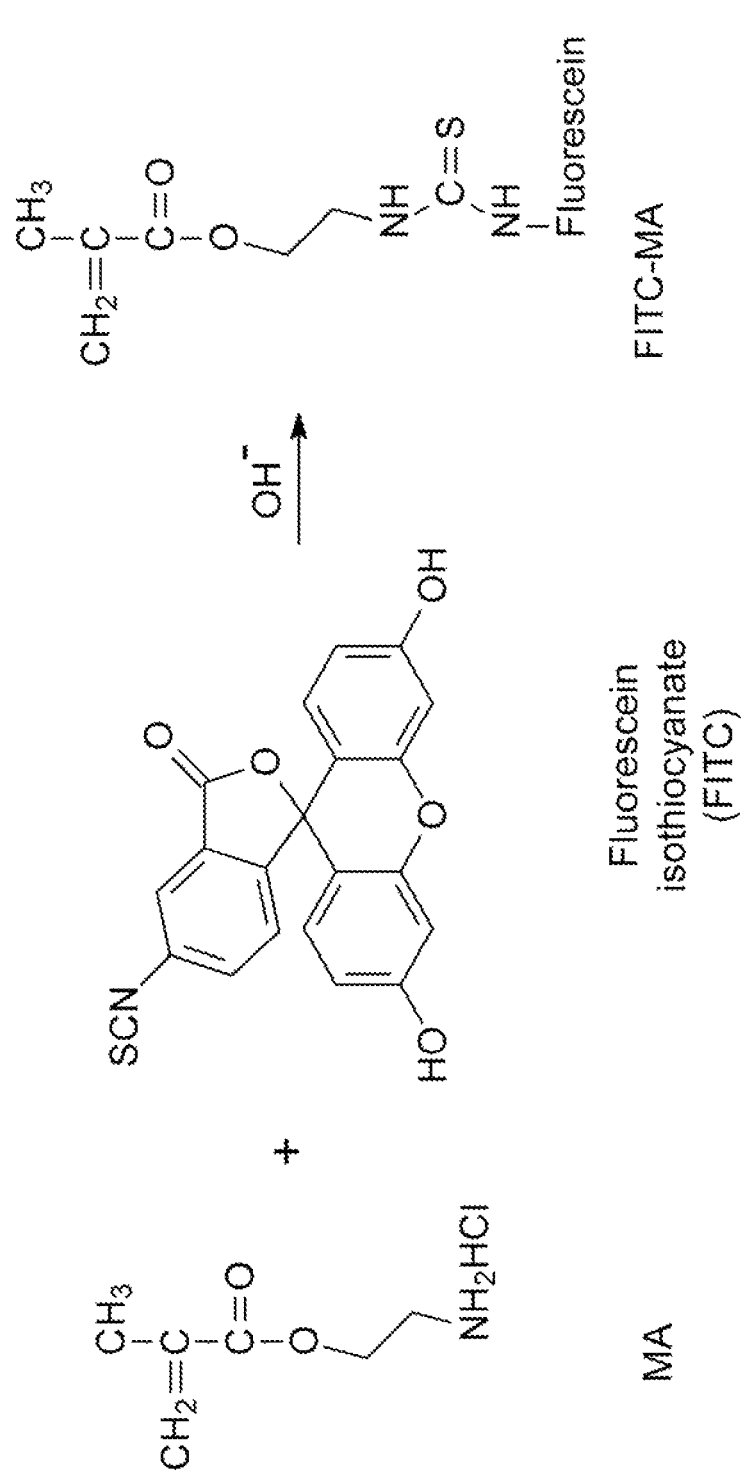
FIG. 12 is a reaction scheme for synthesis of a signal generator-modified polymer precursor in accordance with one embodiment of the invention.

Six milligrams of sodium hydroxide (0.15 mmol) is added to a solution of 2-aminoethlyl methacrylate hydrochloride (25 mg, 0.153 mmol) in 1 mL sodium carbonate buffer (pH=9.6). Fluorescein isothiocyanate (FITC) (65 mg, 0.17 mmol) dissolved in 1.5 mL DMSO is added into the mixture. The mixture is stirred over night at room temperature. The resulting clear red solution can be stored at 2° C. without further purification. $^1$H NMR (DMSO-d6): δ 6.10 (1H, s), 5.68 (1H, s), 4.26 (2H, t), 3.83 (2H, t), 1.89 (3H, s), 0.42 (6H, s). The reaction scheme is shown in FIG. 12.

Example 3

Synthesis of Bifunctional ATRP Monomer for Post-Polymerization Modification

Synthesis of BOC-protected N-(4-vinylbenzoyl)lysine, compound 7: A solution of DCC (0.68 g, 3.3 mmol), DMAP (0.10 g, 2.5 mmol), $Et_3N$ (0.46 mL, 3.3 mmol) and compound 6 (0.89 g, 3.0 mmol) in $CH_2Cl_2$ (15 mL) is added to a solution of 4-vinylbenzoic acid (i.e. compound 3) (0.44 g, 3.0 mmol) in $CH_2Cl_2$ (15 mL) and the mixture is stirred overnight. Dicyclohexylurea (DCU) is filtered off and the filtrate is concentrated. The crude product is purified by silica gel column chromatography with hexane/EtOAc (4:1 to 1:1) as the eluent. Compound 7 is obtained in 89% yield (1.05 g). $^1$H NMR ($CDCl_3$): δ 1.41 (9H, s), 1.49-1.57 (2H, m), 1.80-1.84 (2H, m), 1.95-2.01 (2H, m), 3.11-3.12 (2H, m), 3.78 (3H, s), 4.60 (1H, bs), 4.79-4.84 (1H, m), 5.36 (1H, d), 5.84 (1H, d), 6.71-6.78 (2H, m), 7.47 (2H, d), 7.79 (2H, d).

Figure 13:
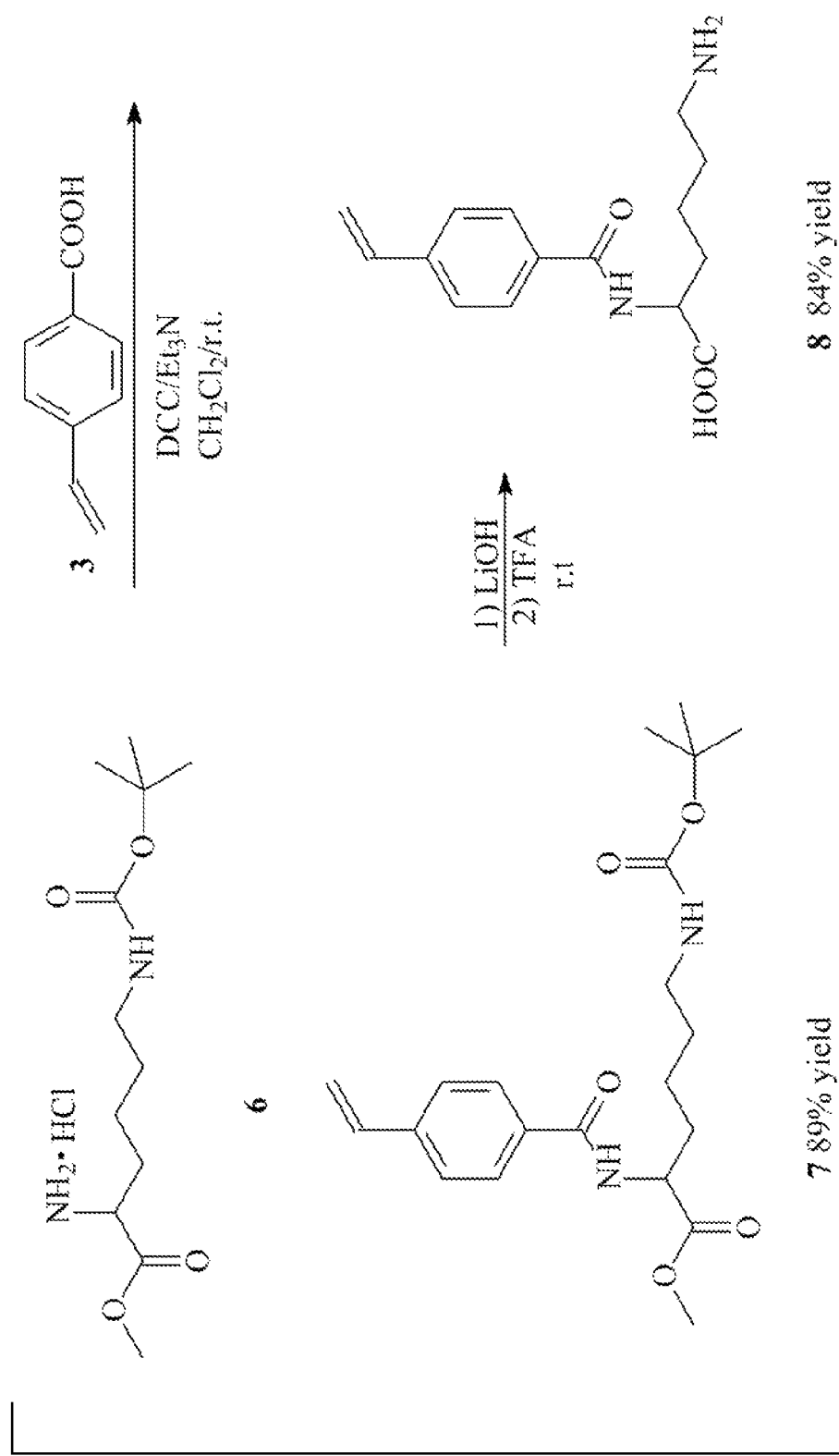
FIG. 13 is a reaction scheme for synthesis of a modified polymer precursor in accordance with one embodiment of the invention.

Synthesis of N-(4-vinylbenzoyl)lysine, compound 8, ("VBA-Lys"): A solution of compound 7 (0.13 g, 0.34 mmol) in dioxane/MeOH (6 mL) is hydrolyzed with 1 M LiOH, at a pH between about 10 and about 9.5. The mixture is stirred at room temperature for 2 to 3 hours. The completeness of the reaction is judged using thin layer chromatography (TLC). Trifluoroacetic acid (0.5 mL) is added to the solution and followed by stirring at room temperature for another two hours. The resulting mixture is concentrated in vacuo, and separated by chromatography ($CH_2Cl_2$:MeOH, 20:1 to 10:1, with 1% $Et_3N$) to give compound 8 (0.08 g, 84% yield) with a trace amount of $Et_3N$ or a salt thereof. $^1$H NMR ($CDCl_3$): δ 1.45-1.58 (2H, m), 1.80-1.89 (2H, m), 2.01-2.09 (2H, m), 3.07-3.14 (2H, m), 4.49-4.52 (1H, m), 4.68 (1H, bs), 5.32 (1H, d), 5.81 (1H, d), 6.74 (1H, d), 7.43 (2H, d), 7.83 (2H, d). The reaction scheme is shown in FIG. 13.

Example 4

Synthesis of Cy5-Labeled-ROMP Monomer

Synthesis of 5-Norbornene-2-methanamine (bicyclo[2.2.1]hept-5-en-2-ylmethanamine). A three-neck flask is equipped with mechanical stirrer, reflux condenser and dropping funnel. The flask is charged under $N_2$, with 42 ml of a 1.0 M solution of lithium aluminum hydride in anhydrous ether (42 mmol). A solution of 5 g of 5-Norbornene-2-carbonitrile (bicyclo[2.2.1]hept-5-ene-2-carbonitrile) in 45 ml of ether (42 mmol, 1.0 M) is added dropwise through the addition funnel at a rate that allows a gentle reflux. After one hour, the mixture is cooled to 0° C. and water is added dropwise until hydrogen gas liberation is no longer observed. To this, 100 ml of 20% sodium potassium tartrate is added and produces a clear solution. The reaction solution is transferred to a separatory funnel, and the aqueous phase is collected and washed with 3×50 ml portions of ether. The combined ether fractions are dried with calcium sulfate and solvent is removed by rotary evaporation yielding a yellow oil. This product is further distilled under reduced pressure to yield a clear oil.

Figure 14:
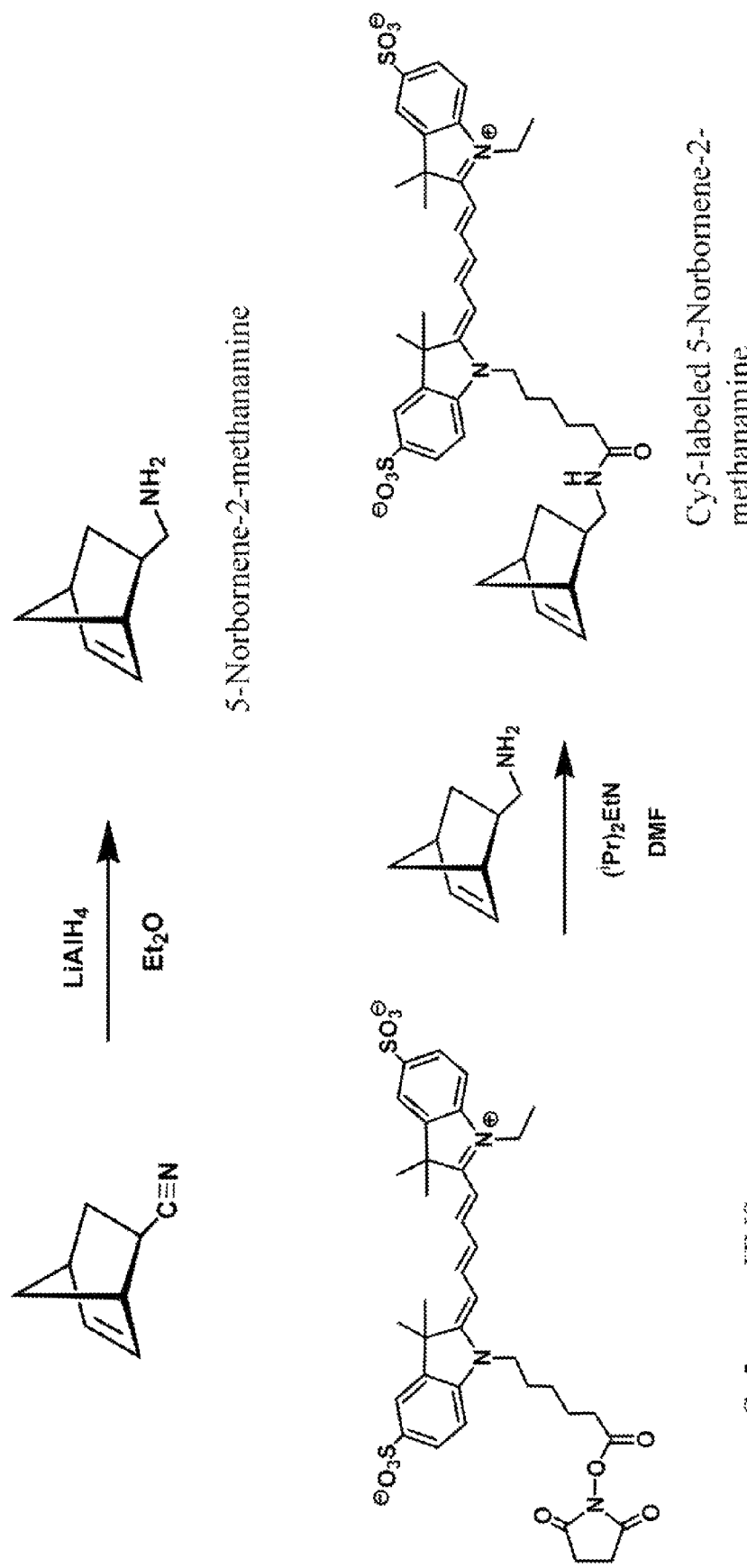
FIG. 14 is a reaction scheme for synthesis of a signal generator-modified polymer precursor in accordance with one embodiment of the invention.

Synthesis of Cy5-labeled 5-Norbornene-2-methanamine (ROMP monomer). To a $N_2$-flushed vial is added a 100 ml of a 400 mM solution of 5-Norbornene-2-methanamine (5 mg, 0.04 mmol, 130 mM final concentration), 100 ml of a 340 mM solution of Cy5 mono-NHS ester N,N-diisopropylethylammonium salt (30 mg, 0.034 mmol, 113 mM final concentration). With stirring, 100 ml of N,N-diisopropylethylamine (75.7 mg, 0.59 mmol, 2 M final concentration) is added and the dark blue solution is stirred overnight under $N_2$. This is purified by HPLC and lyophilized to yield a deep blue microcrystalline powder. The reaction scheme is shown in FIG. 14.

Examples 5-10 describe the procedure for modification of an initiator or immobilization of an initiator on a substrate.

Example 5

Synthesis of Silane-Modified ATRP Initiator

Synthesis of compound 9: Five grams of 4-pentene-1-ol (5.0 g, 0.058 mol), triethylamine 12 mL, and anhydrous dichloromethane (50 mL) are added to a dry 250 mL one-necked round-bottomed flask immersed in an ice bath. Eighteen grams of 2-bromoisobutyryl bromide (BiBB) (18 g, 0.078 mol) dissolved in 30 mL dichloromethane is added dropwise to the flask using a syringe over the course of 0.5 hour. The reaction mixture is stirred at 20° C. over night. The mixture is extracted with 10% saturated sodium carbonate three times and dried over anhydrous sodium sulfate. The dichloromethane is removed by rotary evaporation. Vacuum distillation affords 10.4 g of compound 9. (yield: 10.4 g, 76%). $^1$H NMR (CDCl$_3$): δ 5.81 (1H, m), 5.03 (2H, m), 4.19 (2H, t), 2.19 (2H, m), 1.94 (6H, s), 1.80 (2H, m).

Figure 15:
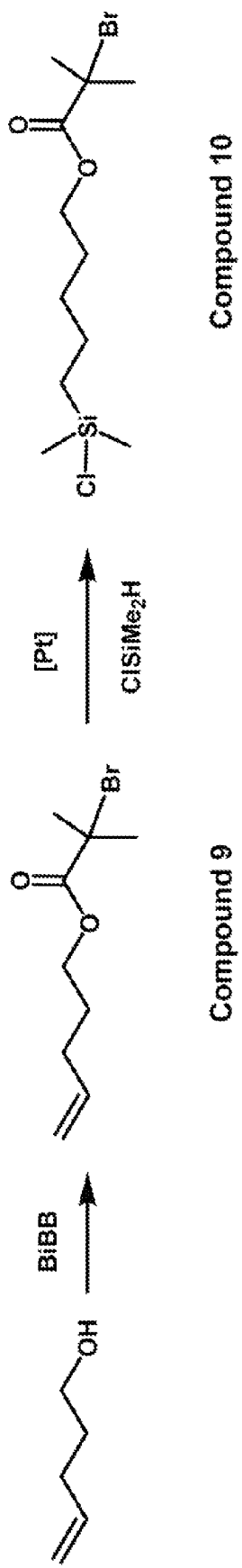
FIG. 15 is a reaction scheme for synthesis of a modified initiator in accordance with one embodiment of the invention.

Synthesis of compound 10 (silane-modified ATRP initiator): Two drops of Karstedt's catalyst is added at 0° C. to a mixture of compound 9 (10.42 g, 0.044 mol) and chlorodimethylsilane (6.6 mL, 0.058 mol) in 100 mL flask. The mixture is stirred at room temperature over night. The unreacted silane is removed by rotary evaporation. The mixture is distilled under vacuum to afford 11.2 g compound 10 (77% in yield). $^1$H NMR (CDCl$_3$): δ 4.19 (2H, t), 1.95 (6H, s), 1.71 (2H, t), 1.47 (4H, m), 0.86 (2H, t), 0.42 (6H, s). The reaction scheme is shown in FIG. 15.

Example 6

Synthesis of Bifunctional ATRP Initiator for Conjugation to Primary Amines

Figure 16:
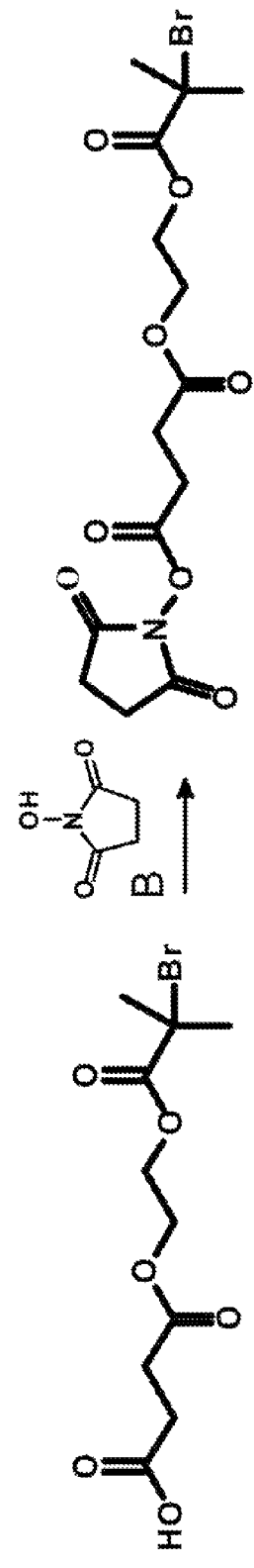
FIG. 16 is a reaction scheme for synthesis of a modified initiator in accordance with one embodiment of the invention.

N-Hydroxysuccinimide (B, 1.28 g) and the free acid (A, 2.3 g) are dissolved in CH$_2$Cl$_2$ (90 mL) and cooled to 0° C. EDCI (2.09 g) is added, the reaction is stirred for 10 min at 0° C. and then stirred overnight at room temperature. The reaction is diluted with Et$_2$O (20 mL), washed with 5% aqueous acid (10 mL), saturated aqueous sodium bicarbonate (10 mL) and brine (10 mL) and dried with sodium sulfate. After concentration under reduced pressure, the resulting residue is purified by flash chromatography (silica gel, 1:1 hexane:ethyl acetate) to yield 3.82 g of the activated ester as a colorless oil. FIG. 16 is a reaction scheme for synthesis of a modified initiator in accordance with one embodiment of the invention.

Example 7

Preparation of Surface-Supported ATRP Initiator on Quartz Surface Using Silanated-ATRP Initiator Quartz slides (10×10 mm$^2$) are soaked in 10% NaOH overnight and then rinsed with deionized (DI) water. The slides are then sonicated in DI water successively with 1% HCl, water, and finally with ethanol. Each sonication step lasts about 20 minutes. The slides are dried at 110° C. under vacuum for two hours, and are immersed in dry THF (20 mL). Then 0.5 mL of compound 10 is injected into the suspension via a syringe. The mixture is stirred and refluxed under $N_2$ atmosphere overnight. The slides are then washed by anhydrous THF thoroughly and dried in air.

Example 8

Preparation of Surface-Supported ATRP Initiator on a Quartz Surface Using Biotinylated-Initiator Drops of biotin-NHS (100 μL of 2 mM in PBS at pH=7.4) are dropped onto polylysine film using a micropipette. Another polylysine-coated slide is loaded facedown on top of the slide. The slides are incubated for two hours at room temperature, and then rinsed thoroughly with deionized water and PBS buffer solution successively. Streptavidin (100 μL, 1.0 mg/mL in PBS) is loaded on the biotin-modified slides. The coupling reaction is conducted overnight at about 2 to 8° C., then they are washed with PBS buffer solution and Tween 20 separately. Alternatively, the coupling reaction can be run for about two hours at room temperature. Finally, 100 μL of biotinylated initiator having formula XXI (4 mg/mL in methanol) is diluted with 20 mL PBS buffer, and the slides are immersed therein. The slides are incubated overnight and then washed with PBS buffer.

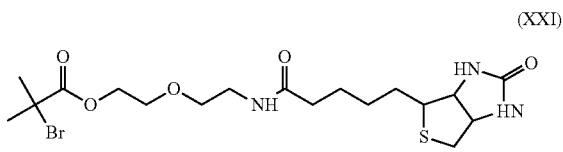 [SMILES: CC(C)(Br)C(=O)OCCOCCNC(=O)CCCCC1SCC2NC(=O)NC21]

(XXI)

Example 9

Preparation of Surface-Supported ATRP Initiator on Magnetic Particles

Two milliliters of streptavidin-coated iron oxide particles (i.e. magnetic particles) and 10 μL of biotin initiator having formula (XXI) are put into a flask and the mixture is stirred overnight. The magnetic particles are collected with a magnet and washed with PBS buffer five times.

Example 10

Preparation of Surface-Supported ROMP Initiator on Polystyrene Beads

Synthesis of (vinyl) polystyrene: Chloromethyl polystyrene resin (10 g, 1 mmol/g of Cl, 10 mmol of Cl, 100-200 mesh) is swelled by shaking overnight in 60 ml THF. Under $N_2$, n-butyl lithium (46 ml, 1.6 M, 74 mmol) is added dropwise to a 300 ml suspension of lithium iodide (9.9 g, 74 mmol) and trimethylsulfonium iodide (16.32 g, 80 mmol) at 0° C. After addition, the reaction is stirred for an hour at 0° C. This is added, at 0° C., to the swelled (chloromethyl) polystyrene resin in THF and the suspension is shaken overnight at room temperature. The mixture is diluted with methanol and filtered through a 0.45 m PTFE membrane. The resin is washed with methanol/acetic acid (80/20), methanol and methylene chloride and dried under vacuum at room temperature for about 16 hours.

Figure 17:
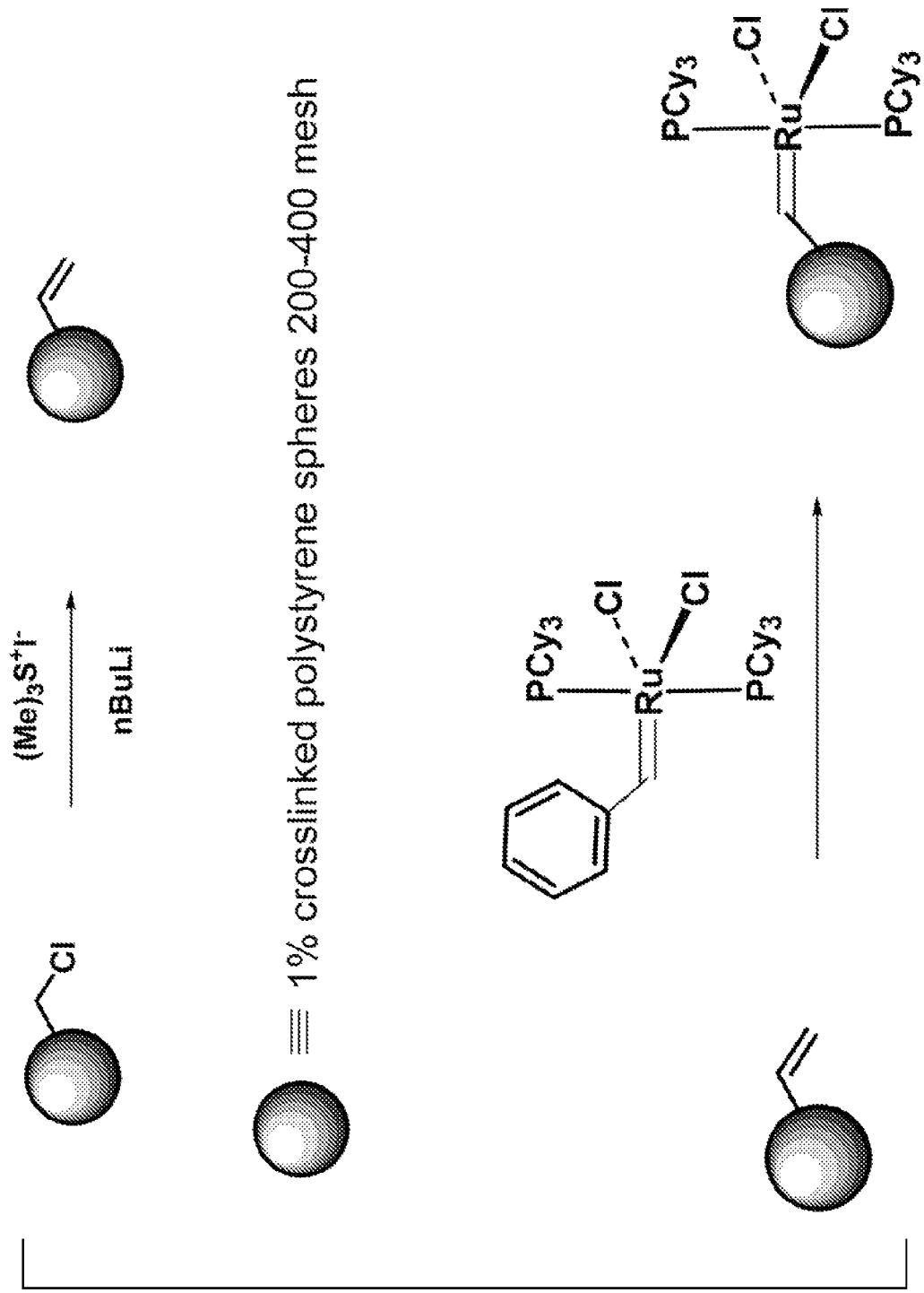
FIG. 17 is a reaction scheme for preparation of an initiator immobilized on a polystyrene bead.

Synthesis of bis(tricyclohexylphosphine)benzylidine ruthenium dichloride polystyrene resin. Under $N_2$, a 2.5 ml methylene chloride solution of bis(tricyclohexylphosphine) benzylidine ruthenium dichloride (130 mg, 0.16 mmol, 64 mM) is added to a suspension of (vinyl) polystyrene (2 g, 1 mmol/g vinyl, 2 mmol vinyl, 100-200 mesh) in 40 ml methylene chloride and shaken at room temperature for one hour. The mixture is filtered under $N_2$, and washed with ample amounts of methylene chloride and ether and dried under vacuum at 40° C. overnight to give a brown resin. FIG. 17 is a reaction scheme for preparation of an initiator immobilized on a polystyrene bead.

Examples 11-17 describe the procedure for ATRP polymerization of polymer precursors using initiators immobilized on a substrate.

Example 11

Figure 18:
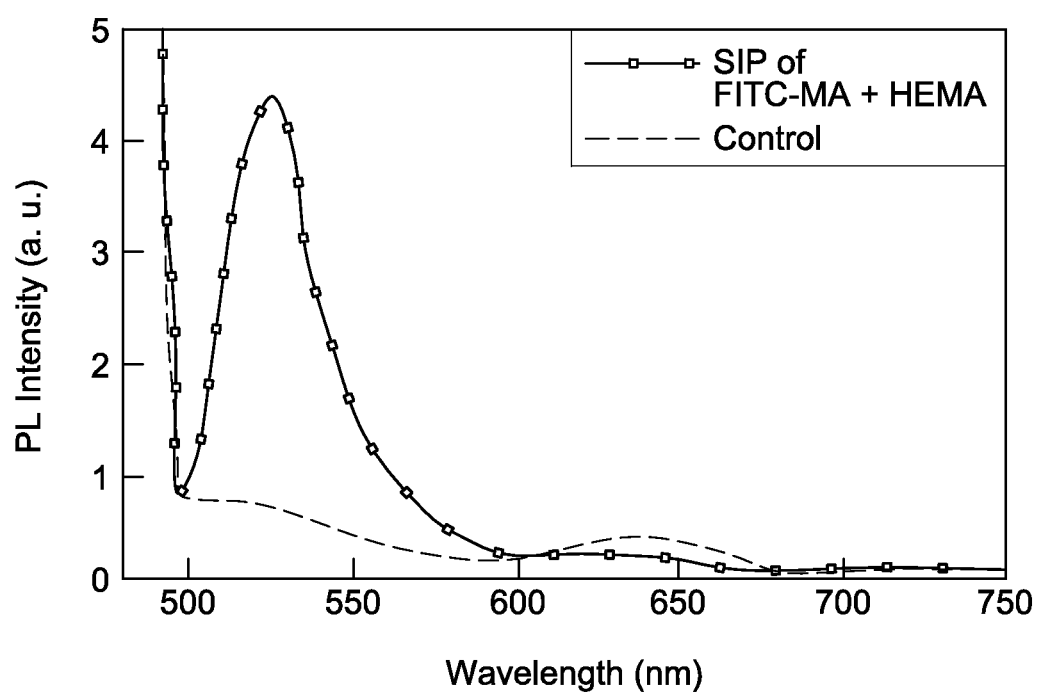
FIG. 18 is a plot of fluorescence intensity of slides prepared in Example 12.

Surface Initiated ATRP Co-Polymerization of Non-Fluorescent Monomer (HEMA) and Fluorescent Monomer (FITC-MA) on Quartz Slides 1.5 mL of 2-hydroxyethylene methacrylate (HEMA) is dissolved in 1.5 mL of degassed deionized water. CuCl (10.3 mg, 0.1 mmol), $CuBr_2$ (6.8 mg, 0.03 mmol) and 2,2'-bipyridine (46 mg, 0.29 mmol) are added to a vial containing both the initiator-modified quartz slides (from Example 7) and unmodified control quartz slides. The vial is sealed with a rubber septum and degassed. The monomer solution is then transferred into the vial and a homogeneous brown solution forms upon gentle shaking. A 1.0 mL of FITC-MA solution is introduced with a syringe. The polymerization is carried out at room temperature over night. The quartz slides are then removed from the reaction mixture, rinsed with deionized water, DMF and then deionized water successively and dried in air. Fluorescence spectra are measured with an excitation at 475 nm (as shown in FIG. 18). Surface initiated polymerization (SIP) of FITC-MA and HEMA showed a fluorescence peak when compared to a control sample (blank slide).

Example 12

Surface Initiated ATRP Co-Polymerization of Non-Fluorescent Monomer (HEMA) and Fluorescent Monomer (FITC-MA) on Quartz Slides A glass tube is charged with FMA (75 mg), NaOH (7.5 mg), $CuBr_2$ (8 mg), water (0.5 mL) and HEMA (0.5 mL). After all materials dissolve, the pH value of the solution is adjusted to about 8 by adding $NaHCO_3$. The mixture in the tube is degassed with two freeze-pump-thaw cycles and 160 µL of CuCl and $Me_6$TREN solution ($[Cu^{+1}]$=0.5 mg/µl, CuCl:$M_e$6TREN=1:1.5) is added. After an additional freeze-pump-thaw cycle, the ATRP initiator modified quartz slides from Example 7 are added under argon, and then a final freeze-pump-thaw cycle is performed. The polymerization is carried out at room temperature overnight. The quartz slides are then removed from the reaction mixture and rinsed with deionized water, DMF and $NaHCO_3/Na_2CO_3$ buffer successively and dried in air. Fluorescence spectra are then measured with a Perkin-Elmer LS55 luminescence spectrometer with an excitation at 460 nm.

Example 13

Surface Initiated ATRP Co-Polymerization of Non-Fluorescent Monomer (MPEO) and Fluorescent Monomer (FITC-MA) Using Biotinylated-Initiator Modified Quartz Slides A glass tube is charged with FITC (20 mg), NaOH (1.5 mg), $CuBr_2$ (1.5 mg), water (0.2 mL) and MPEO (0.1 mL). After all materials dissolved, the pH of the solution is adjusted to about 8 with $NaHCO_3$. The mixture in the tube is degassed with two freeze-pump-thaw cycles and 28 µL of CuCl and $Me_6$TREN solution ($[Cu+1]$=0.5 mg/µl, CuCl:$Me_6$TREN=1:1.5) is added. After additional freeze-pump-thaw cycles, the initiator-modified quartz slides are added under argon and a final freeze-pump-thaw cycle is performed. The polymerization is carried out at room temperature overnight. The quartz slides are then removed from the reaction mixture and rinsed with deionized water, DMF and $NaHCO_3/Na_2CO_3$ buffer successively and dried in air. Fluorescence spectra are then measured with Perkin-Elmer LS55 luminescence spectrometer with an excitation peak at 460 nm.

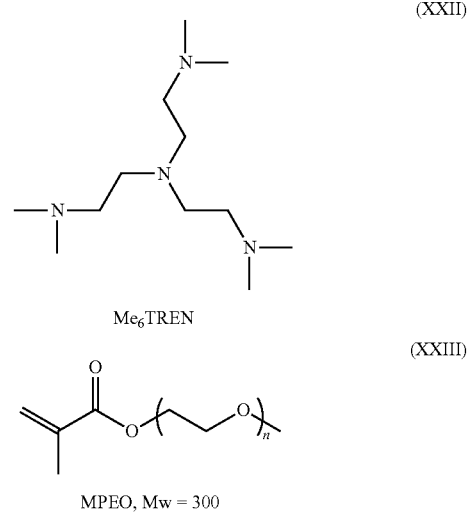

$Me_6$TREN (XXII)

MPEO, Mw = 300 (XXIII)

Example 14

Surface Initiated ATRP Co-Polymerization of Non-Fluorescent Monomer (MPEO) and Fluorescent Monomer (FITC-MA) on Initiator Modified Magnetic Particles A glass tube is charged with FITC-MA (10 mg), NaOH (2 mg), $CuBr_2$ (0.8 mg), water (0.1 mL) and MPEO (0.1 mL). After all materials dissolve in the solution, the pH value of the solution is adjusted to about 8 by adding $NaHCO_3$. Then 0.1 mL of magnetic particle solution is added by syringe. The mixture in the tube is degassed with three freeze-pump-thaw cycles. Then 14 μL of CuCl and Me₆TREN solution ([Cu] =0.5 mg/μL, CuCl:Me₆TREN=1:1.5) is added and the mixture is reacted without stirring overnight. The iron oxide particles are collected with a magnet, and sequentially washed with deionized water three times and NaHCO$_3$/Na$_2$CO$_3$ buffer (pH=9.6) twice. Fluorescence spectra are measured with a Perkin-Elmer LS55 luminescence spectrometer with excitation at 460 nm in NaHCO$_3$/Na$_2$CO$_3$ buffer.

Example 15

Surface Initiated ATRP Co-Polymerization of Non-Fluorescent Monomer (MPEO) and Fluorescent Monomer (FITC-MA) on Initiator Modified Quartz Slides to Observe the Effect of Quenching Quartz slides are modified with 3-aminopropyltriethoxysilane and trimethoxysilane (TMS) and subsequently modified with NHS-ATRP initiator. Two series of quartz slides are prepared using 1% (v/v) and 10% (v/v) concentration of 3-aminopropyltriethoxysilane. Series 1 quartz slides are modified with 1% (v/v) 3-aminopropyltriethoxysilane and 99% trimethoxysilane (TMS) and subsequently modified with NHS-ATRP initiator. Series 2 quartz slides are modified with 10% (v/v) 3-aminopropyltriethoxysilane and 90% trimethoxysilane (TMS) and subsequently modified with NHS-ATRP initiator. CuCl:CuBr$_2$:Bipy in a molar ration of 1:0.3:2 and at a concentration of 25 mM is used as a catalyst. Eight different polymerization reactions are conducted by varying the molar ratio of fluorescent monomer (FITC-MA) to non-fluorescent monomer (MPEO) with a total concentration of 1M. The molar ratios of FITC-MA to MPEO are 100:0, 1:0, 1:1, 1:2, 1:5, 1:10, 1:20, 1:50, and 1:100. Two control samples: (TMS1 and TMS2) using trimethoxy silane modified quartz slides with FITC-MA and MPEO in 1M concentrations are used for comparison.

Figure 19:
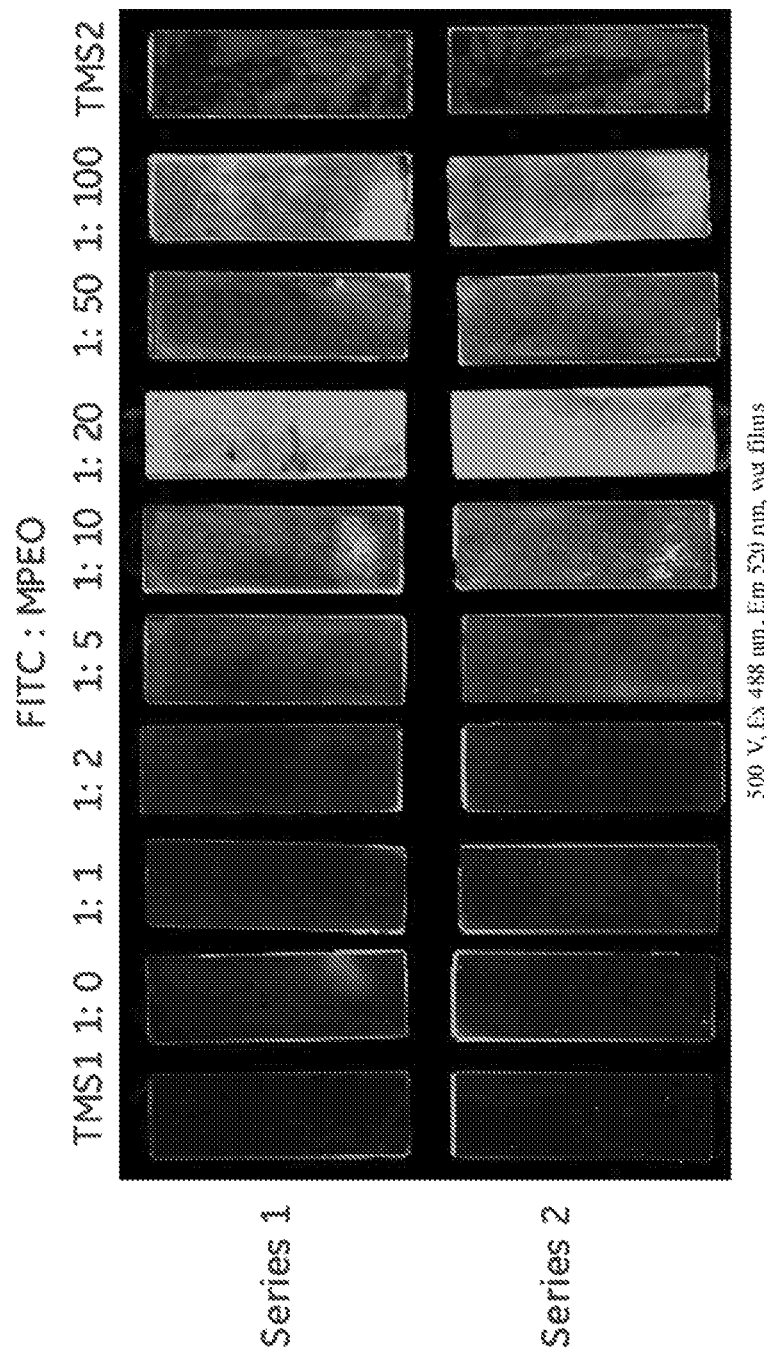
FIG. 19 shows the fluorescence images of slides prepared in Example 15.
Figure 20:
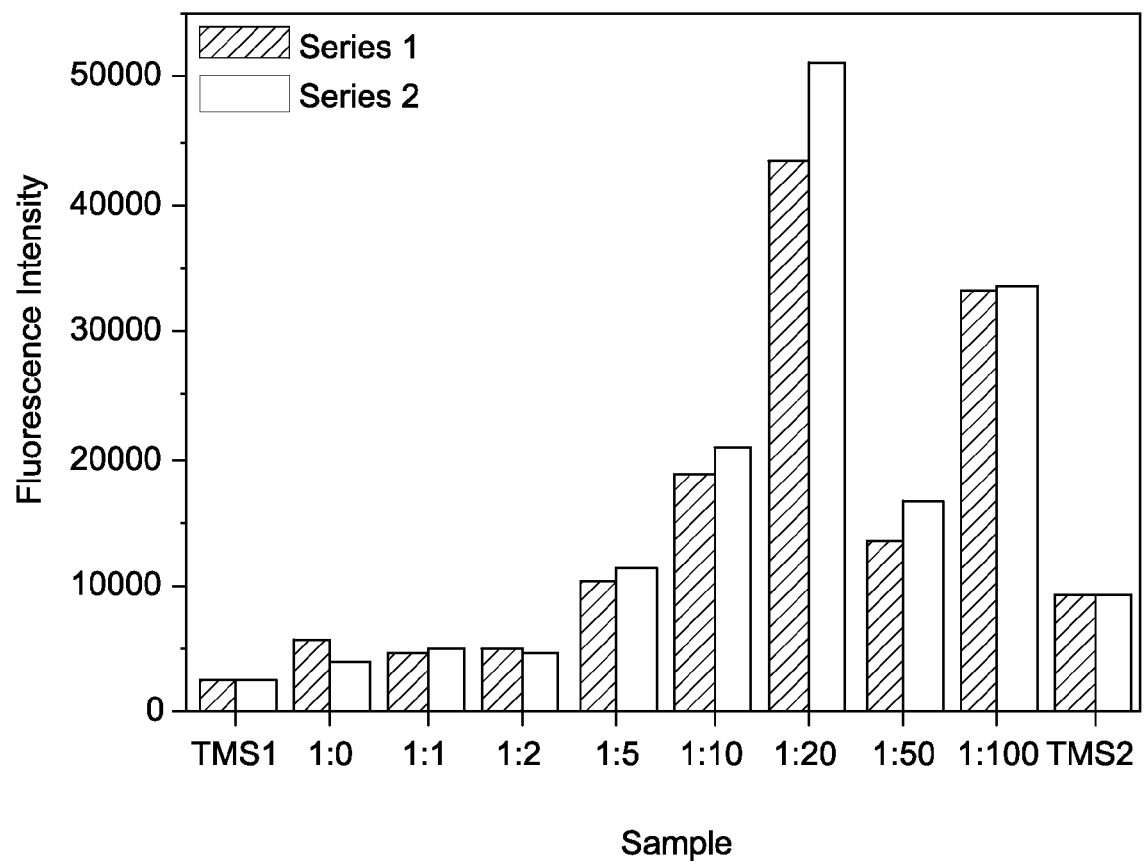
FIG. 20 shows the fluorescence intensity of slides prepared in Example 15.

FIGS. 19 and 20 show the fluorescence images and the fluorescence intensity of the series 1 and series 2 samples as a function of molar ratio of FITC-MA to MPEO. Optimum intensity seems to be obtained using a molar ratio of 1:20. At higher molar ratios quenching of signal between the florescent monomers is seen.

Example 16

Figure 21:
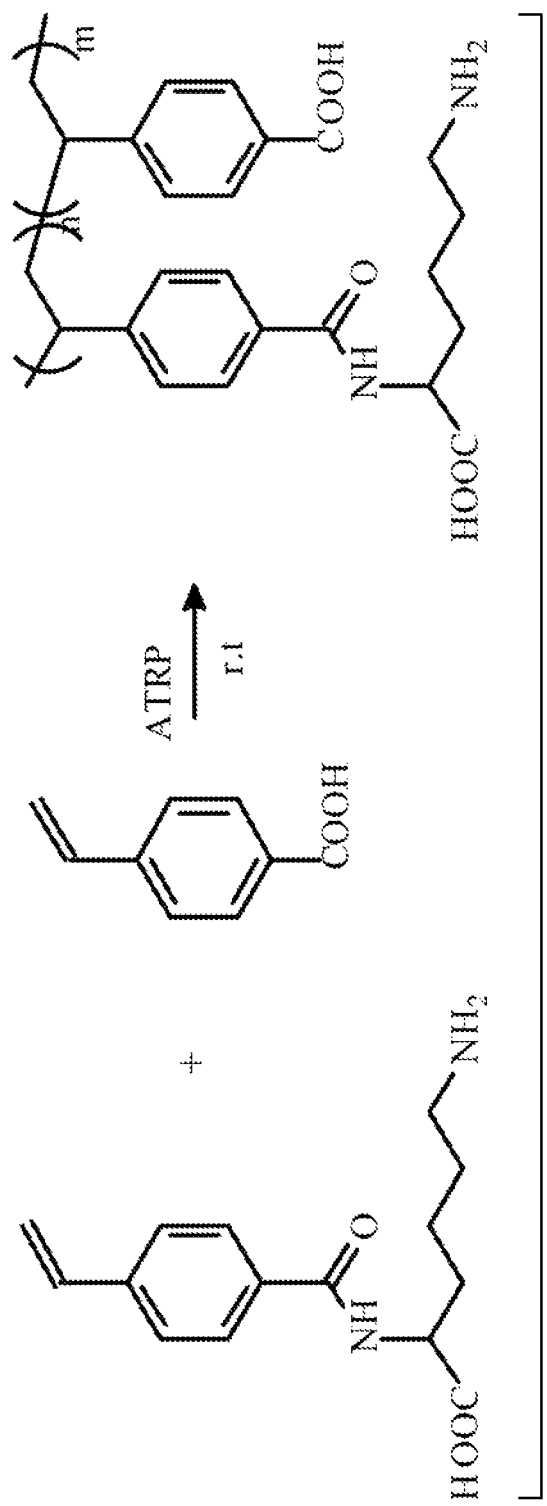
FIG. 21 is a reaction scheme for synthesis of a polymer using a modified polymer precursor in accordance with one embodiment of the invention.

Surface Initiated ATRP Co-Polymerization of Non-Fluorescent Monomer (VBA) and Bifunctional ATRP Monomer (VBA-Lys) on Initiator Modified Quartz Slides and Post-Polymerization Detection By Covalent Functionalization Co-polymerization of VBA-Lys and VBA on supported ATRP initiator quartz surface: A glass tube is charged with VBA (100 mg), VBA-Lysine (10 mg), NaOH (30 mg, in solution, 100 mg/mL), and water (0.1 mL). The materials are dissolved, and then the pH of the solution is adjusted to about 8 with solid NaHCO$_3$. The mixture of monomers and catalyst is degassed with three freeze-pump-thaw cycles. Then, 3.8 μl of CuCl and 2,2'-bipyridine (bpy) solution ([Cu$^{+1}$]=0.5 mg/μL, CuCl:bpy=1:1.5) is added and the mixture is transferred to a reaction chamber containing a species that includes an initiator, e.g. initiator-modified quartz. After polymerizing overnight, the reaction is quenched by rinsing the quartz with excess water. This process yields a lysine-labeled polymer, as shown in FIG. 21.

Visualization of surface bound VBA-Lys/VBA co-polymer: The lysine-labeled polymer can be conjugated to a variety of dyes via the primary amine of lysine. For instance, in this example the lysine labeled polymer from the previous step is subsequently stained with Cy5 NHS-mono ester under basic conditions and quantified fluorometrically, as shown in FIG. 22. Absorbance of surface initiated polymerization (SIP) reaction product post-labeling is greater than that of the control. Fluorescence intensity of SIP polymer-post labeling is greater than that of control and that of the SIP polymer before labeling.

Example 17

Surface Initiated ATRP Polymerization of Non-Fluorescent Monomer (VBA) on Initiator Modified Quartz Slides and Post-Polymerization Detection Using Fluorescent Polymer Polymerization of vinyl benzoic acid on supported ATRP initiator quartz surface. Vinyl benzoic acid, i.e. VBA, (0.500 g, 3.38 mmol) is dissolved in 1.5 mL degassed deionized water containing 0.126 g of sodium hydrogencarbonate and 0.130 g of sodium hydroxide to form a clear solution. CuBr (9.9 mg, 0.138 mmol), CuBr$_2$ (5.1 mg, 0.023 mmol) and 2,2'-bipyridine (32 mg, 0.207 mmol) are added to a vial containing both the ATRP initiator modified quartz slides from Example 7 and unmodified control slides. The vial is sealed with a rubber septum and degassed. The monomer solution is then transferred to the vial and a homogeneous brown solution forms upon gentle shaking. The polymerization is carried out at room temperature over night. The quartz slides are then removed from the reaction mixture, rinsed with deionized water, DMF, and then deionized water successively and then dried in air. UV-vis spectra of the slides are recorded (as shown in FIG. 23).

Visualization of surface bound poly(vinyl benzoic acid). To stain the surface of the slides, quarternized polyfluorene-block-poly(dimethylaminoethylene mathacrylate) is dissolved in 1:1 DMSO/water to form a 4 mg/mL clear solution. The slides are immersed in the solution for 15 minutes and rinsed with deionized water thoroughly. Fluorescence spectra are then measured with excitation at or near the absorption peak, which in this case is about 375 nm (FIG. 23). Absorbance of surface initiated polymerization (SIP) reaction product post-labeling is greater than that of the control. Fluorescence intensity of SIP polymer-post labeling is greater than that of control and that of the SIP polymer before labeling.

Examples 18 and 19 describe the procedure for ROMP polymerization of polymer precursors using initiators immobilized on a substrate.

Example 18

Surface Initiated ROMP Polymerization of Fluorescent Monomer Using ROMP Initiator Modified Polystyrene Beads Polymerization of Cy5-labeled 5-Norbornene-2-methanamine using the supported catalyst-Bis(tricyclohexylphosphine)benzylidine ruthenium dichloride polystyrene resin. Under N$_2$, a solution of Cy5-labeled 5-Norbornene-2-methanamine (4.2 mg, 5.52×10$^{-3}$ mmol) in 100 ml of DMF is added to the Bis(tricyclohexylphosphine)benzylidine ruthenium dichloride polystyrene resin of Example 10 and the mixture is shaken overnight. The beads are washed several times with DMF, until the washes are clear. The fluorescent polymer-modified polystyrene beads are visualized using a confocal fluorescent microscope.

Example 19

Surface Initiated ROMP Polymerization of Fluorescent Monomer (Cy5-Norbornene) and Non-Fluorescent Monomer (Gluconate Norbornene) Using ROMP Initiator Modified Quartz Slides

Surface-functionalized ROMP initiator is synthesized by catalyzing a ROMP reaction of the surface-modified norbornene (using norbornene silane) using a ROMP catalyst (30 mg/mL). Two different concentrations of surface-immobilized ROMP initiator are employed: 1% (v/v) and 10% (v/v) concentration.

The surface-immobilized ROMP catalyst is used to initiate a polymerization reaction of a monomer mixture (1M): Cy5-norbornene (structure XVI) and gluconate norbornene (structure XVIII) in a 1:10 molar ratio. The surface-immobilized ROMP catalyst is also used to initiate a polymerization reaction of 1M monomer mixture: Cy5-PEG-norbornene and gluconate norbornene (structure XVIII) in a 1:10 molar ratio. Quartz slides-surface functionalized with an amine (at 1% (v/v) and 10% (v/v) concentration) having a monolayer of Cy5-NHS are used as controls.

Examples 20 and 21 describe the procedure for synthesis of branched polymers using initiators immobilized on a substrate.

Example 20

Surface Initiated ATRP-ATRP Graft Polymerization of Fluorescent Monomers Using ATRP Initiator Modified Quartz Slides

Quartz slides are modified with 10% (v/v) 3-aminopropyltriethoxysilane and 90% trimethoxysilane (TMS) and subsequently modified with NHS-ATRP initiator. $CuCl:CuBr_2$:Bipy in a molar ration of 1:0.3:2 and at a concentration of 25 mM is used as a catalyst. In the first ATRP reaction 1M of hydroxy ethyl methacryalte (HEMA) at a concentration of 25 mM is polymerized for 15 minutes using the surface-immobilized ATRP initiator. The hydroxy-functionalized polymer is then reacted with 2-bromoisobutyryl bromide (0.1 M) in TEA (0.1M) for 30 minutes. The resulting bromo-functionalized methacrylate polymer is subjected to another ATRP polymerization reaction using $Cu(I)Cl$, $Cu(II)Br_2$ and 2,2'-bipyridyl (1:0.3:2) catalyst at a concentration of 25 mM. The monomer used are FITC-MA and MPEO (1:20, mol to mol) at a concentration of 1 M. FIGS. 24-26 show the fluorescence images and fluorescence intensity values of the graft/branched ATRP-ATRP polymerization product, linear ATRP polymerization product, and the control samples (monolayer of 10% amine and blank slide). A linear polymer shows a 5× signal amplification versus the control sample after a polymerization time of 30 minutes. A branched polymer shows a 15× signal amplification versus the control sample after a polymerization time of 45 minutes.

Example 21

Surface Initiated ROMP-ATRP Graft Polymerization of Fluorescent Monomers Using ROMP Initiator Modified Quartz Slides

Quartz slides are modified with 10% (v/v) 3-aminopropyltriethoxysilane and 90% trimethoxysilane (TMS). ATRP initiator (Norbornene-methyl bromoisobutyrate) is copolymerized with norbornene-NHS and Norbornene acetate by ROMP method in THF solution and then the resulting macroinitiator is transferred to the amine-coated quartz surface via $NH_2$—NHS reaction. The resulting bromo-functionalized norbornene polymer immobilized on a quartz surface is then subjected to an ATRP polymerization reaction using $Cu(I)Cl$, $Cu(II)Br_2$ and 2,2'-bipyridyl (1:0.3:2) catalyst at a concentration of 25 mM. The monomers used are FITC-MA and MPEO (1:20, mol to mol) at a concentration of 1 M.

Examples 22 and 23 describe the procedure for synthesis of a first polymer and a second polymer in a single reaction mixture via ATRP and ROMP.

Example 22

Simultaneous ATRP and ROMP Polymerization in a Single Reaction Mixture in Aqueous Phase

Hydroxyethyl methacrylate (HEMA) and norbornene-acetate are simultaneously polymerized in a single reaction mixture in an aqueous phase by ATRP and ROMP respectively. The initiator/catalyst combination for the ATRP reaction is an organic halide and $Cu(I)Cl$, $Cu(II)Br_2$ and 2,2'-bipyridyl (1:0.3:2) catalyst at a concentration of 25 mM. The ROMP reaction is initiated using a $(PCy_3)_2Cl_2[Ru]$=CHPh catalyst.

Example 23

Simultaneous ATRP and ROMP Polymerization in a Single Reaction Mixture in THF

Hydroxyethyl methacrylate (HEMA) and norbornene-acetate are simultaneously polymerized in a single reaction mixture in THF by ATRP and ROMP respectively. The initiator/catalyst combination for the ATRP reaction is an organic halide and $Cu(I)Cl$, $Me_6Tren$ catalyst at a concentration of 25 mM. The ROMP reaction is initiated using a $(PCy_3)_2Cl_2[Ru]$=CHPh catalyst.

Example 24

Analyte Detection by Surface Initiated ATRP Reaction of a Fluorescent Monomer and Non-Fluorescent Monomer from a Complimentary DNA-Anti-Sense DNA Hybrid

A DNA sequence analyte is immobilized on a substrate using a biotinylated DNA sequence as the analyte and streptavidin particle as a substrate. An anti-sense DNA probe sequence having a 5' terminal $NH_2$ residue is reacted with NHS-ATRP initiator prior to hybridizing the probe with the analyte. This is followed by a hybridization reaction between the DNA analyte and anti-sense DNA probe. The hybridization is carried out for 5 hours. Following the hybridization reaction, the analyte-probe hybrid is subjected to an ATRP reaction using $Cu(I)Cl$, $Cu(II)Br_2$ and 2,2'-bipyridyl (1:0.3:2.9) catalyst at a concentration of 25 mM. The monomers used are FITC-MA and MPEO (1:20, mol to mol) at a concentration of 1 M.

An anti-sense DNA sequence with a single fluorescent dye FAM is hybridized against the DNA modified streptavidin particles and used as a control. FIG. 27 is a schematic illustration of the control sample and the test sample using ATRP polymerization. FIG. 28 shows the fluorescent intensity for the test sample prepared using surface-initiated polymerization reaction (SIPS) and the control sample having a single dye. SIPS-sample shows almost 1.5× signal intensity when compared to the sample with a single dye molecule.

Example 25

Multiplexing Using Two Probes Capable of Binding to Two Different Analytes

A multiplexing example of the invention is similar to Example 24, except that the present example includes a plurality of chemically distinct probes (different anti-sense DNA sequences) that recognize chemically distinct analytes (different complimentary DNA sequences). In this example, each type of chemically distinct probe is attached to a chemically distinct initiator. For instance, a first anti-sense DNA sequence that binds to a first analyte can be bonded to one or more an ATRP initiators, while a second anti-sense DNA sequence that binds to a second analyte can be bonded to one or more ROMP initiators. According to this example, a sample is exposed to the first and second anti-sense DNA sequences thereby allowing any complimentary DNA sequences that may be present to bond to the anti-sense DNA sequences. The DNA/DNA hybrids are exposed in series to ATRP and ROMP reaction conditions, thus forming a first polymer by ATRP, and a second polymer by ROMP. Furthermore, the first and second polymers can have colors or analytical signals that are distinct from each other. That is to say, the polymers can absorb and/or photoluminesce in different regions of the electromagnetic spectrum. Therefore, the presence of the first and second analytes can be distinguished and quantitatively determined in a single sample.

Example 26

Single Analyte Detection Using Two Probes Capable of Binding to the Single Analyte An analyte detection example of the invention is similar to Example 24, except that the present example includes a plurality of chemically distinct probes (different anti-sense DNA sequences) that recognize distinct binding sites on a single analyte (complementary DNA sequence). In this example, each type of chemically distinct probe is attached to a chemically distinct initiator. For instance, a first anti-sense DNA sequence that binds to a complimentary sequence in the analyte DNA can be bonded to an ATRP initiator, while a second anti-sense DNA sequence that binds to a different complementary sequence in the analyte DNA can be bonded to a ROMP initiator. According to this example, a sample is exposed to the first and second anti-sense DNA sequences thereby allowing any complimentary DNA sequences that may be present to bond to the anti-sense DNA sequences. The DNA/DNA hybrids are then exposed in series to ATRP and ROMP reaction conditions, thus forming a first polymer by ATRP, and a second polymer by ROMP. A coincident signal from the first polymer and the second polymer is observed. Therefore, the presence of analyte can be accurately distinguished and quantitatively determined in a single sample.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

The foregoing examples are illustrative of some features of the invention. The appended claims are intended to claim the invention as broadly as has been conceived and the examples herein presented are illustrative of selected embodiments from a manifold of all possible embodiments. Accordingly, it is Applicants' intention that the appended claims not limit to the illustrated features of the invention by the choice of examples utilized. As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges there between. It is to be expected that variations in these ranges will suggest themselves to a practitioner having ordinary skill in the art and, where not already dedicated to the public, the appended claims should cover those variations. Advances in science and technology may make equivalents and substitutions possible that are not now contemplated by reason of the imprecision of language; these variations should be covered by the appended claims.

The invention claimed is:
1. A composition, comprising:
a first probe;
a first initiator component bonded to the first probe;
a second probe chemically distinct from the first probe;
a second initiator component bonded to the second probe, wherein the first probe and the second probe are bonded to a single analyte such that the first initiator component and the second initiator component form an initiator, with the proviso that the first initiator component and the second initiator component are independently inactive when the first probe and the second probe are not bonded to the analyte,
wherein the initiator is present between the polymer and each of the first probe and the second probe; and
a polymer bonded to the initiator, wherein the polymer is bonded to a plurality of signal generators, wherein the polymer comprises structural units derived from a poly- mer precursor comprising an atom transfer radical polymerization (ATRP) monomer, a ring opening metathesis polymerization (ROMP) monomer, or combinations thereof.

2. The composition as defined in claim 1, wherein the polymer is linear.

3. The composition as defined in claim 1, wherein the polymer is branched.

4. The composition as defined in claim 1, wherein the polymer has a number average degree of polymerization in a range of from about 100 grams per mole to about 100,0000 grams per mole.

5. The composition as defined in claim 1, wherein the polymer has a unimodal molecular weight distribution.

6. The composition as defined in claim 1, wherein the polymer has a polydispersity that is less than about 1.5.

7. The composition as defined in claim 1, wherein the plurality of signal generators comprise one or more of a chromophore, a fluorophore, a Raman-active tag, an electroactive label, a magnetic label, or a radioactive label.

8. The composition as defined in claim 1, wherein the plurality of signal generators comprise one or more of an enzyme, or an enzyme substrate.

9. The composition as defined in claim 1, wherein the analyte comprises one or more pollutants selected from the group consisting of air-pollutants, water-pollutants, soil pollutants, and combinations of two or more thereof.

10. The composition as defined in claim 1, wherein the analyte comprises one or more spoilage indicators associated with a meat by-product.

11. The composition as defined in claim 1, wherein the analyte comprises one or more chemical warfare agents selected from the group consisting of incapacitating agents, lachrymators, vesicant, blister agents, nerve agents, pulmonary agents, blood agents, malodorants, and combinations of two or more thereof.

12. The composition as defined in claim 1, wherein the analyte comprises one or more biological warfare agents selected from the group consisting of pathogens, toxins, and combinations thereof.

13. The composition as defined in claim 12, wherein the pathogen is selected from the group consisting of bacteria, viruses, protozoa, fungi, parasites, prions, and combinations of two or more thereof.

14. The composition as defined in claim 1, wherein the analyte comprises one or more biomolecules selected from the group consisting of peptides, proteins, nucleic acids, polysaccharides, lipids, enzymes, enzyme substrates, antigens, haptens, aptamers, vitamins, and combinations of two or more thereof.

15. The composition as defined in claim 1, wherein the first probe and the second probe independently comprises one or more of a nucleic acid, a protein, a sugar, a lipid, a carbohydrate, a vitamin, an enzyme, or an enzyme substrate.

16. The composition as defined in claim 1, wherein the plurality of signal generators comprise a fluorophore.

17. The composition as defined in claim 16, wherein the fluorophore comprises a fluorescein, a cyanine, or combinations thereof.

18. The composition of claim 1, wherein the polymer comprises structural units derived from a polymer precursor having a structure:

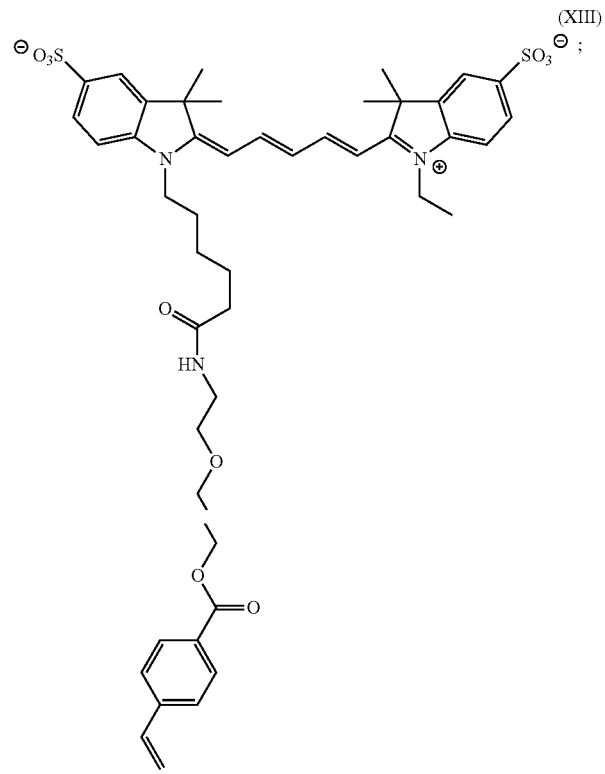

(XIII)

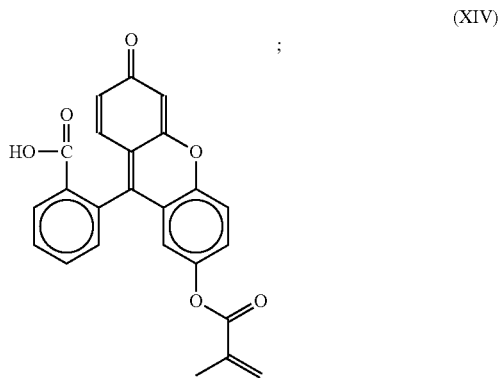

(XIV)

-continued
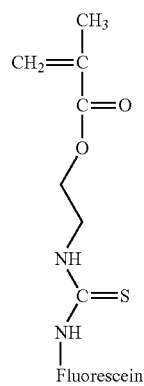
Fluorescein;
(XV)
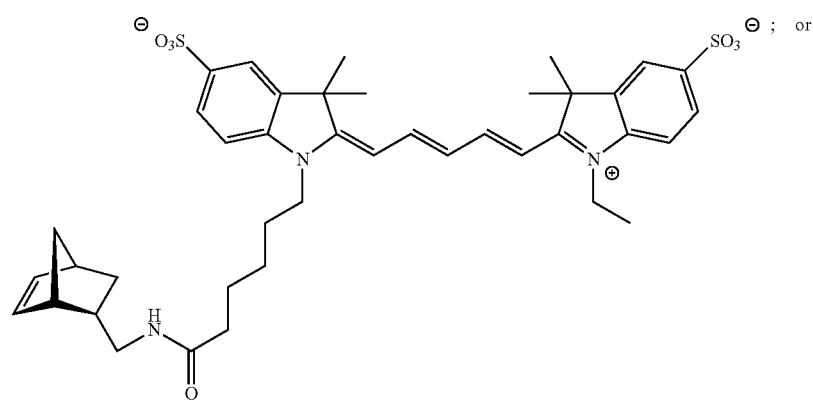
; or
(XVI)
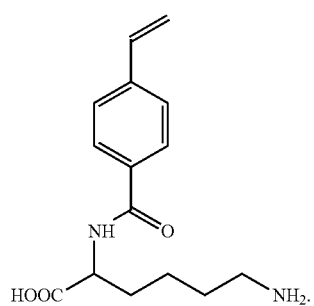
.
(XIX)
* * * * *

UNITED STATES PATENT AND TRADEMARK OFFICE
CERTIFICATE OF CORRECTION

| | |
|---|---|
| PATENT NO. | : 8,778,846 B2 |
| APPLICATION NO. | : 11/680652 |
| DATED | : July 15, 2014 |
| INVENTOR(S) | : Nelson et al. |

It is certified that error appears in the above-identified patent and that said Letters Patent is hereby corrected as shown below:

In the Specification,

In Column 1, Line 19, delete "Thr" and insert -- The --, therefor.

In Column 2, Line 13, delete "DRAWING FIGURES" and insert -- DRAWINGS/FIGURES --, therefor.

In Column 3, Line 18, delete "Thr" and insert -- The --, therefor.

In Column 3, Line 66, delete "pyrolysine." and insert -- pyrrolysine. --, therefor.

In Column 5, Lines 44-45, delete "ethylenediaminetetracetate" and insert -- ethylenediaminetetraacetate --, therefor.

In Column 18, Line 8, delete "his" and insert -- bis --, therefor.

In Column 18, Line 11, delete "his" and insert -- bis --, therefor.

In Column 18, Line 12, delete "his" and insert -- bis --, therefor.

In Column 18, Line 13, delete "his" and insert -- bis --, therefor.

In Column 18, Line 14, delete "his" and insert -- bis --, therefor.

In Column 18, Line 16, delete "his" and insert -- bis --, therefor.

In Column 18, Line 32, delete "perfluororoisobutylene." and insert -- perfluoroisobutylene. --, therefor.

Signed and Sealed this
Sixteenth Day of December, 2014

Michelle K. Lee
*Deputy Director of the United States Patent and Trademark Office*

CERTIFICATE OF CORRECTION (continued)

In Column 19, Line 32, delete "lysteria" and insert -- listeria --, therefor.

In Column 20, Line 11, delete "crosslinked species," and insert -- species, --, therefor.

In Column 23, Line 13, delete "(Cibacron." and insert -- (Cibacron --, therefor.

In Column 25, Lines 19-46, in Equation (XIII), delete " 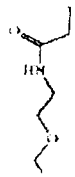 " and insert -- 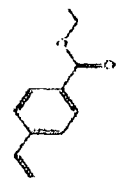 --, therefor.

In Column 37, Line 63, delete "6.3 mmol)" and insert -- 6.3 μmol) --, therefor.

In Column 37, Line 64, delete "6.3 mmol)" and insert -- 6.3 μmol) --, therefor.

In Column 41, Line 1, delete "TIIF." and insert -- THF. --, therefor.

In Column 43, Line 3, delete "stiffing" and insert -- stirring --, therefor.

In Column 45, Line 39, delete "methacryalte" and insert -- methacrylate --, therefor.